US012697181B2

(12) United States Patent     (10) Patent No.:   US 12,697,181 B2

Kreciglowa et al.     (45) Date of Patent:     Aug. 4, 2026

(54) SYSTEM AND METHOD OF CONTROLLING MOTION OF KINEMATIC CHAINS

(71) Applicant: Auris Health, Inc., Redwood City, CA (US)

(72) Inventors: Nadia S. Kreciglowa, San Francisco, CA (US); Yanan Huang, Sunnyvale, CA (US); Ying Mao, San Mateo, CA (US); Eloi Le Roux, San Francisco, CA (US)

(73) Assignee: Auris Health, Inc., Santa Clara, CA (US)

( * ) Notice: Subject to any disclaimer, the term of this patent is extended or adjusted under 35 U.S.C. 154(b) by 473 days.

(21) Appl. No.: 18/106,942

(22) Filed: Feb. 7, 2023

(65) Prior Publication Data

US 2023/0181269 A1     Jun. 15, 2023

Related U.S. Application Data

(63) Continuation of application No. PCT/IB2021/058608, filed on Sep. 21, 2021.

(Continued)

(51) Int. Cl.
| | |
|---|---|
| *A61B 34/30* | (2016.01) |
| *A61B 34/00* | (2016.01) |
| *B25J 9/00* | (2006.01) |

(52) U.S. Cl.
CPC .............. *A61B 34/30* (2016.02); *A61B 34/74* (2016.02); *B25J 9/0009* (2013.01); *B25J 9/0045* (2013.01)

(58) Field of Classification Search
CPC . B25J 9/0009; B25J 9/0045; A61B 2034/105; A61B 2034/2051;

(Continued)

(56) References Cited

U.S. PATENT DOCUMENTS

| | | |
|---|---|---|
| 9,763,741 B2 | 9/2017 | Alvarez et al. |
| 11,026,758 B2 | 6/2021 | Mintz et al. |

(Continued)

FOREIGN PATENT DOCUMENTS

| | | |
|---|---|---|
| WO | 95/16396 A1 | 6/1995 |
| WO | 2011/153082 A2 | 12/2011 |

(Continued)

OTHER PUBLICATIONS

European Search Report, Extended, and Written Opinion dated Oct. 7, 2024 for Application No. EP 21874674.1, 14 pgs.

(Continued)

*Primary Examiner* — Scott Luan

(74) *Attorney, Agent, or Firm* — FBT Gibbons LLP

(57) ABSTRACT

Robotic systems can be capable of commanding bar translation. A robotic system can include a robotically controlled first kinematic chain, a robotically controlled second kinematic chain that is movably coupled to the first kinematic chain, and a controller that is communicably coupled to the first kinematic chain and the second kinematic chain. The robotic system can be figured to obtain data corresponding to the first kinematic chain, and control movement of the second kinematic chain in accordance with the data corresponding to the first kinematic chain.

39 Claims, 44 Drawing Sheets

Related U.S. Application Data

(60) Provisional application No. 63/086,021, filed on Sep. 30, 2020.

(58) Field of Classification Search
CPC .... A61B 2034/2059; A61B 2034/2061; A61B 2034/2065; A61B 2034/301; A61B 2034/742; A61B 2090/064; A61B 2090/065; A61B 2090/306; A61B 2090/309; A61B 2090/376; A61B 34/25; A61B 34/30; A61B 34/74; A61B 90/361
See application file for complete search history.

(56) References Cited

U.S. PATENT DOCUMENTS

| | | | |
|---|---|---|---|
| 11,510,736 | B2 | 11/2022 | Rafii-Tari et al. |
| 2007/0013336 | A1 | 1/2007 | Nowlin et al. |
| 2014/0052153 | A1 | 2/2014 | Griffiths et al. |
| 2015/0104284 | A1* | 4/2015 | Riedel ...................... B25J 15/00 |
| | | | 414/738 |

| | | | |
|---|---|---|---|
| 2019/0083190 | A1 | 3/2019 | Graves et al. |
| 2019/0216555 | A1 | 7/2019 | DiMaio et al. |
| 2020/0146769 | A1 | 5/2020 | Eyre et al. |
| 2020/0237423 | A1 | 7/2020 | Witte et al. |
| 2020/0237458 | A1 | 7/2020 | DeFonzo et al. |

FOREIGN PATENT DOCUMENTS

| | | |
|---|---|---|
| WO | 2015/142955 A1 | 9/2015 |
| WO | 2018/060945 A1 | 4/2018 |

OTHER PUBLICATIONS

PCT International Search Report; PCT/IB2021/058608; Dec. 21, 2021; 7 pages.
PCT Written Opinion of the International Searching Authority; PCT/IB2021/058608; Dec. 21, 2021; 4 pages.
Chinese First Office Action and Search Report dated Mar. 27, 2025, for Application No. 202180066797.3, 14 pages.
Chinese Second Office Action dated Jul. 18, 2025, for Application No. 202180066797.3, 16 pages.

* cited by examiner

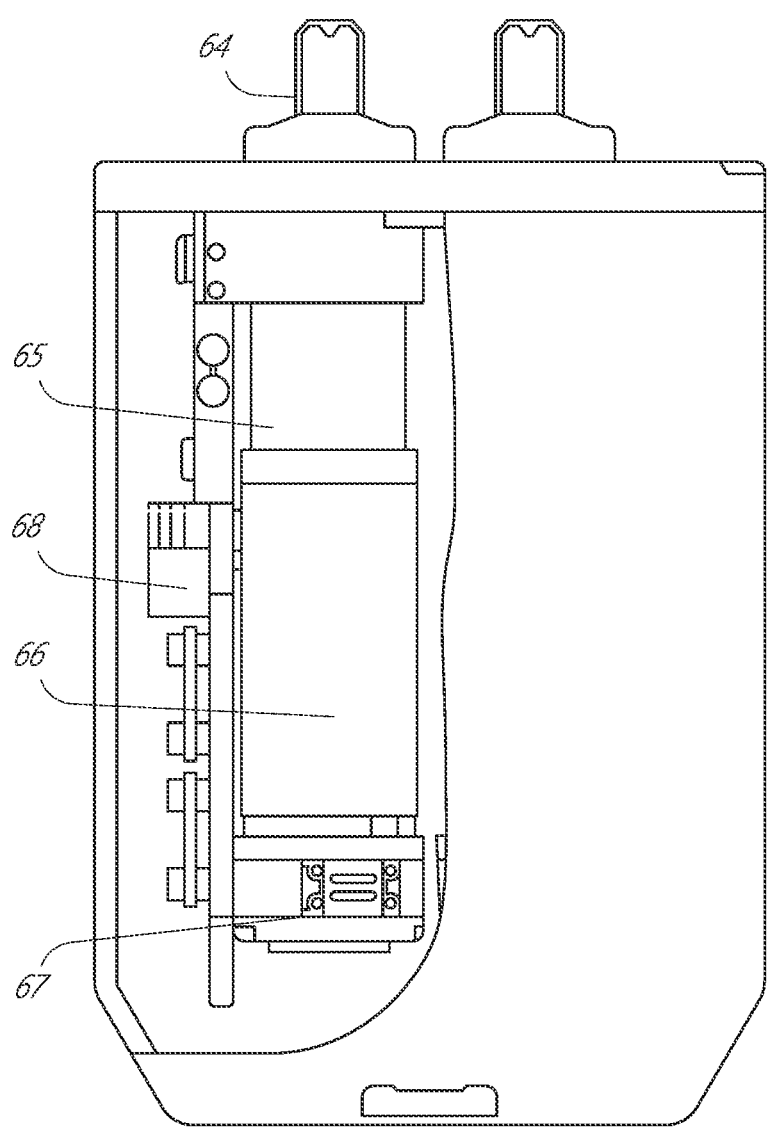
FIG. 15

RIGHT

X

Z

Y 210-6

210-5

210-4

220-2

J3

726

LEGS 210-1

702

210-2

220-1

210-3

LEFT 212-1

722

304-1-5

304-1-6

718

202

712

206

728

H3

704

HEAD

200

Extracted from FIG. 27A      (i)

Extracted from FIG. 27B      (ii)

Extracted from FIG. 27C      (iii)

Extracted from FIG. 27D      (iv)

900

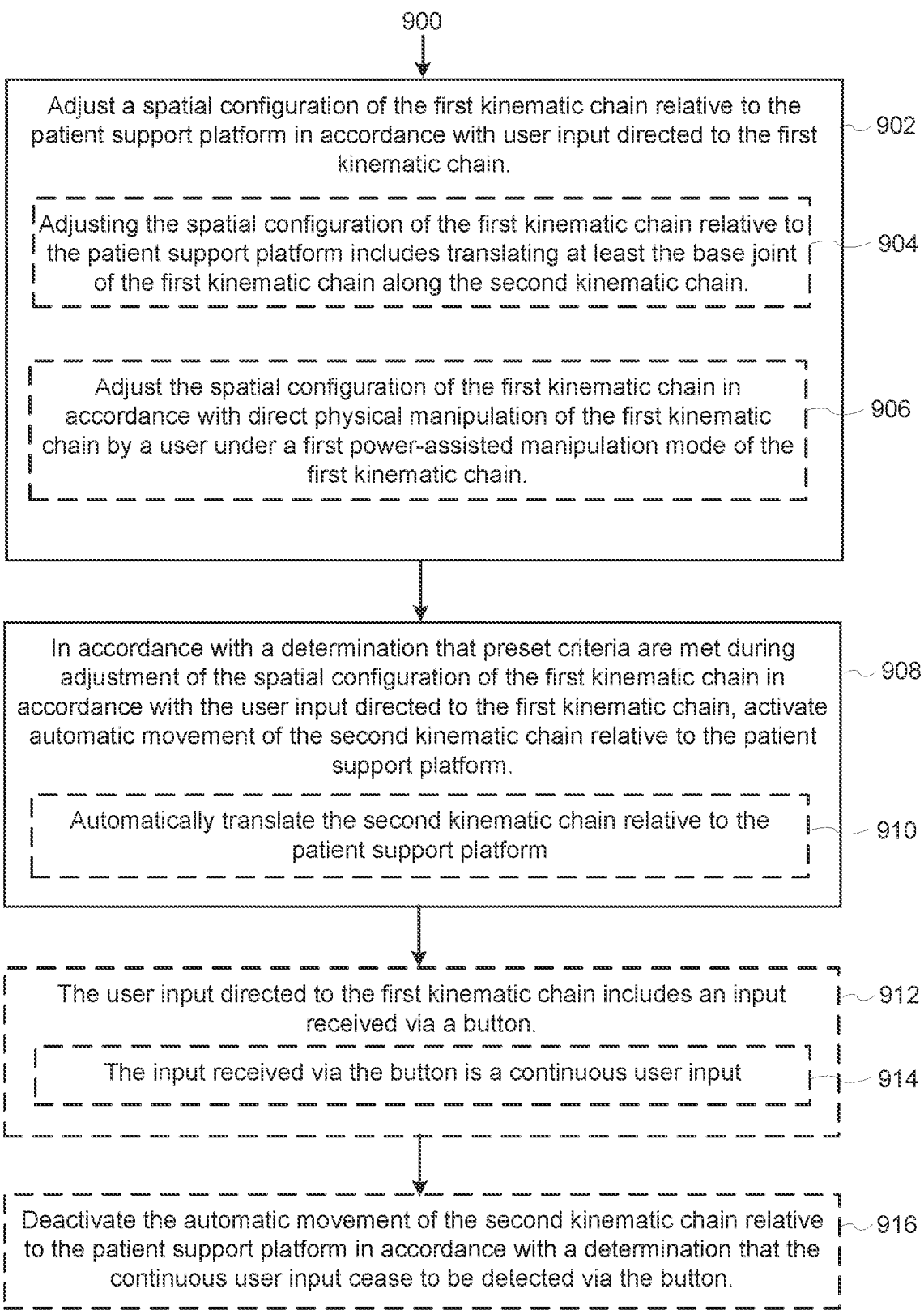

Adjust a spatial configuration of the first kinematic chain relative to the patient support platform in accordance with user input directed to the first kinematic chain. — 902

Adjusting the spatial configuration of the first kinematic chain relative to the patient support platform includes translating at least the base joint of the first kinematic chain along the second kinematic chain. — 904

Adjust the spatial configuration of the first kinematic chain in accordance with direct physical manipulation of the first kinematic chain by a user under a first power-assisted manipulation mode of the first kinematic chain. — 906

In accordance with a determination that preset criteria are met during adjustment of the spatial configuration of the first kinematic chain in accordance with the user input directed to the first kinematic chain, activate automatic movement of the second kinematic chain relative to the patient support platform. — 908

Automatically translate the second kinematic chain relative to the patient support platform — 910

The user input directed to the first kinematic chain includes an input received via a button. — 912

The input received via the button is a continuous user input — 914

Deactivate the automatic movement of the second kinematic chain relative to the patient support platform in accordance with a determination that the continuous user input cease to be detected via the button. — 916

FIG. 29

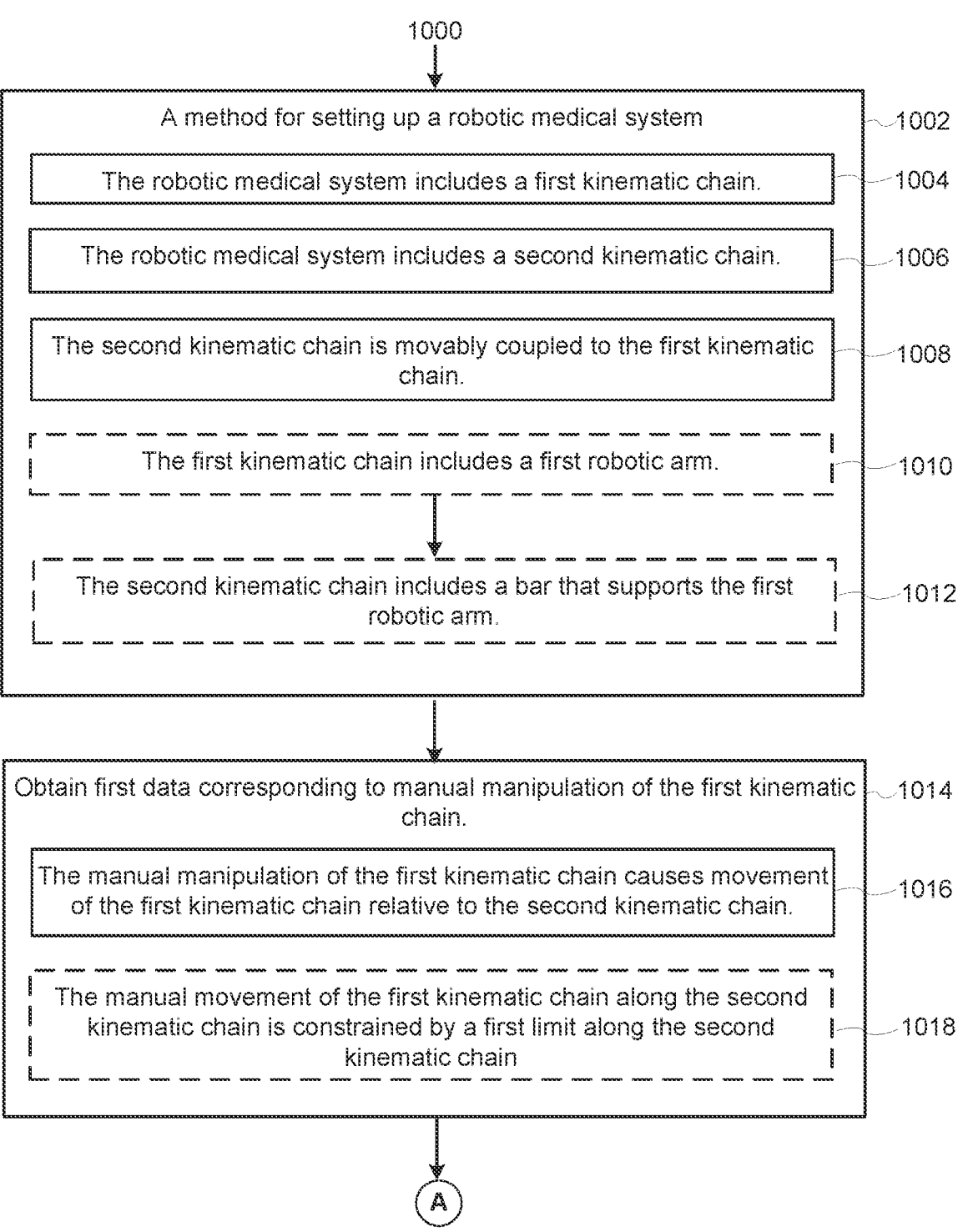

1000

A method for setting up a robotic medical system — 1002

The robotic medical system includes a first kinematic chain. — 1004

The robotic medical system includes a second kinematic chain. — 1006

The second kinematic chain is movably coupled to the first kinematic chain. — 1008

The first kinematic chain includes a first robotic arm. — 1010

The second kinematic chain includes a bar that supports the first robotic arm. — 1012

Obtain first data corresponding to manual manipulation of the first kinematic chain. — 1014

The manual manipulation of the first kinematic chain causes movement of the first kinematic chain relative to the second kinematic chain. — 1016

The manual movement of the first kinematic chain along the second kinematic chain is constrained by a first limit along the second kinematic chain — 1018

SYSTEM AND METHOD OF CONTROLLING MOTION OF KINEMATIC CHAINS

CROSS-REFERENCE TO RELATED APPLICATIONS

This application is a continuation of PCT Patent Application No. PCT/IB2021/058608, filed on Sep. 21, 2021, entitled "System And Method Of Controlling Motion Of Kinematic Chains," which claims the benefit of U.S. Provisional Patent Application No. 63/086,021, filed on Sep. 30, 2020, entitled "System And Method Of Controlling Motion Of Kinematic Chains," all of which are hereby incorporated by reference herein in their entireties.

TECHNICAL FIELD

The systems and methods disclosed herein are directed to robotic medical systems, and more particularly, to robotically controlled arms and arm supports of robotic medical systems.

BACKGROUND

A robotically-enabled medical system are capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

Such robotic medical systems may include robotic arms configured to control the movement of medical tool(s) during a given medical procedure. In order to achieve a desired pose of a medical tool, a robotic arm may be placed into a pose during a set-up process. Some robotically-enabled medical system may include an arm support (e.g., a bar) that is connected to respective bases of the robotic arms and supports the robotic arms.

SUMMARY

Before a procedure starts, an operator (e.g., a physician assistant, medical personnel, etc.) may be required to set up the robotic arms and an adjustable arm support of the robotic medical system to a desired overall configuration. In some circumstances, the operator can manually manipulate one or more robotic arms to their respective configurations (e.g., using admittance mode control, impedance mode control, or a combination thereof, etc.) during setup, but the operator has to separately adjust the arm support when the robotic arms are not in a manual manipulation mode. Sometimes, the operator is required to use an external controller to move the adjustable arm support while the robotic arms are kept stationary on the adjustment arm support. This limitation on when and how the adjustable arm support may be moved makes the setup process very cumbersome and time-consuming, because the operator may have to switch back and forth between adjusting the arm support and manipulating the robotic arms multiple times in order to finally achieve a desired overall configuration of the robotic medical system. The process is further complicated when a special bed configuration is required in combination with the configurations of the robotic arms and adjustable arm support. Furthermore, the complexity of separately adjusting multiple kinematic chains (e.g., multiple robotic arms, one or more adjustable arm support(s), and the patient bed, etc.) in multiple stages imposes significant requirements on the operator's experience level and expertise, to ensure efficiency of the setup process. In some cases, the limitation that the adjustable arm support has to be controlled by a remote controller away from the patient bed places significant physical burden on the operator to move back and forth between bedside controls of the robotic arms and remote controls of the adjustable arm support during setup, and increases the risk of collision with the robotic medical system or tripping over other objects (e.g., cables, monitors, etc.) in the operating room. With the significant cognitive and operational burden imposed on the operator during the setup process, risk of operator errors also increases, which may undermine the confidence of the medical personnel when using the robotic system and the safety of the patient. Accordingly, there is a need for a robotic medical system that better coordinate the motions and manipulations of multiple kinematic chains during setup, to more easily and conveniently achieve a desired overall configuration. There is also a need for a robotic medical system that can be easily and conveniently configured with bedside controls and reduced need for operation away from bedside of the robotic medical system.

As disclosed herein, enabling automatic motion of the adjustable arm support while a robotic arm is in a manual manipulation mode (e.g., in an impedance mode, or admittance mode, etc.) makes it easier and more efficient to configure the robotic medical system. In particular, starting and stopping automatic translation of the adjustable arm support when a robotic arm is being manipulated in a manual manipulation mode, based on movement data (e.g., position, speed, etc.) corresponding the robotic arm during manual manipulation can make final adjustments to system setup easier and faster. In addition, enabling automatic movement of the adjustable arm support by manipulating the robotic arm at bedside of the robotic medical system reduces the need for the operator to move back and forth in the operating room during set up of the robotic medical system, thereby improves setup efficiency and reduces the risks of collision and tripping in the operating room. As disclosed herein, to further improve the setup efficiency and reduce operator error, automatic movement of other robotic arms on the adjustable arm support are also enabled, to avoid collision and/or maintain position of remote center of motion for docked robotic arms.

The systems, methods and devices of this disclosure each have several innovative aspects, no single one of which is solely responsible for the desirable attributes disclosed herein.

In accordance with some embodiments of the present disclosure, a robotic system includes a robotically controlled first kinematic chain, a robotically controlled second kinematic chain that is movably coupled to the first kinematic chain, and a controller. The controller is communicably coupled to the first kinematic chain and the second kinematic chain. The controller includes one or more processors and memory. The memory stores instructions that, when executed by the one or more processors, cause the processors to obtain data corresponding to the first kinematic chain and control movement of the second kinematic chain in accordance with the data corresponding to the first kinematic chain.

In some embodiments, obtaining the data corresponding to the first kinematic chain includes obtaining the data while the first kinematic chain is in a manual manipulation mode.

In some embodiments, controlling the movement of the second kinematic chain in accordance with the data corresponding to the first kinematic chain includes automatically moving the second kinematic chain in accordance with a determination that the data corresponding to the first kinematic chain meets preset criteria.

In some embodiments, controlling the movement of the second kinematic chain includes controlling a translational movement of the second kinematic chain relative to a base of the robotic system.

In some embodiments, the first kinematic chain includes a first robotic arm. The second kinematic chain includes a bar that supports the first robotic arm.

In some instances, the first robotic arm includes a base joint that is coupled to the bar and capable of translating along the bar.

In some instances, the translation of the first robotic arm along the bar is constrained by a first limit along the bar.

In some instances, the first limit includes a haptic wall that limits an extent of manual translation of the first robotic arm along the bar.

In some instances, the automatic movement of the bar is triggered in accordance with a cutoff limit being exceeded by the first robotic arm.

In some instances, the data corresponding to the first kinematic chain includes a distance travelled by the first robotic arm along the bar.

In some instances, the data corresponding to the first kinematic chain includes a movement direction of the first robotic arm along the bar. Controlling the movement of the second kinematic chain includes moving the bar relative to a base of the robotic system in the movement direction of the first robotic arm.

In some embodiments, the robotic system further includes a robotically controlled third kinematic chain that is movably coupled to the second kinematic chain. The memory further stores instructions that, when executed by the one or more processors, cause the processors to control movement of the third kinematic chain in accordance with the movement of the second kinematic chain.

In some embodiments, the first kinematic chain includes a first robotic arm. The third kinematic chain includes a second robotic arm. The second kinematic chain includes a bar that supports the first robotic arm and the second robotic arm.

In some embodiments, controlling the movement of the third kinematic chain in accordance with the movement of the second kinematic chain includes: in accordance with a determination that first movement criteria are met, maintaining a spatial relationship between at least a portion of the third kinematic chain and the second kinematic chain during the movement of the second kinematic chain.

In some embodiments, controlling the movement of the third kinematic chain in accordance with the movement of the second kinematic chain includes: in accordance with a determination that second movement criteria are met, moving at least a portion of the third kinematic chain relative to the second kinematic chain during the movement of the second kinematic chain.

In some embodiments, controlling the movement of the third kinematic chain in accordance with the movement of the second kinematic chain includes: in accordance with a determination that third movement criteria are met, moving at least a first portion of the third kinematic chain relative to the second kinematic chain during the movement of the second kinematic chain while maintaining a position of a distal end portion of the third kinematic chain relative to a base of the robotic system.

In some embodiments, controlling the movement of the second kinematic chain in accordance with the movement of the first kinematic chain includes: in accordance with a determination that fourth movement criteria are met, stopping movement of the second kinematic chain.

In accordance with another aspect of the present disclosure, a robotic medical system includes a patient support platform a first kinematic chain, and a second kinematic chain. The first kinematic chain is movably coupled to the second kinematic chain. The robotic medical system also includes a controller comprising one or more processors and memory. The memory stores instructions that, when executed by the one or more processors, cause the processors to adjust a spatial configuration of the first kinematic chain relative to the patient support platform in accordance with user input directed to the first kinematic chain. In accordance with a determination that preset criteria are met during adjustment of the spatial configuration of the first kinematic chain in accordance with the user input directed to the first kinematic chain, the processors activate automatic movement of the second kinematic chain relative to the patient support platform.

In some embodiments, the first kinematic chain is movably coupled to the second kinematic chain via a base joint that is capable of translating along the second kinematic chain. Adjusting the spatial configuration of the first kinematic chain relative to the patient support platform includes translating at least the base joint of the first kinematic chain along the second kinematic chain.

In some embodiments, activating the automatic movement of the second kinematic chain relative to the patient support platform includes automatically translating the second kinematic chain relative to the patient support platform.

In some embodiments, the first kinematic chain includes a first robotic arm. The second kinematic chain includes a bar that supports the first robotic arm.

In some embodiments, the user input directed to the first kinematic chain is received via an input interface located on or proximate to the first kinematic chain.

In some embodiments, the user input directed to the first kinematic chain includes an input received via a button.

In some instances, the input received via the button is a continuous user input.

In some instances, the memory stores instructions that, when executed by the one or more processors, cause the processors to deactivate the automatic movement of the second kinematic chain relative to the patient support platform in accordance with a determination that the continuous user input ceases to be detected via the button.

In some embodiments, adjusting the spatial configuration of the first kinematic chain relative to the patient support platform in accordance with user input directed to the first kinematic chain includes adjusting the spatial configuration of the first kinematic chain in accordance with direct physical manipulation of the first kinematic chain by a user under a first power-assisted manipulation mode of the first kinematic chain.

In some embodiments, the preset criteria requires that a force detected on one or more preset portions of the first kinematic chain exceeds a preset threshold force during the adjustment of the spatial configuration of the first kinematic chain in order for the preset criteria to be met.

In another aspect, some embodiments include a method for setting up a robotic medical system. The robotic medical system includes a first kinematic chain and a second kinematic chain that is movably coupled to the first kinematic chain. The method includes obtaining first data corresponding to manual manipulation of the first kinematic chain. The manual manipulation of the first kinematic chain causes movement of the first kinematic chain relative to the second kinematic chain. The method further includes in accordance with a determination that the first data corresponding to manual manipulation of the first kinematic chain meets preset criteria, activating automatic movement of the second kinematic chain relative to a physical environment of the robotic medical system.

In some embodiments, the manual manipulation of the first kinematic chain causes translational movement of the first kinematic chain along a length of the second kinematic chain. The preset criteria are met in accordance with a determination that the translational movement of the first kinematic chain has exceeded a preset cutoff limit along the length of the second kinematic chain.

In some embodiments, the first kinematic chain includes a first robotic arm. The second kinematic chain includes a bar that supports the first robotic arm.

In some embodiments, activating the automatic movement of the second kinematic chain relative to a physical environment of the robotic medical system includes starting a translational movement of the second kinematic chain relative to a base of the robotic medical system.

In some embodiments, the preset criteria are met in accordance with a determination that the first data corresponding to the manual manipulation of the first kinematic chain has exceeded a preset cutoff limit for more than a threshold amount of time.

In some instances, the threshold amount of time is at least two seconds.

In some instances, the threshold amount of time may be adjusted to anywhere from one to five seconds.

In some embodiments, the method includes: after activating the automatic movement of the second kinematic chain relative to the physical environment of the robotic medical system, receiving updated first data corresponding to additional manual movement of the first kinematic chain. The method further includes in accordance with a determination that the updated first data corresponding to the additional manual movement of the first kinematic chain does not meet the preset criteria, stopping the automatic movement of the second kinematic chain relative to the physical environment of the robotic medical system.

In some embodiments, the additional manual movement of the first kinematic chain causes reversal of the movement of the first kinematic chain along the length of the second kinematic chain.

In some embodiments, the first data includes a user input of a first type that is continuously maintained during the manual manipulation of the first kinematic chain. The updated first data includes cessation of the user input of the first type.

In some embodiments, the preset criteria require that the manual manipulation of the first kinematic chain is carried out in accordance with direct physical manipulation of the first kinematic chain by a user under a first power-assisted manipulation mode of the first kinematic chain.

In some embodiments, the robotic system further includes a third kinematic chain that is movably coupled to the second kinematic chain. The method further includes: in accordance to the automatic movement of the second kinematic chain, controlling movement of the third kinematic chain.

In some embodiments, the manual movement of the first kinematic chain along the second kinematic chain is constrained by a first limit along the second kinematic chain.

Note that the various embodiments described above can be combined with any other embodiments described herein.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 15 illustrates an exemplary instrument driver.

FIG. 29 illustrates a flowchart diagram of a method for setting up a robotic medical system according to some embodiments.

FIGS. 30A-30C illustrates a flowchart diagram for a method for setting up a robotic medical system according to some embodiments.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other embodiments of the disclosed concepts are possible, and various advantages can be achieved with the disclosed embodiments. Headings are included herein for reference and to aid in locating various sections. These headings are not intended to limit the scope of the concepts described with respect thereto. Such concepts may have applicability throughout the entire specification.

A. Robotic System—Cart.

Figure 1:
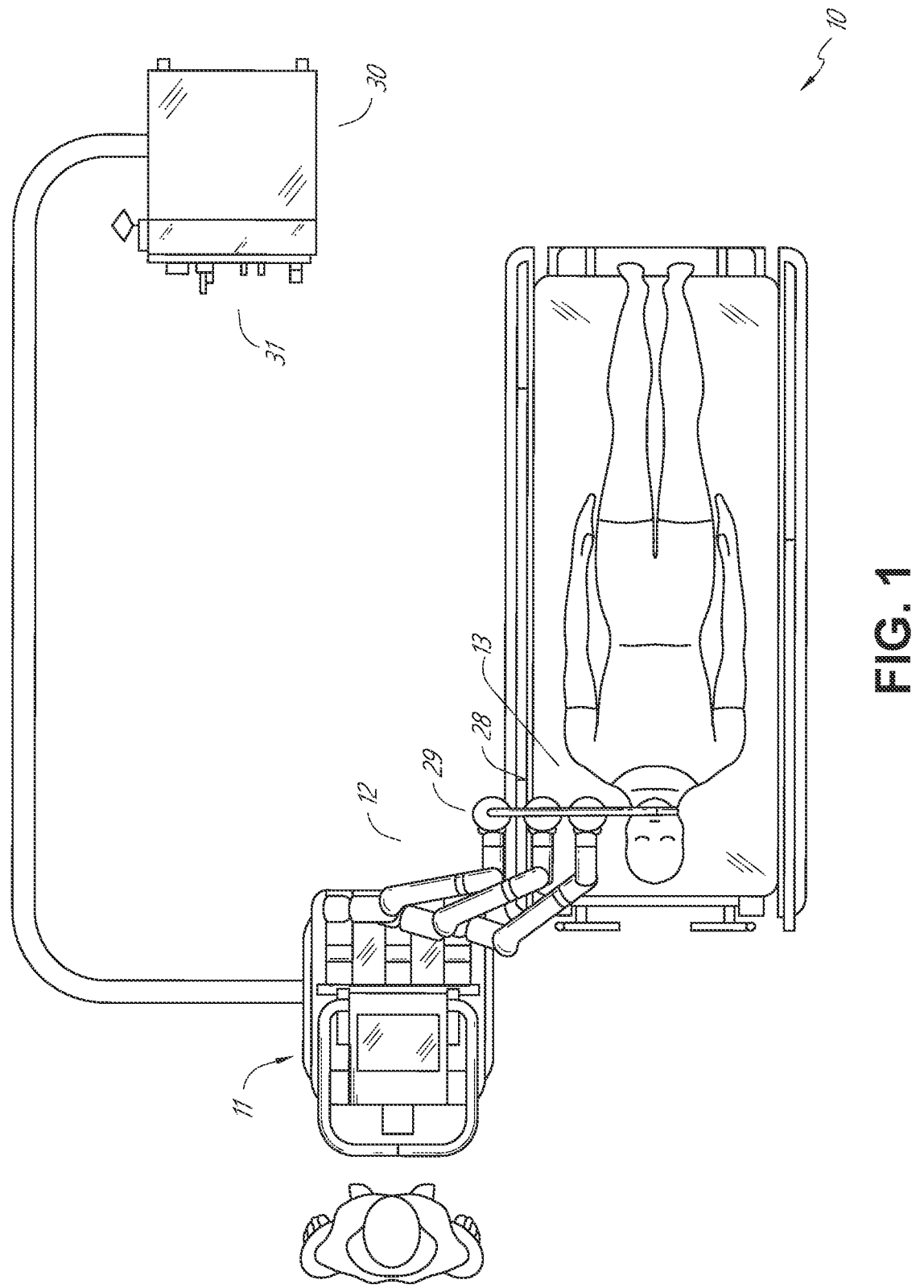
FIG. 1 illustrates an embodiment of a cart-based robotic system arranged for diagnostic and/or therapeutic bronchoscopy procedure(s).
Figure 2:
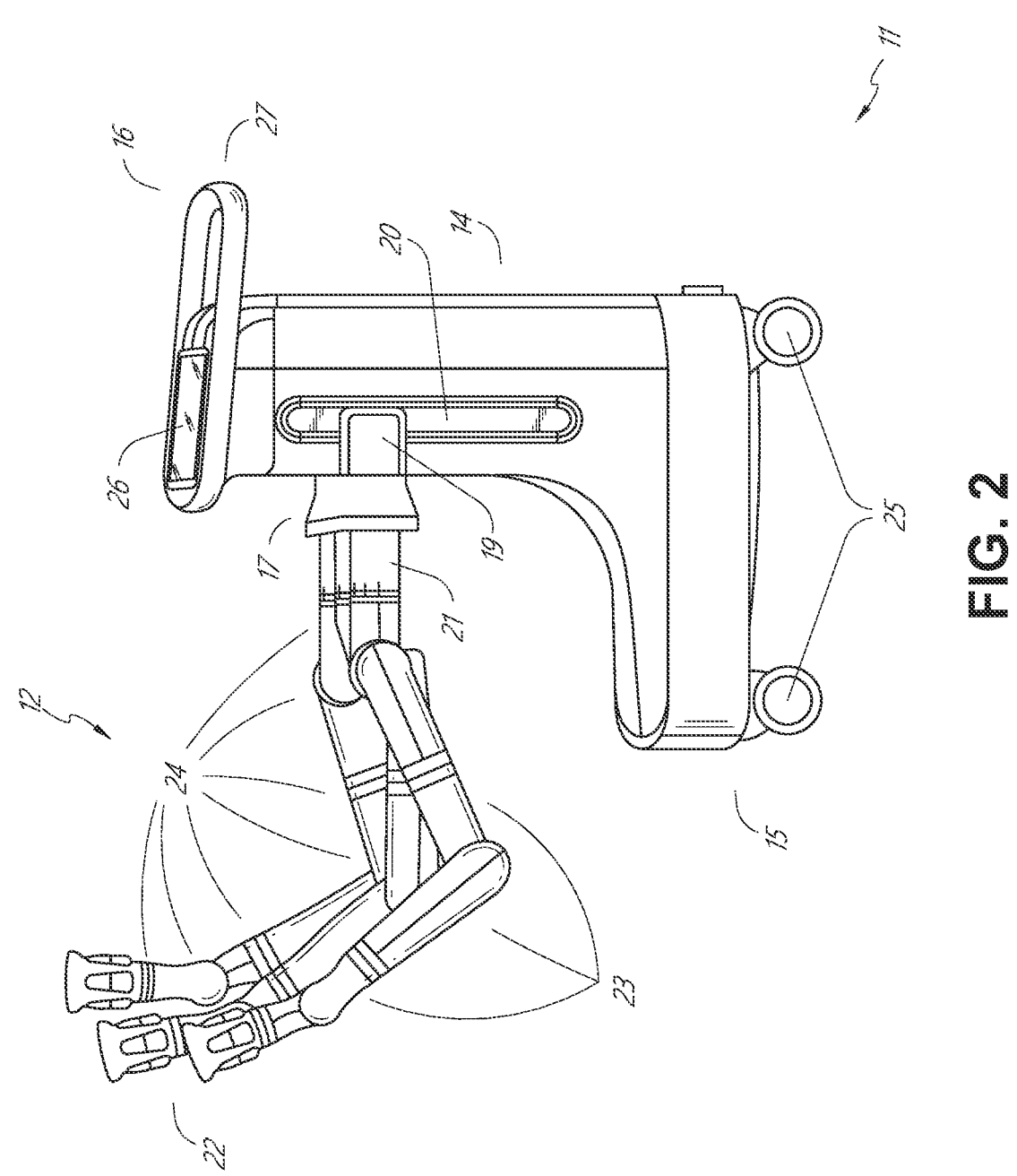
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart

11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
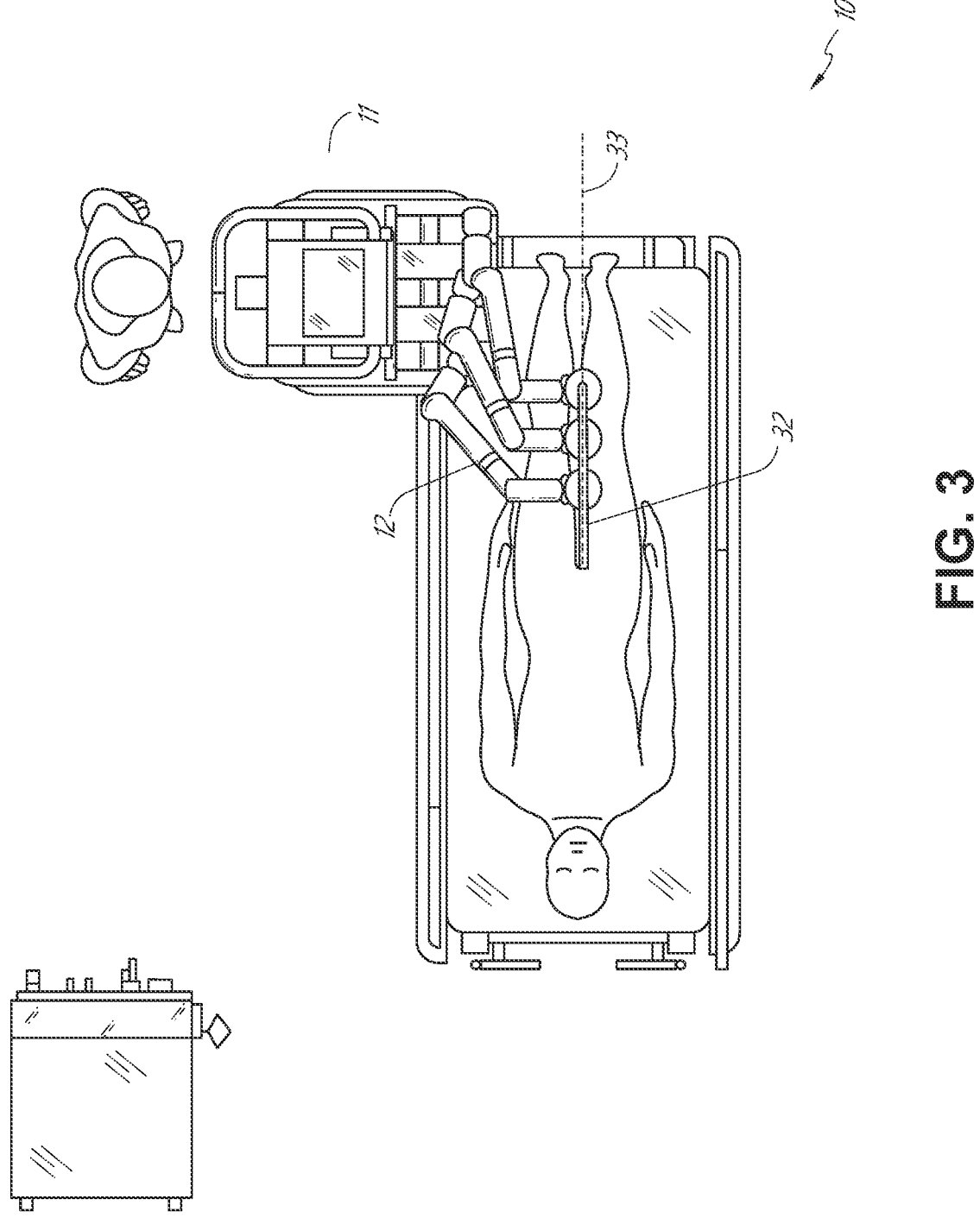
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
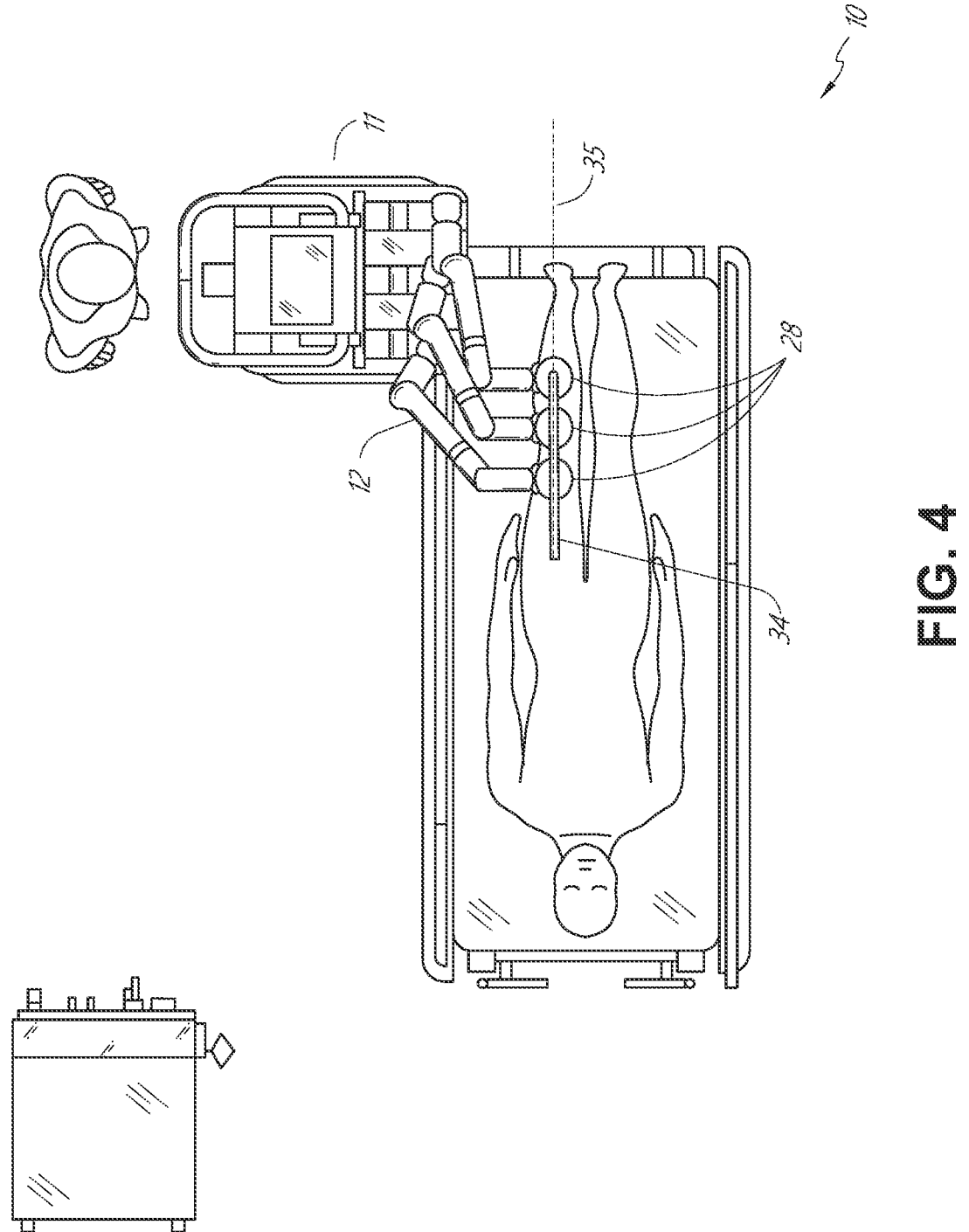
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
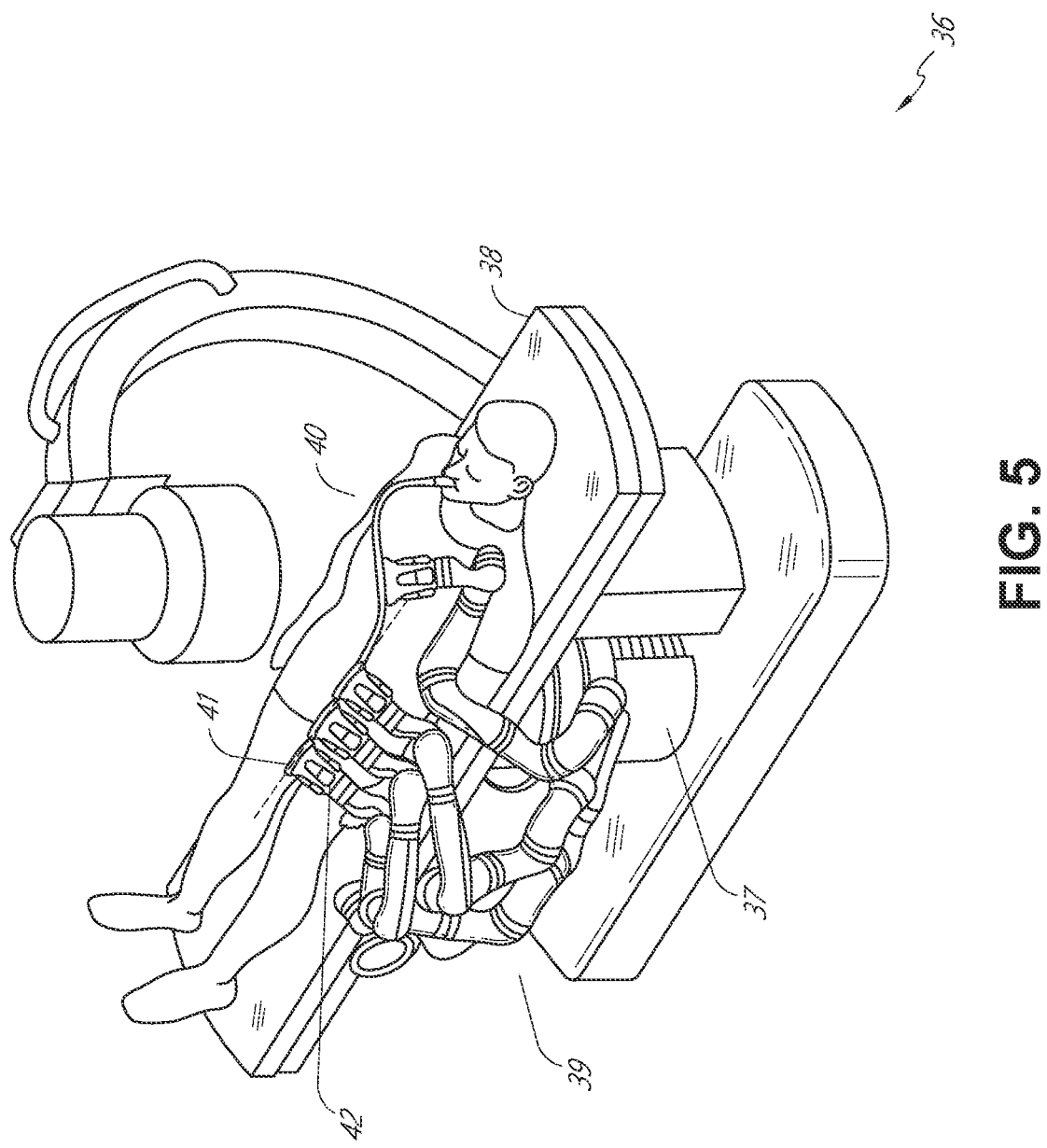
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
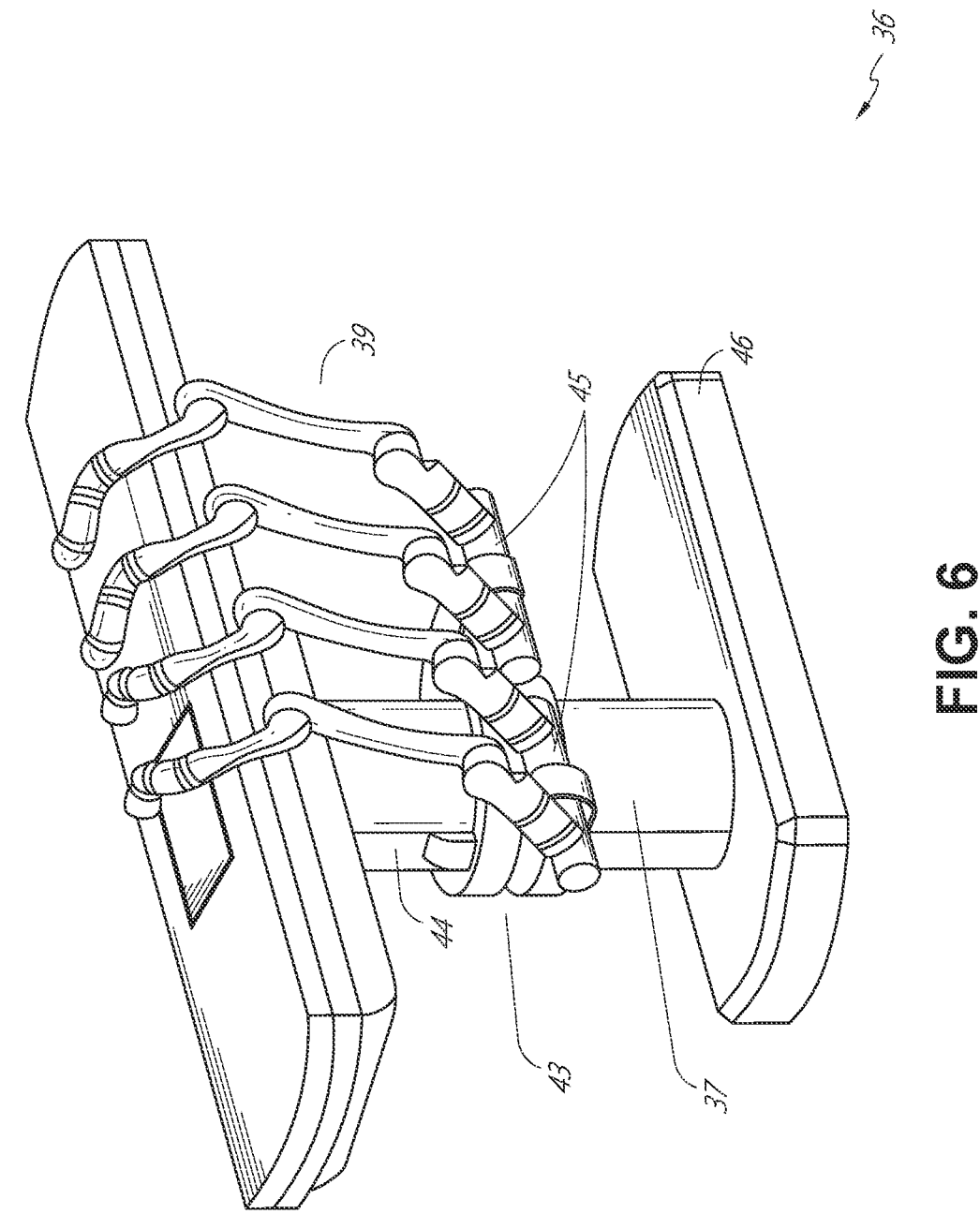
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
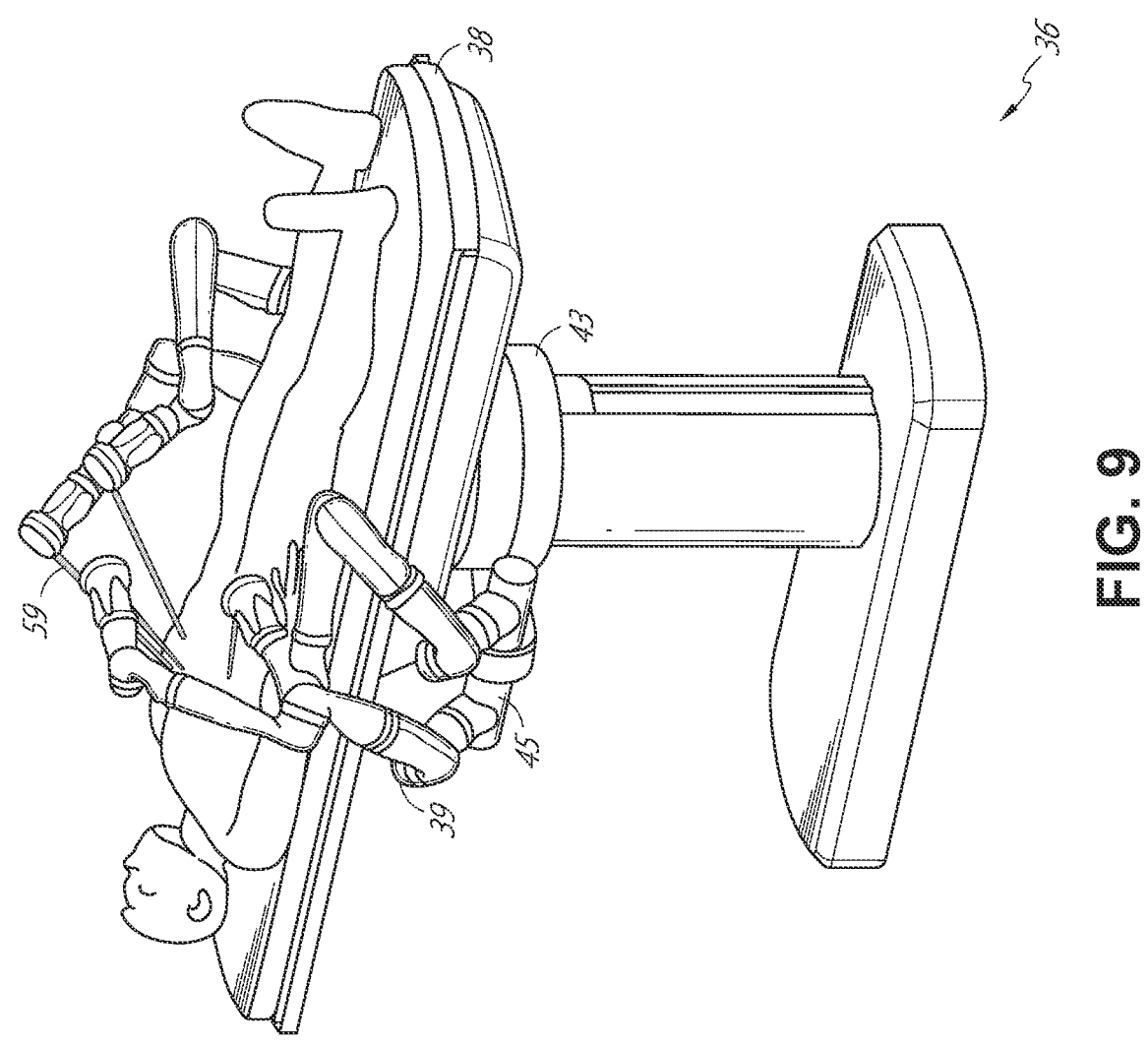
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
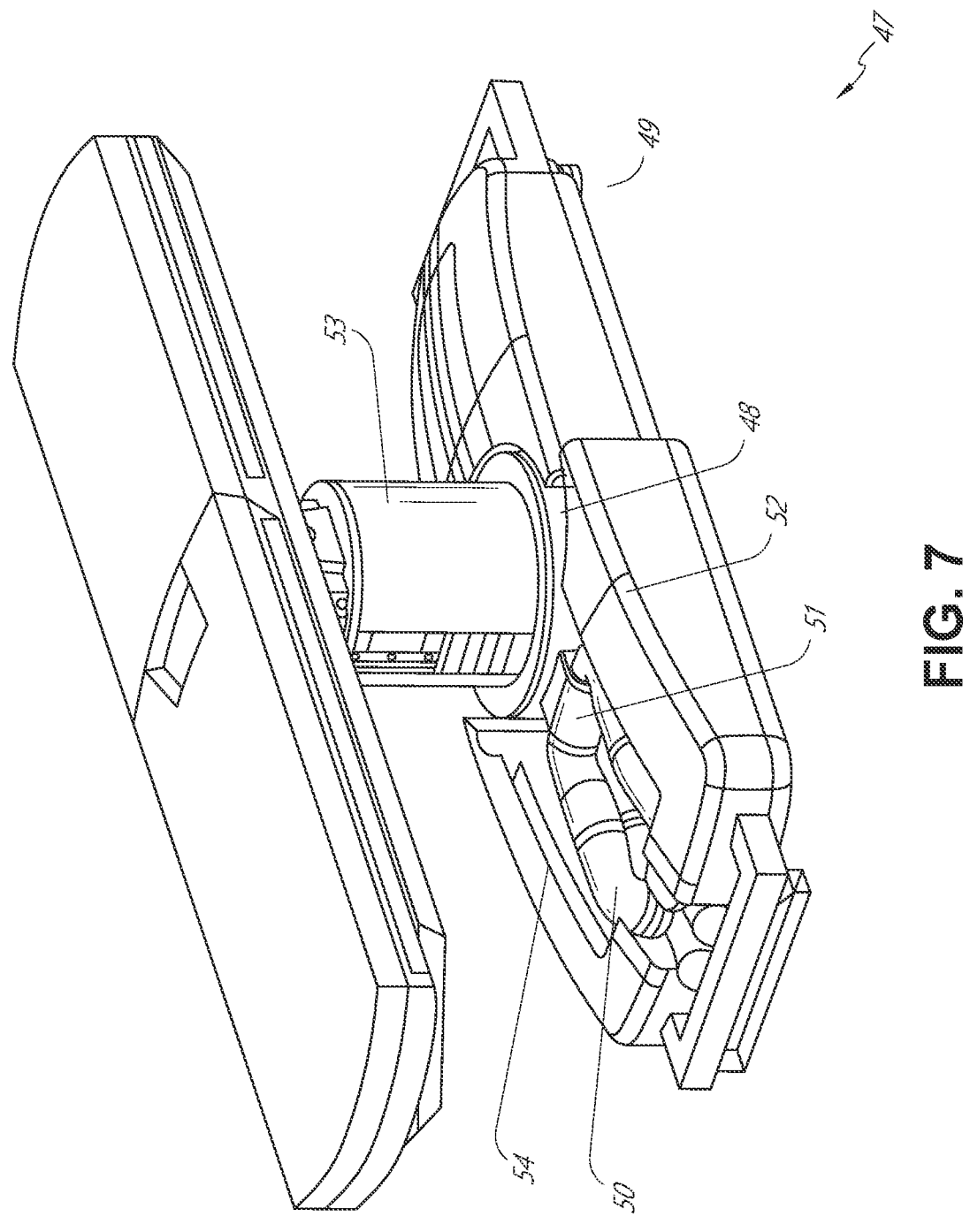
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
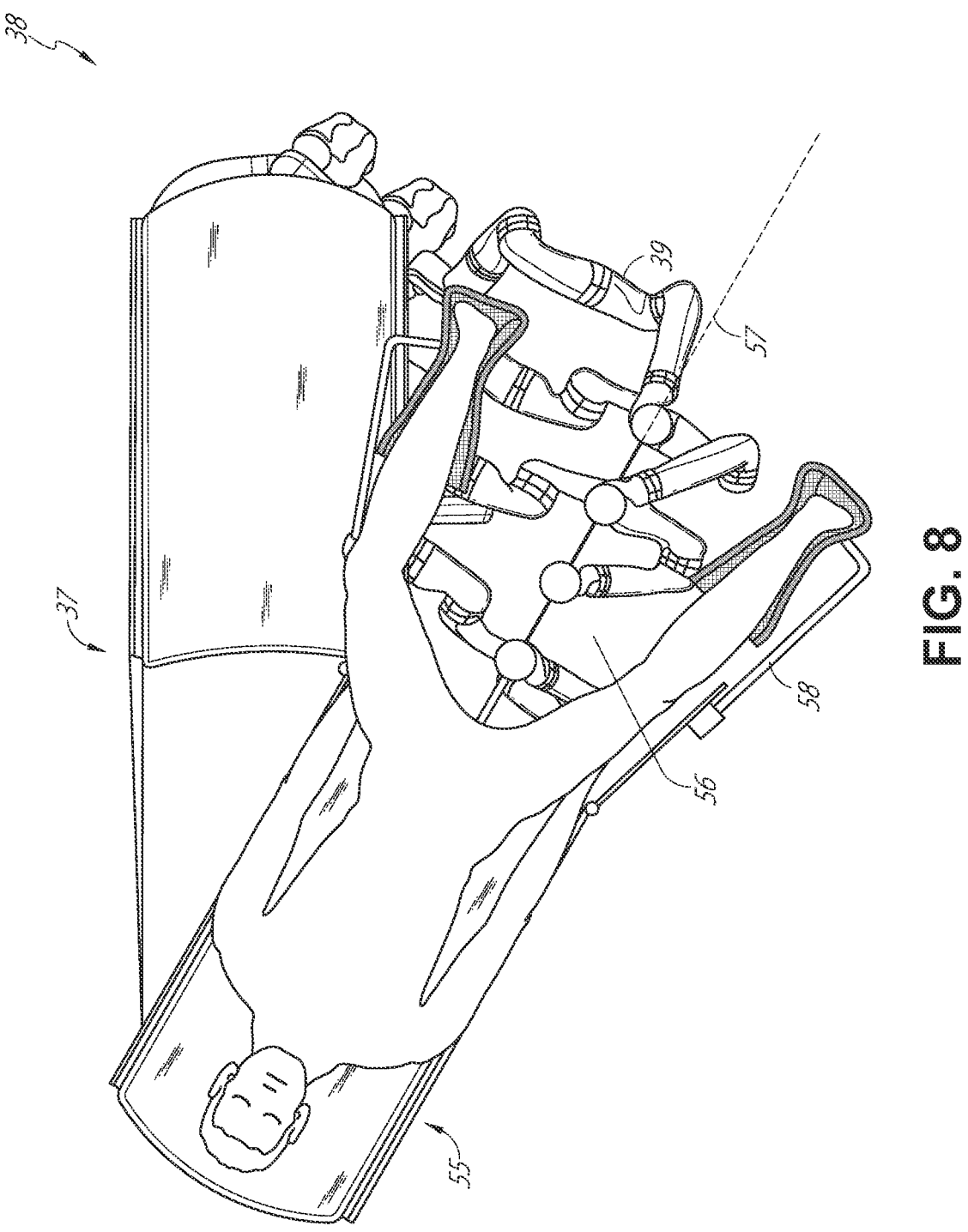
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
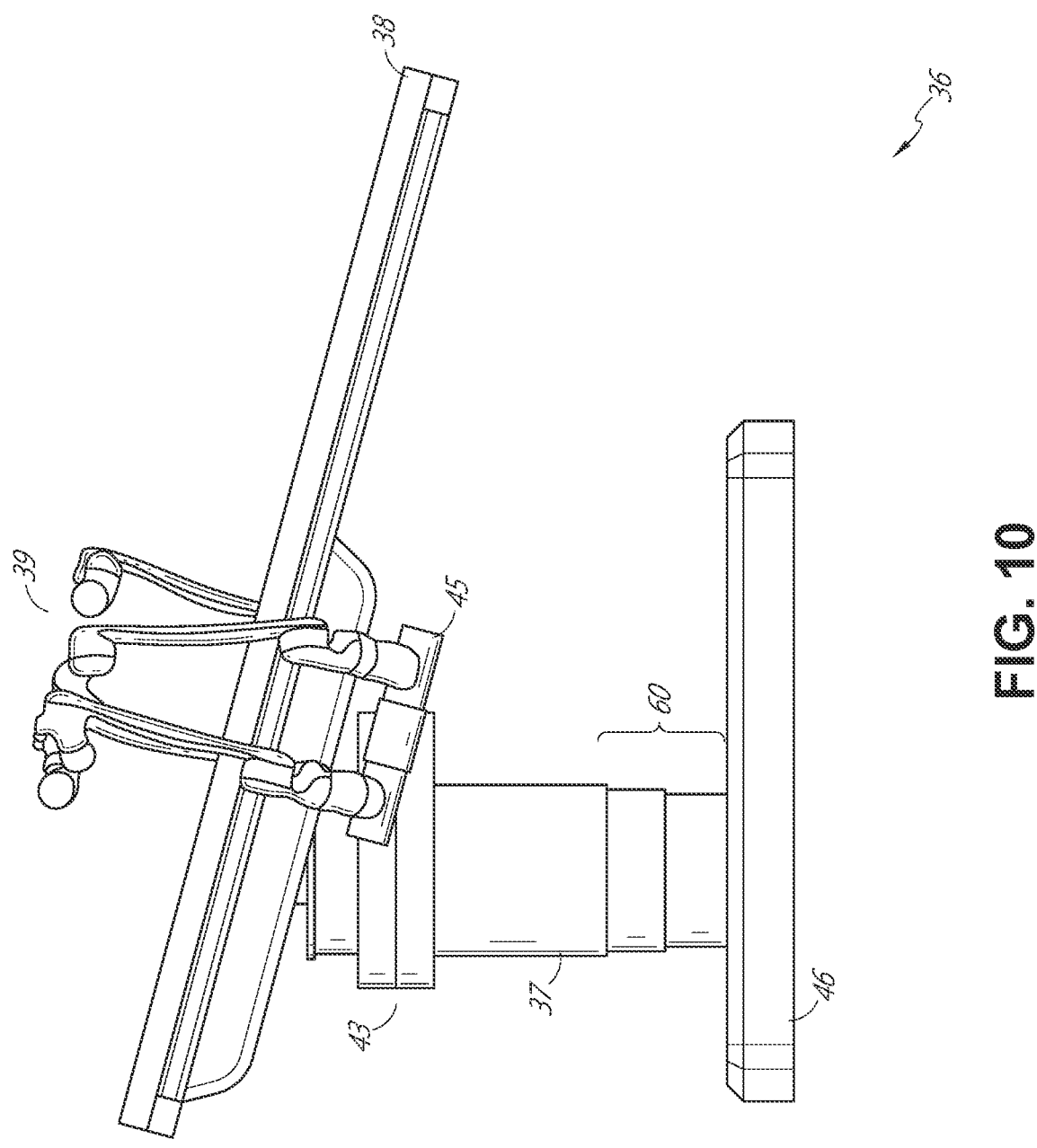
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
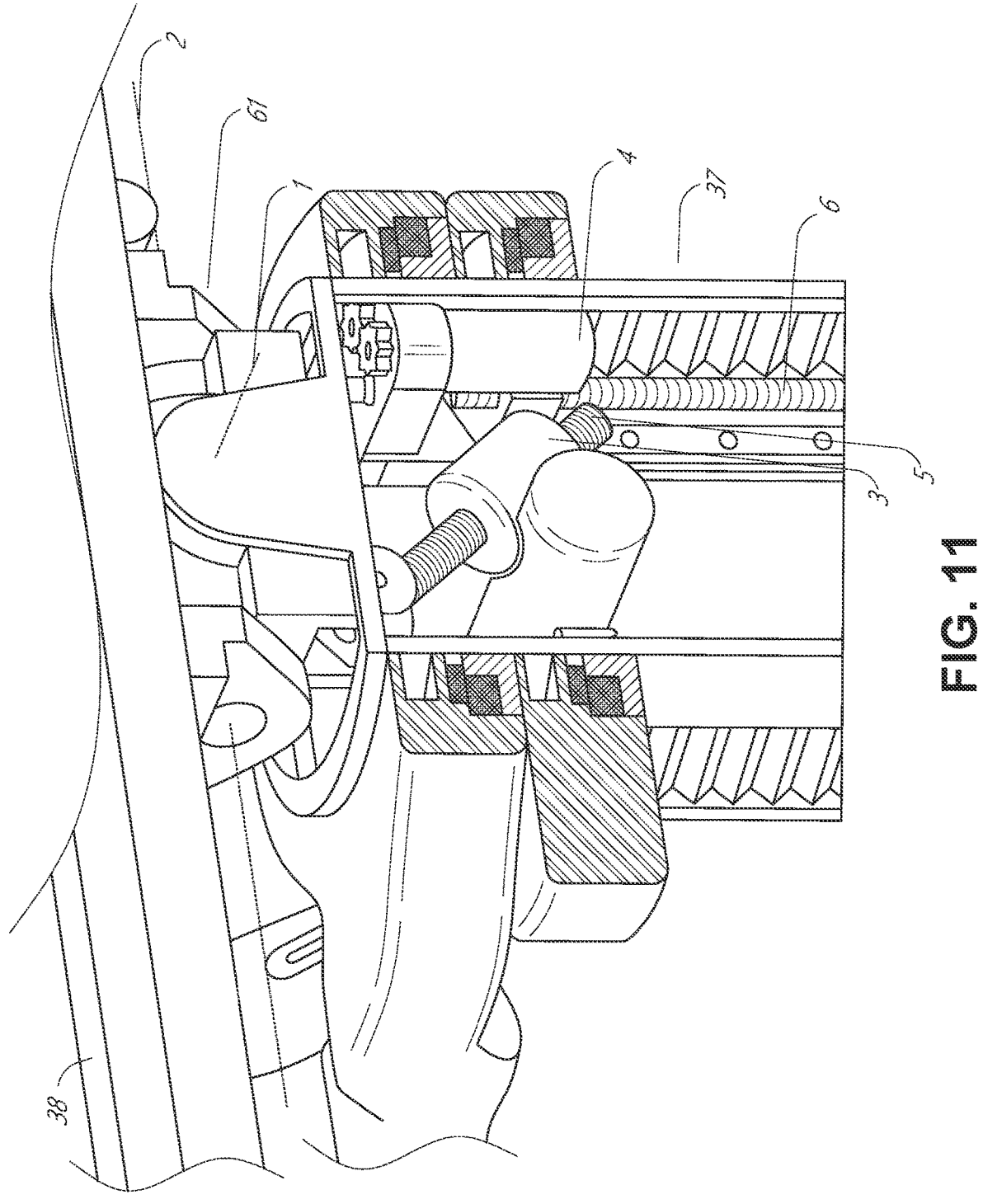
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
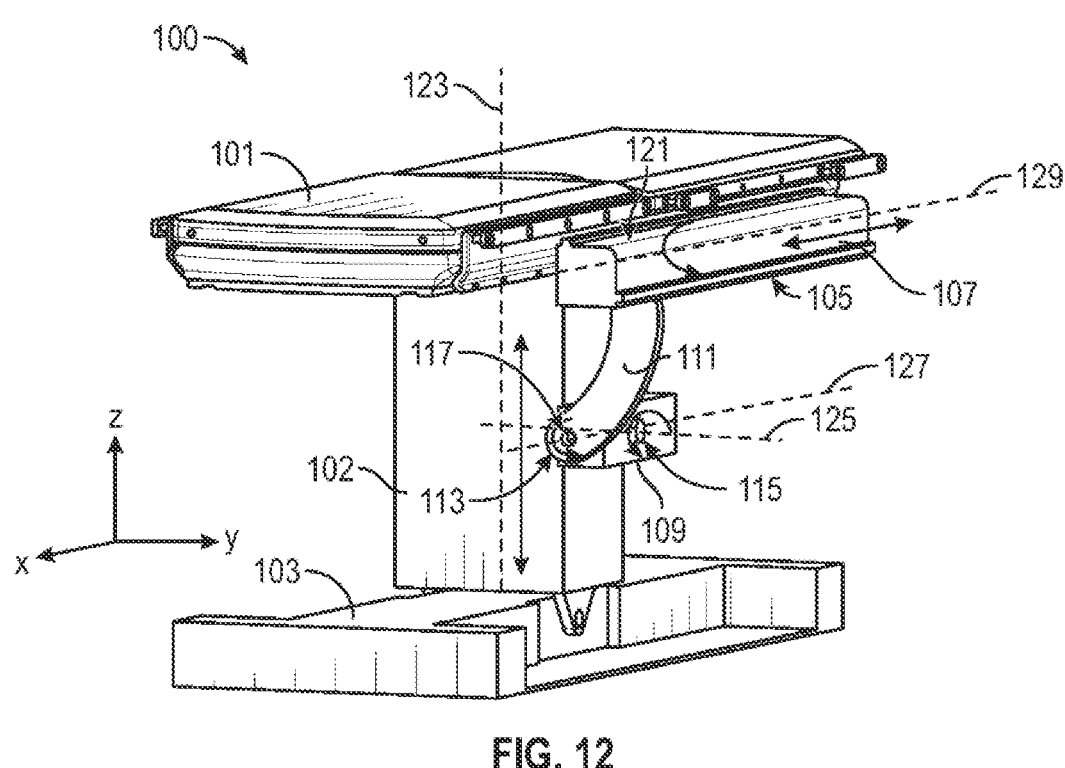
FIG. 12 illustrates an alternative embodiment of a table-based robotic system.
Figure 13:
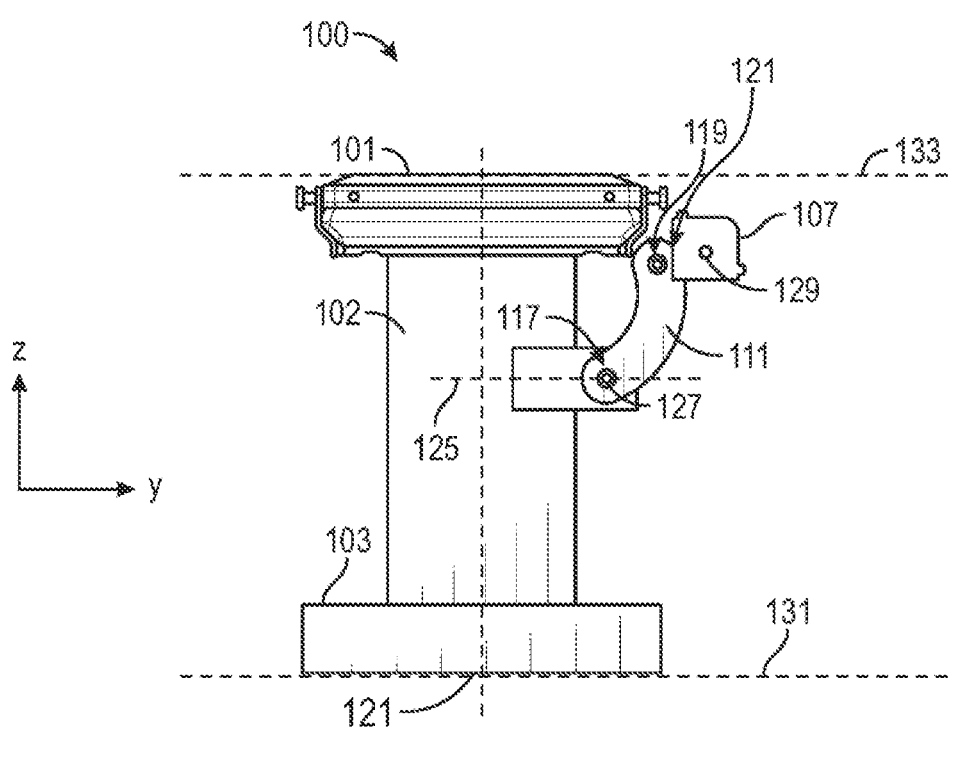
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
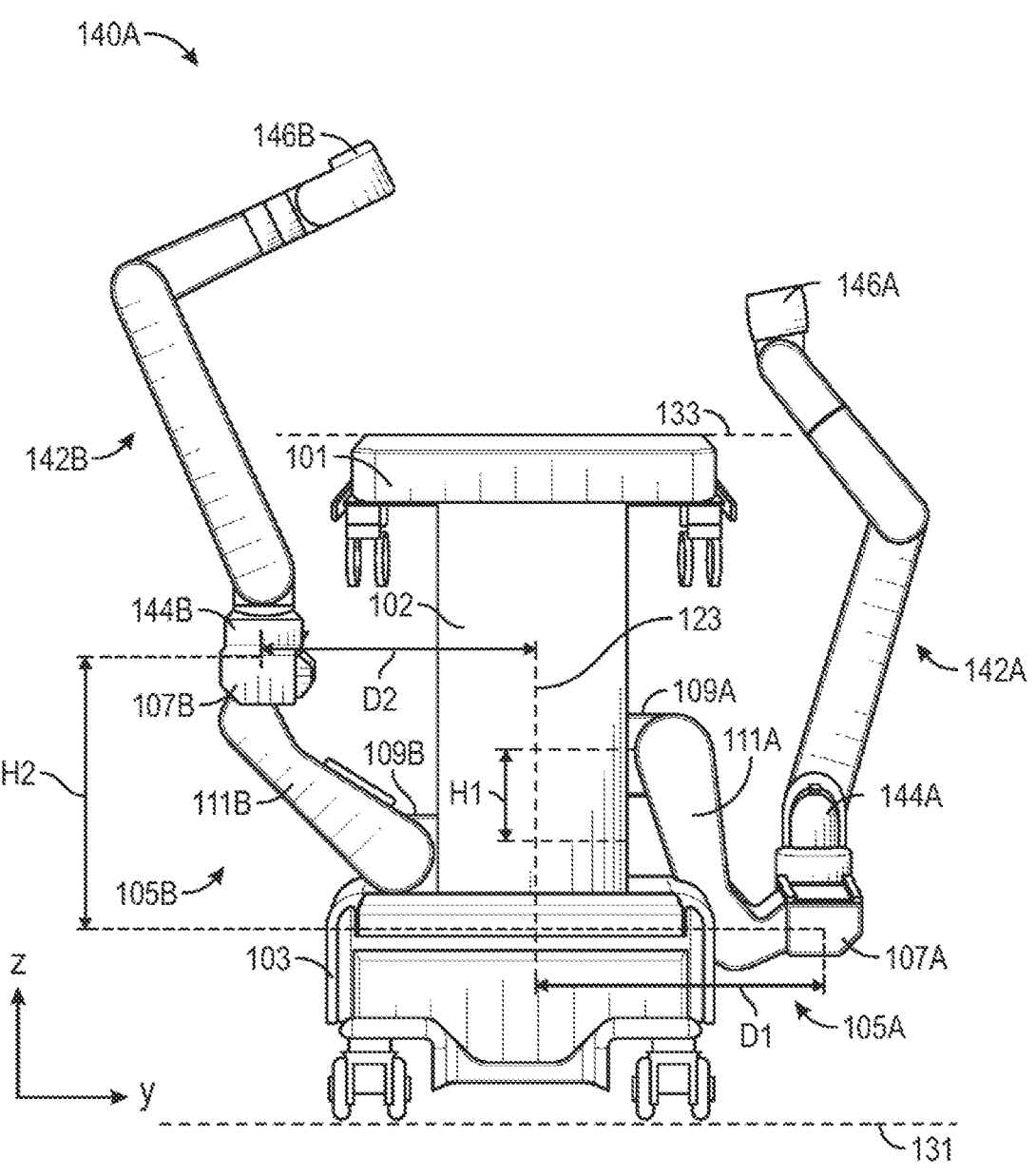
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B includes an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

FIG. 15 illustrates an example instrument driver. Positioned at the distal end of a robotic arm, instrument driver 62 includes one or more drive units 63 arranged with parallel axes to provide controlled torque to a medical instrument via drive shafts 64. Each drive unit 63 includes an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
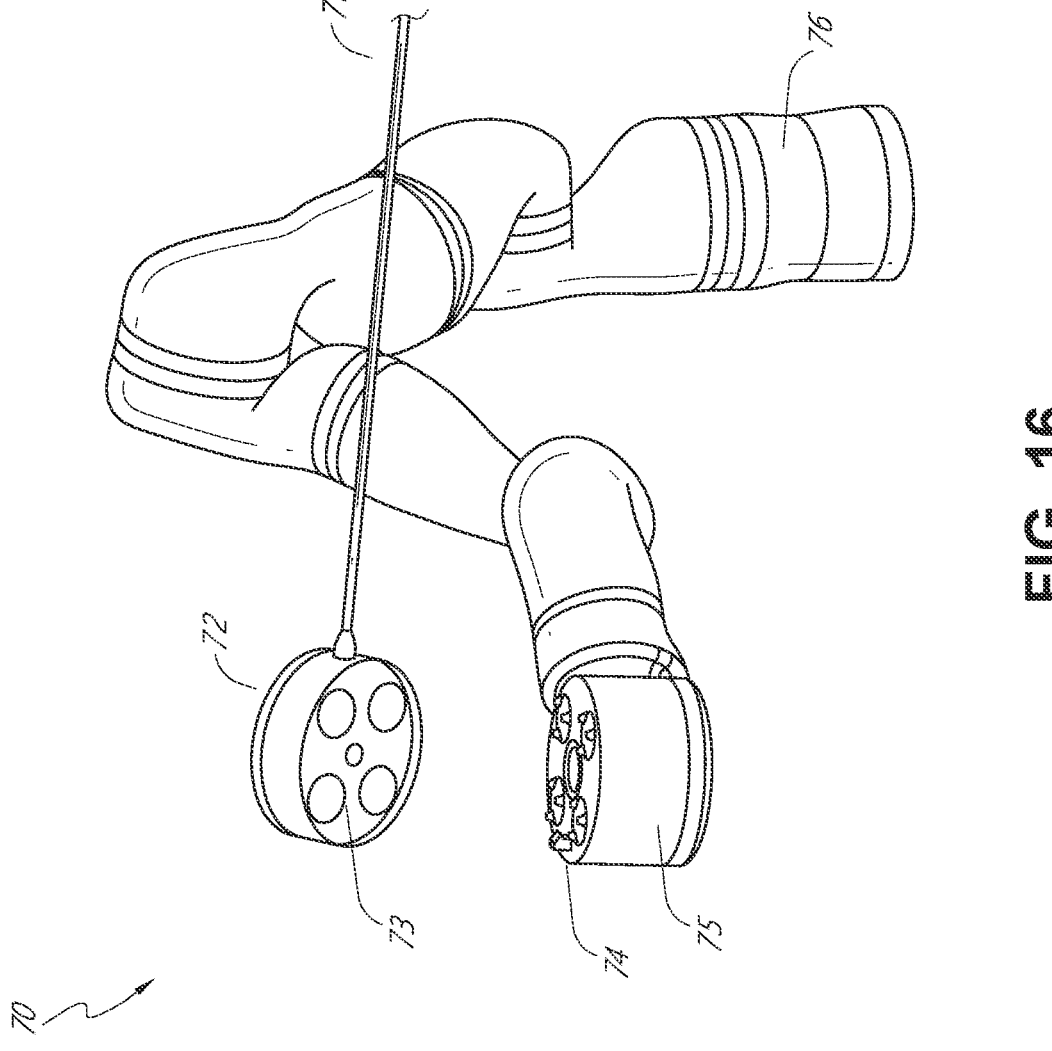
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
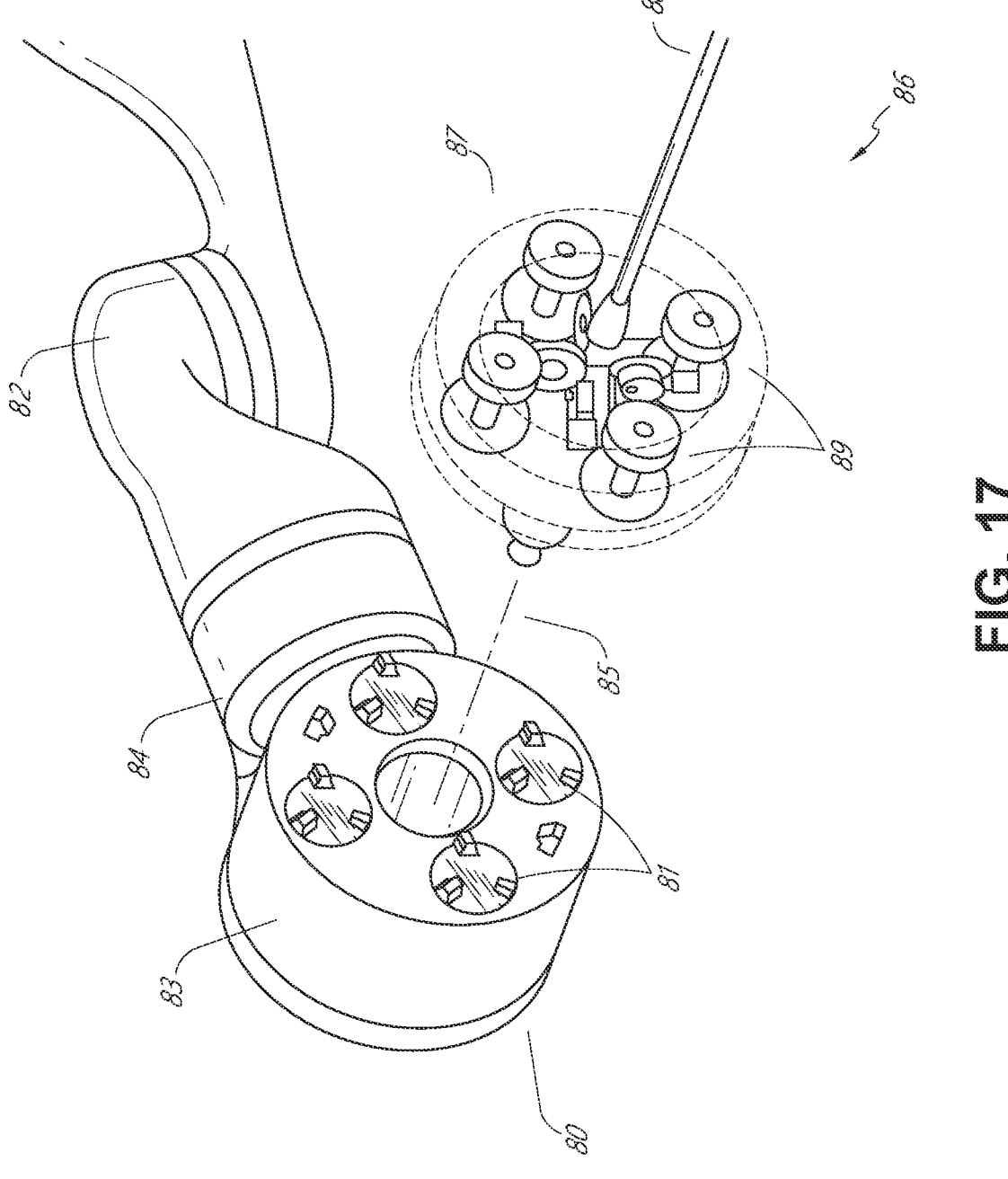
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
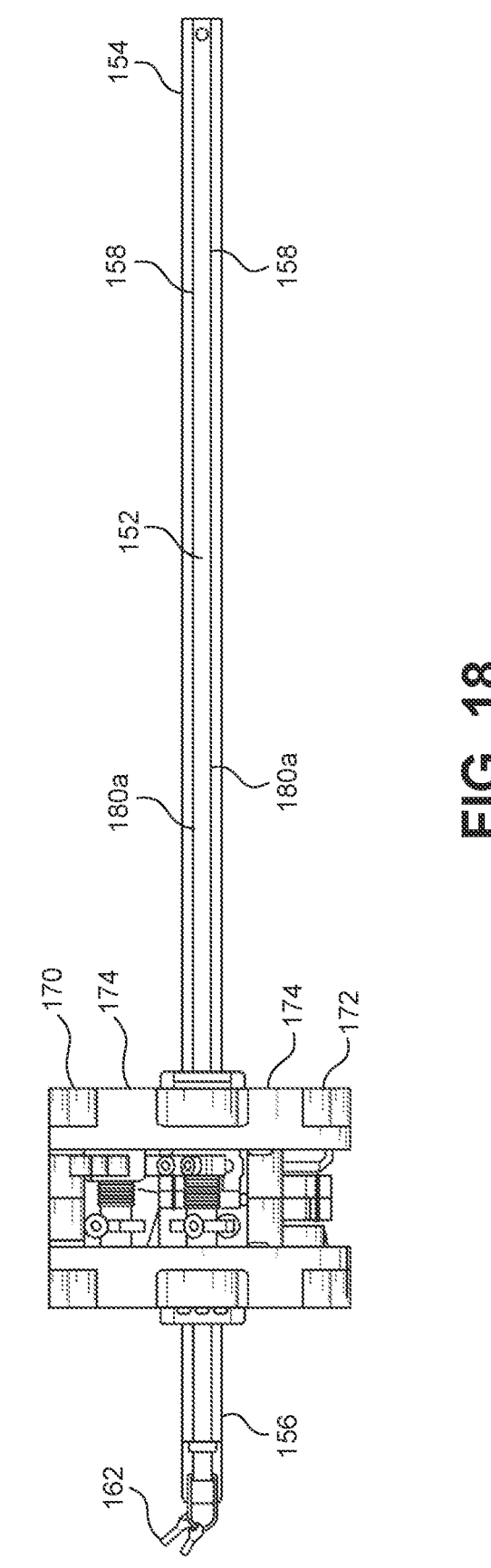
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
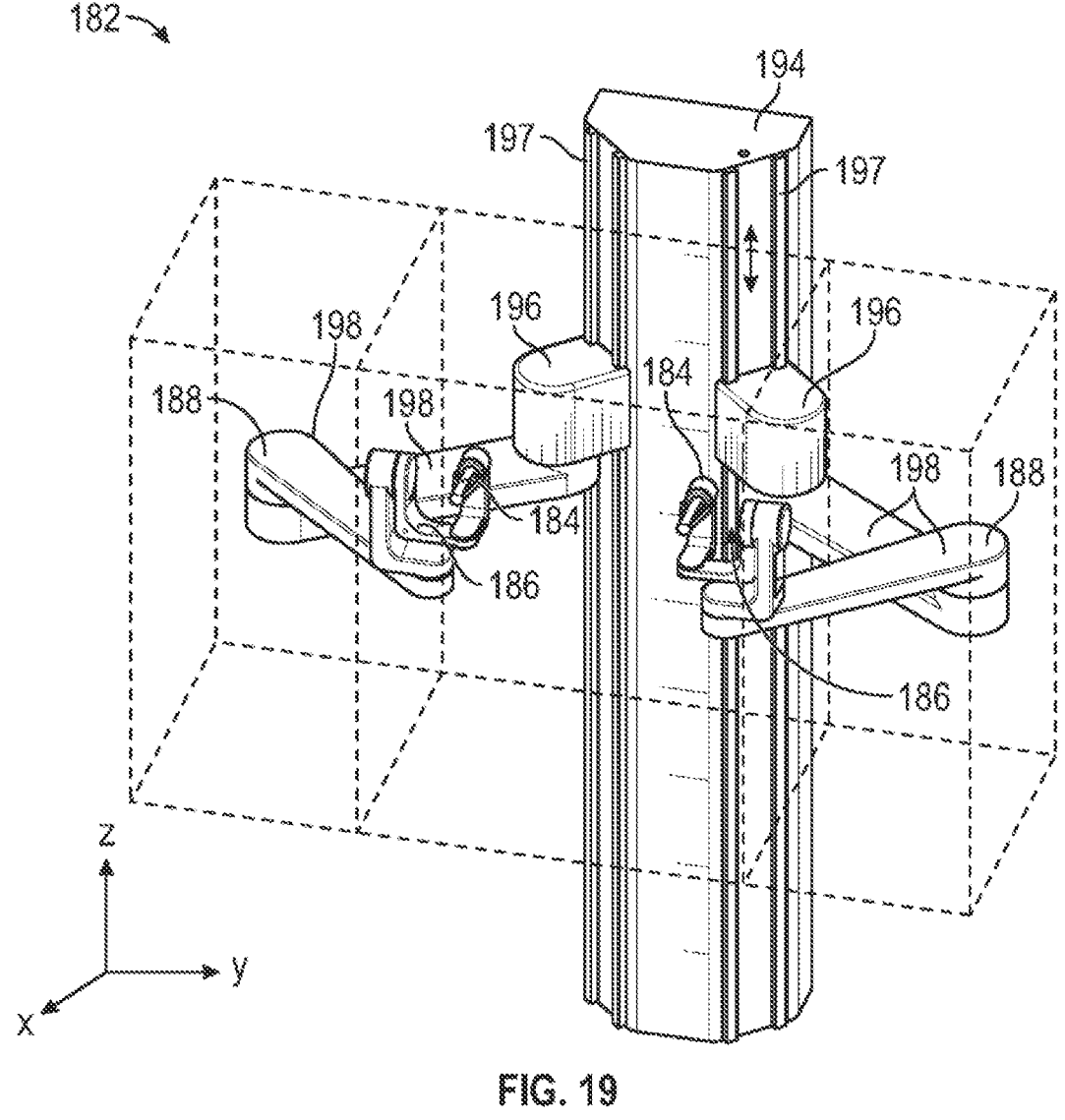
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
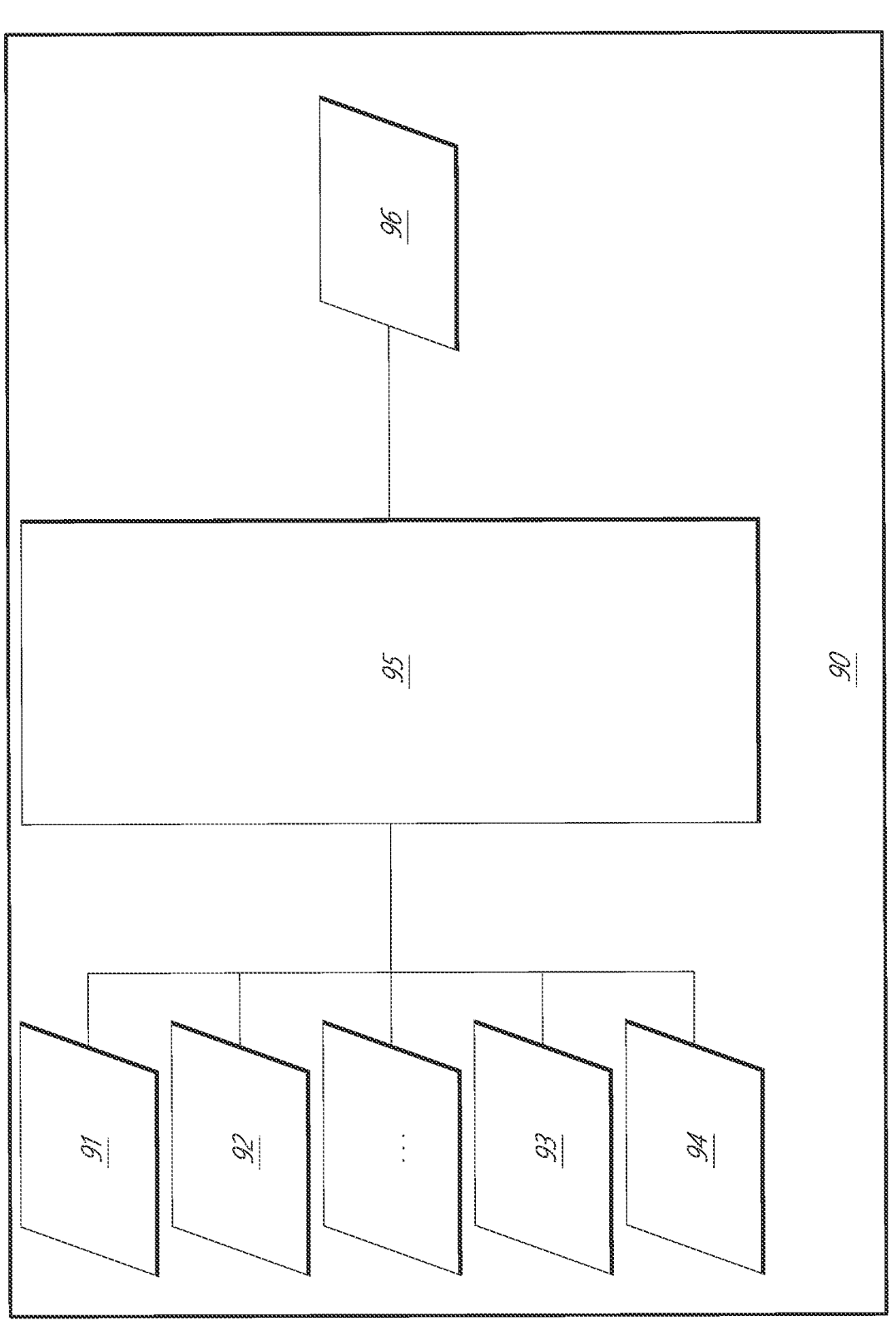
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data

91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Systems, Devices, and Methods for Controlling Motion of Kinematic Chains

Aspects of the present disclosure relates to systems, devices, and methods for controlling motion of multiple kinematic chains, including commanding bar translation while manipulating robotic arms (e.g., in a manual manipulation mode).

A robotically-enabled medical system may include robotic arms that are supported on an underlying bar (e.g., an adjustable arm support). Before a surgical procedure, a user may be required to set up the robotic arms and bar to a desired configuration. In some circumstances, the user can move one or more robotic arms (e.g., directly) to a desired set-up position but will have to rely on a controller to manipulate the underlying bar. Embodiments of the disclosure advantageously relate to systems, devices, and techniques to automatically move the underlying bar while the user is manipulating the one or more robotic arms, to make the setup process easier and faster.

A. Robotic System

Figure 21:
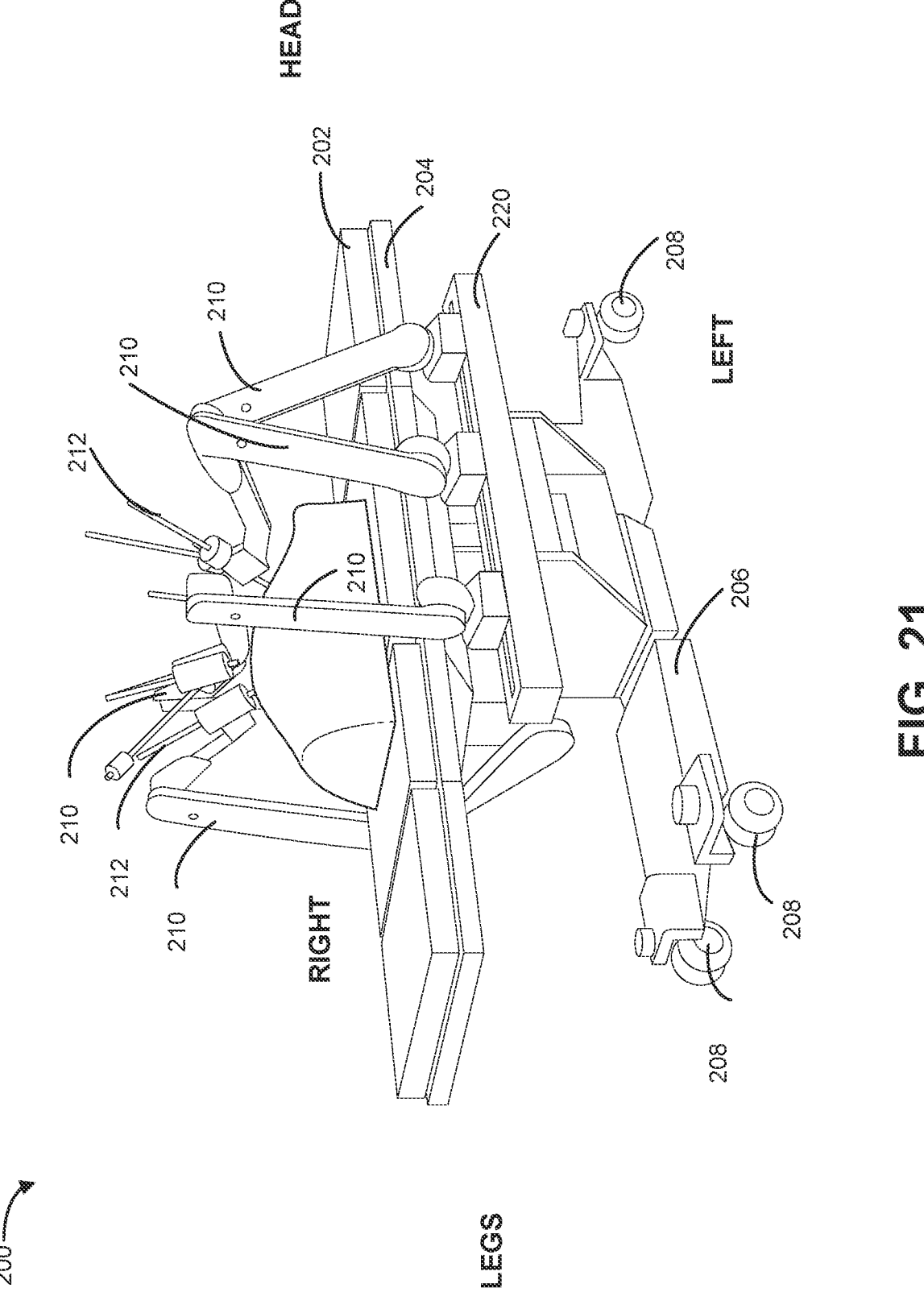
FIG. 21 illustrates an exemplary robotic system according to some embodiments.

FIG. 21 illustrates an exemplary robotic system 200 according to some embodiments. In some embodiments, the robotic system 200 is a robotic medical system (e.g., robotic surgery system). In the example of FIG. 21, the robotic system 200 includes a patient support platform 202 (e.g., a patient platform, a table, a bed, etc.). The two ends along the length of the patient support platform 202 are respectively referred to as "head" and "leg". The two sides of the patient support platform 202 are respectively referred to as "left" and "right." The patient support platform 202 includes a support 204 (e.g., a rigid frame) for the patient support platform 202.

The robotic system 200 also includes a base 206 for supporting the robotic system 200. The base 206 includes wheels 208 that allow the robotic system to be easily movable or repositionable in a physical environment. In some embodiments, the wheels 208 are omitted from the robotic system 200 or are retractable and the base 206 can rest directly on the ground or floor. In some embodiments, the wheels 208 are replaced with feet.

The robotic system 200 includes one or more robotic arms 210. The robotic arms 210 can be configured to perform one or more robotic medical procedures as described above with reference to FIGS. 1-20. Although FIG. 21 shows five robotic arms 210, it should be appreciated that the robotic system 200 may include any number of robotic arms.

The robotic system 200 also includes one or more bars 220 (e.g., adjustable arm support or an adjustable bar) that support the robotic arms 210. Each of the robotic arms 210 is supported on, and movably coupled to, a bar 220, by a respective base joint of the robotic arm. In some embodiments, and as described in FIG. 12, bar 220 can provide several degrees of freedom, including lift, lateral translation, tilt, etc. In some embodiments, each of the robotic arms 210 and/or the adjustable arm supports 220 is also referred to as a respective kinematic chain.

FIG. 21 shows three robotic arms 210 supported by the bar 220 that is in the field of view of the figure. The two remaining robotic arms are supported by another bar that is located across the other length of the patient support platform 202.

In some embodiments, the adjustable arm supports 220 can be configured to provide a base position for one or more of the robotic arms 210 for a robotic medical procedure. A robotic arm 210 can be positioned relative to the patient support platform 202 by translating the robotic arm 210 along a length of its underlying bar 220 and/or by adjusting a position and/or orientation of the robotic arm 210 via one or more joints and/or links (see, e.g., FIG. 23).

In some embodiments, the adjustable arm support 220 can be translated along a length of the patient support platform 202. In some embodiments, translation of the bar 220 along a length of the patient support platform 202 causes one or more of the robotic arms 210 supported by the bar 220 to be simultaneously translated with the bar or relative to the bar. In some embodiments, the bar 220 can be translated while keeping one or more of the robotic arms stationary with respect to the base 206 of the robotic medical system 200.

In the example of FIG. 21, the adjustable arm support 220 is located along a partial length of the patient support platform 202. In some embodiments, the adjustable arm support 220 may extend across an entire length of the patient support platform 202, and/or across a partial or full width of the patient support platform 202.

During a robotic medical procedure, one or more of the robotic arms 210 can also be configured to hold instruments 212 (e.g., robotically-controlled medical instruments or tools, such as an endoscope, a cannula, and/or any another instruments that may be used during surgery).

Figure 22:
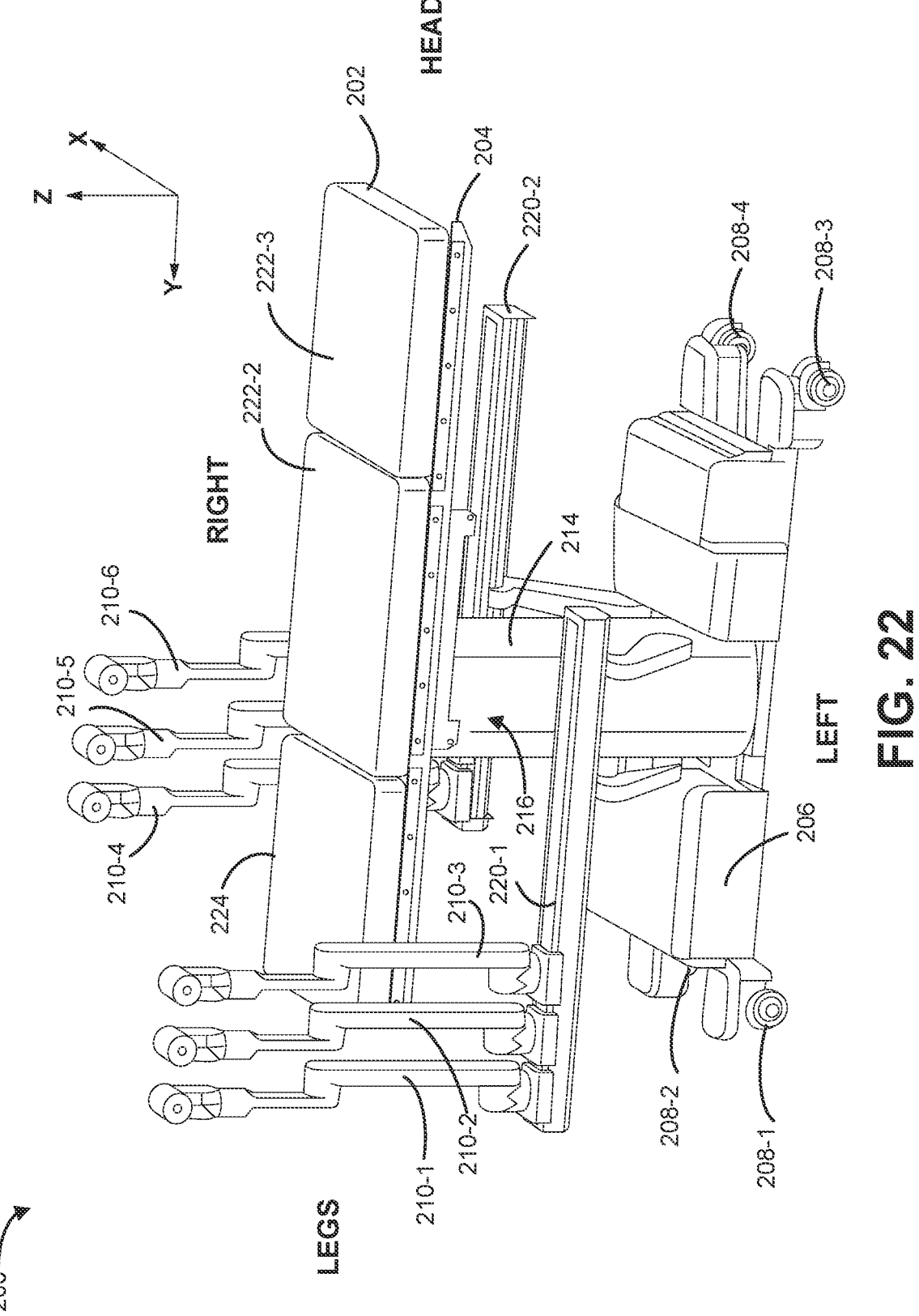
FIG. 22 illustrates another view of an exemplary robotic system according to some embodiments.

FIG. 22 illustrates another view of the exemplary robotic system 200 in FIG. 21 according to some embodiments. In this example, the robotic medical system 200 includes six robotic arms 210-1, 210-2, 210-3, 210-4, 210-5, and 210-6. The patient platform 202 is supported by a column 214 that extends between the base 206 and the patient platform 202. In some embodiments, the patient platform 202 includes a tilt mechanism 216. The tilt mechanism 216 can be positioned between the column 214 and the patient platform 202 to allow the patient platform to pivot, rotate, or tilt relative to the column 214. The tilt mechanism 216 can be configured to allow for lateral and/or longitudinal tilt of the patient platform 202. In some embodiments, the tilt mechanism 216 allows for simultaneous lateral and longitudinal tilt of the patient platform 202.

FIG. 22 shows the patient platform 202 in an untilted state or position. In some embodiments, the untilted state or position may be a default position of the patient platform 202. In some embodiments, the default position of the patient platform 202 is a substantially horizontal position as shown. As illustrated, in the untilted state, the patient platform 202 can be positioned horizontally or parallel to a surface that supports the robotic medical system 200 (e.g., the ground or floor).

With continued reference to FIG. 22, in the illustrated example of the robotic system 200, the patient platform 202 includes a support 204. In some embodiments, the support 204 includes a rigid support structure or frame, and can support one or more surfaces, pads, or cushions 222. An upper surface of the patient platform 202 can comprise a support surface 224. During a medical procedure, a patient can be placed on the support surface 224.

FIG. 22 shows the robotic arms 210 and the adjustable arm supports 220 in an exemplary deployed configuration in which the robotic arms 210 reach above the patient platform 202. In some embodiments, due to the configuration of the robotic system 200, which enables stowage of different components beneath the patient platform 202, the robotic arms 210 and the arm supports 220 can occupy a space underneath the patient platform 202. Thus, in some embodiments, it may be advantageous to configure the tilt mechanism 216 to have a low-profile and/or low volume to maximize the space available for storage below.

FIG. 22 also illustrates an example, x, y, and z coordinate system that will be used to describe certain features of the embodiments disclosed herein. It will be appreciated that this coordinate system is provided for purposes of example and explanation only and that other coordinate systems may be used. In the illustrated example, the x-direction or x-axis extends in a lateral direction across the patient platform 202 when the patient platform 202 is in an untilted state. That is, the x-direction extends across the patient platform 202 from one lateral side (e.g., the right side) to the other lateral side (e.g., the left side) when the patient platform 202 is in an untilted state. The y-direction or y-axis extends in a longitudinal direction along the patient platform 202 when the patient platform 202 is in an untilted state. That is, the y-direction extends along the patient platform 202 from one longitudinal end (e.g., the head end) to the other longitudinal end (e.g., the legs end) when the patient platform 202 is in an untilted state. In an untilted state, the patient platform 202 can lie in or be parallel to the x-y plane, which can be parallel to the floor or ground. In the illustrated example, the z-direction or z-axis extends along the column 214 in a vertical direction. In some embodiments, the tilt mechanism 216 is configured to laterally tilt the patient platform 202 by rotating the patient platform 202 about a lateral tilt axis that is parallel to the y-axis. The tilt mechanism 216 can further be configured to longitudinally tilt the patient platform 202 by rotating the patient platform 202 about a longitudinal tilt axis that is parallel to the x-axis.

B. Robotic Arm

Figure 23B:
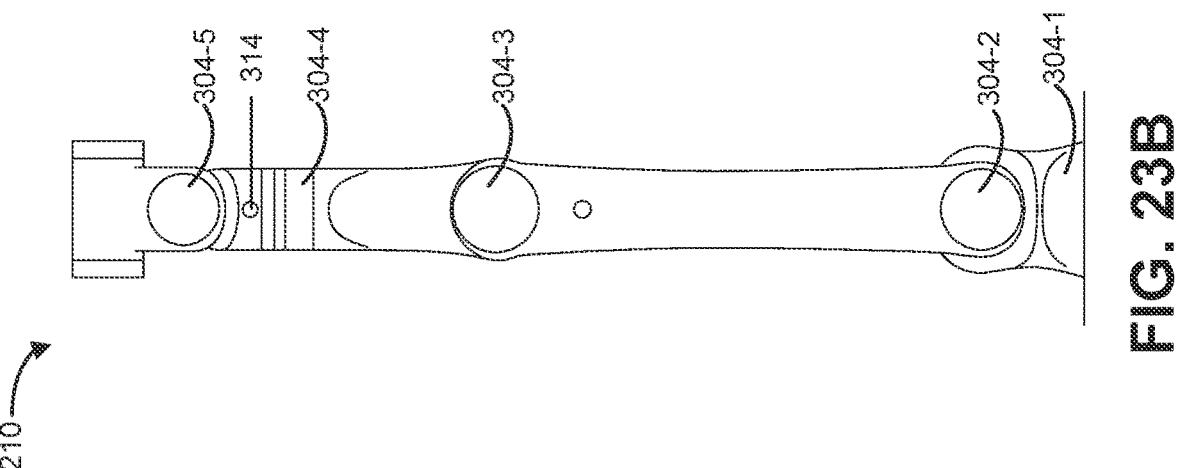
FIGS. 23A and 23B illustrate, respectively, a side view and a front view of an exemplary robotic arm according to some embodiments.
Figure 23A:
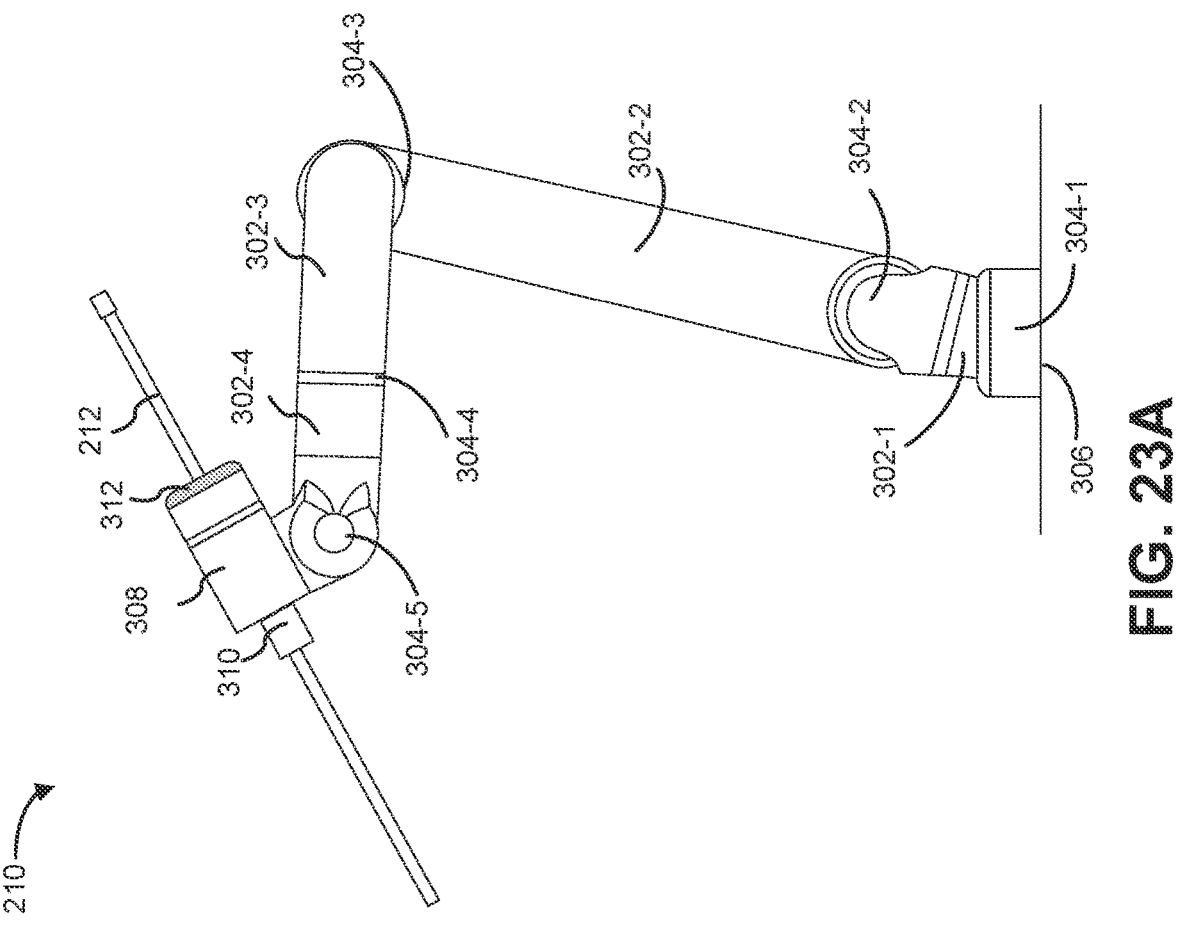

FIGS. 23A and 23B illustrate, respectively, a side view and a front view of an exemplary robotic arm 210 according to some embodiments.

FIG. 23A illustrates that the robotic arm 210 includes a plurality of links 302. The links 302 are connected by one or more joints 304. Each of the joints 304 includes one or more degrees of freedom (DoFs). In FIG. 23A, the joints 304 include a first joint 304-1 (e.g., a base joint or A0 joint) that is located at or near the base 306. In some embodiments, the base joint 304-1 includes a prismatic joint that allows the robotic arm 210 to translate along the bar 220. In some embodiments, the joints 304 also include a second joint 304-2 that enables the link 302-2 to tilt and/or rotate, an elbow joint (e.g., A3 joint) 304-3 that connects two links (e.g., the links 302-2 and 302-3), and a pair of joints 304-4 (e.g., a wrist roll joint or A4 joint) and 304-5 (e.g., a wrist pitch joint or A5 joint) that are located on a distal portion of the robotic arm 210.

A proximal end of the robotic arm 210 may be connected to a base 306 and a distal end of the robotic arm 210 may be connected to an advanced device manipulator (ADM) 308 (e.g., a tool driver or an end effector, etc.). The ADM 308 may be configured to control the positioning and manipulation of a medical instrument 212 (e.g., a tool, a scope, etc.).

In some embodiments, the robotic arm 210 includes one or more sensors. For example, the base joint 304-1 can comprise a force sensor for detecting force (e.g., axial force) of the robotic arm 210 along the bar 220. A load cell (e.g., a six-axis load cell) can be placed at or near the A4-A5 joints to detect and resolve forces and/or torques on an end effector 308. In some embodiments, contact sensors can be placed on (or in) one or more links 302 of the robotic arm 210 to detect forces on the links.

The robotic arm 210 can also include a cannula sensor 310 for detecting a docked state of the robotic arm 210. In some embodiments, the robotic arm 210 is placed in a docked state (e.g., docked position) when the cannula sensor 310 detects presence of a cannula (e.g., via one or more processors of the robotic system 200). In some embodiments, when the robotic arm 210 is in a docked position, the robotic arm 210 can execute null space motion to maintain a position and/or orientation of the cannula, as discussed in further detail below. Conversely, when no cannula is detected by the cannula sensor 310, the robotic arm 210 is placed in an undocked state (e.g., undocked position).

In some embodiments, and as illustrated in FIG. 23A, the robotic arm 210 includes a button 312 (e.g., a donut-shaped button, or other types of controls, etc.) that can be used to place the robotic arm 210 in an admittance mode. In the admittance mode, the robotic system 210 measures forces and/or torques and outputs corresponding velocities and/or positions. In some embodiments, the robotic arm 210 can be manually manipulated by a user (e.g., during a set-up procedure, or in between procedures, etc.) in the admittance mode.

In some embodiments, the links 302 may be detachably coupled to the medical tool 212 (e.g., to facilitate ease of mounting and dismounting of the medical tool 212 from the robotic arm 210). The joints 304 provide the robotic arm 210 with a plurality of degrees of freedom (DoFs) that facilitate control of the medical tool 212 via the ADM 308.

FIG. 23B illustrates a front view of the robotic arm 210. In some embodiments, the robotic arm 210 includes a button 314 (e.g., a push button) that is distinct from the button 312 in FIG. 23A, for placing the robotic arm in an impedance mode (e.g., by a single press or continuous press and hold of the button). In this example, the button 304 is located between the A4 joint 304-4 and the A5 joint 304-5. In the impedance mode, the robotic system 200 measures displacements (e.g., changes in position and velocity) and outputs forces to facilitate manual movement of the robotic arm. In some embodiments, the robotic arm 210 can be manually manipulated by a user (e.g., during a set-up procedure) in the impedance mode.

In some embodiments, the robotic arm 210 includes a single button that can be used to place the robotic arm 210 in the admittance mode and the impedance mode (e.g., by using different presses, such as a long press, a short press, press and hold etc.). In some embodiments, the robotic arm 210 can be placed in impedance mode by a user pushing on arm linkages (e.g., the links 302) and/or joints (e.g., the joints 304) and overcoming a force threshold.

During a medical procedure, it can be desirable to have the ADM 308 of the robotic arm 210 and/or a remote center of motion (RCM) of the tool 212 coupled thereto kept in a static pose/position. An RCM may refer to a point in space where a cannula or other access port through which a medical tool 212 is inserted is constrained in motion. In some embodiments, the medical tool 212 includes an end effector that is inserted through an incision or natural orifice of a patient while maintaining the RCM. In some embodiments, the medical tool 212 includes an end effector that is in a retracted state during a setup process of the robotic medical system.

In some circumstances, the robotic system 200 can be configured to move one or more links 302 of the robotic arm 210 within a "null space" to avoid collisions with nearby objects (e.g., other robotic arms) while the ADM 308 of the robotic arm 210 and/or the RCM are maintained in their respective poses/positions. The null space can be viewed as the space in which a robotic arm 210 can move that does not result in movement of the ADM 308 and/or RCM, thereby maintaining the position and/or the orientation of the medical tool 212 (e.g., within a patient). In some embodiments, a robotic arm 212 can have multiple positions and/or configurations available for each pose of the ADM 308.

For a robotic arm 210 to move the ADM 308 to a desired pose in space, in certain embodiments, the robotic arm 210 may have at least six DoFs—three DoFs for translation (e.g., X, Y, Z position) and three DoFs for rotation (e.g., yaw, pitch, and roll). In some embodiments, each joint 304 may provide the robotic arm 210 with a single DoF, and thus, the robotic arm 210 may have at least six joints to achieve freedom of motion to position the ADM 308 at any pose in space. To further maintain the ADM 308 of the robotic arm 210 and/or the remote center or motion in a desired pose, the robotic arm 210 may further have at least one additional "redundant joint." Thus, in certain embodiments, the system may include a robotic arm 210 having at least seven joints 304, providing the robotic arm 210 with at least seven DoFs. In some embodiments, the robotic arm 210 may include a subset of joints 304 each having more than one degree of freedom thereby achieving the additional DoFs for null space motion. However, depending on the embodiment, the robotic arm 210 may have a greater or fewer number of DoFs.

Furthermore, as described in FIG. 12, the bar 220 (e.g., adjustable arm support) can provide several degrees of freedom, including lift, lateral translation, tilt, etc. Thus, dependent on the embodiment, a robotic medical system can have many more robotically controlled degrees of freedom beyond just those in the robotic arms 210 to provide for null space movement and collision avoidance. In each of these embodiments, the end effectors of one or more robotic arms (and any tools or instruments coupled thereto) and/or a remote center of a tool associated therewith can advantageously maintain in pose and/or position within a patient.

A robotic arm 210 having at least one redundant DoF has at least one more DoF than the minimum number of DoFs for performing a given task. For example, a robotic arm 210 can have at least seven DoFs, where one of the joints 304 of the robotic arm 210 can be considered a redundant joint. The one or more redundant joints can allow the robotic arm 210 to move in a null space to both maintain the pose of the ADM 308 and a position of an RCM and avoid collision(s) with other robotic arms or objects.

In some embodiments, the robotic system 200 can be configured to perform collision avoidance to avoid collision(s), e.g., between adjacent robotic arms 210, by taking advantage of the movement of one or more redundant joints in a null space. For example, when a robotic arm 210 collides with or approaches (e.g., within a defined distance of) another robotic arm 210, one or more processors of the system can be configured to detect the collision or impending collision (e.g., via kinematics). Accordingly, the robotic system 200 can control one or both of the robotic arms 210 to adjust their respective joints within the null space to avoid the collision or impending collision. In one embodiment involving a pair of robotic arms, a base of one of the robotic arms and its end effector can stay in its pose, while links or joints therebetween move in a null space to avoid collisions with an adjacent robotic arm.

In certain embodiments, a robotic system 200 may use the redundant joints in the robotic arms as the sole null space DoF. When the robotic system 200 has only one DoF of null space motion, the null space may be a one-dimensional line through space. If the null space line takes one or more of the robotic arm(s) 210 through an invalid pose or into a collision, the robotic system 200 may not be able to provide null space adjustment and collision avoidance for certain ADM poses and/or RCM positions.

C. Exemplary Movements of Robotic Arm and Underlying Bar

FIGS. 24A-24F illustrate exemplary movements of a robotic arm 210 and its underlying bar 220 according to some embodiments.

In accordance with some embodiments of the present disclosure, an underlying bar 220 of a robotic arm 210 can be automatically moved while the user is manipulating the robotic arm 210 (e.g., in a manual manipulation mode). The ability to cause automatic bar translation during arm manipulation advantageously makes the setup process (and/or adjustments to the system setup) easier and faster for the operator.

Figure 24A:
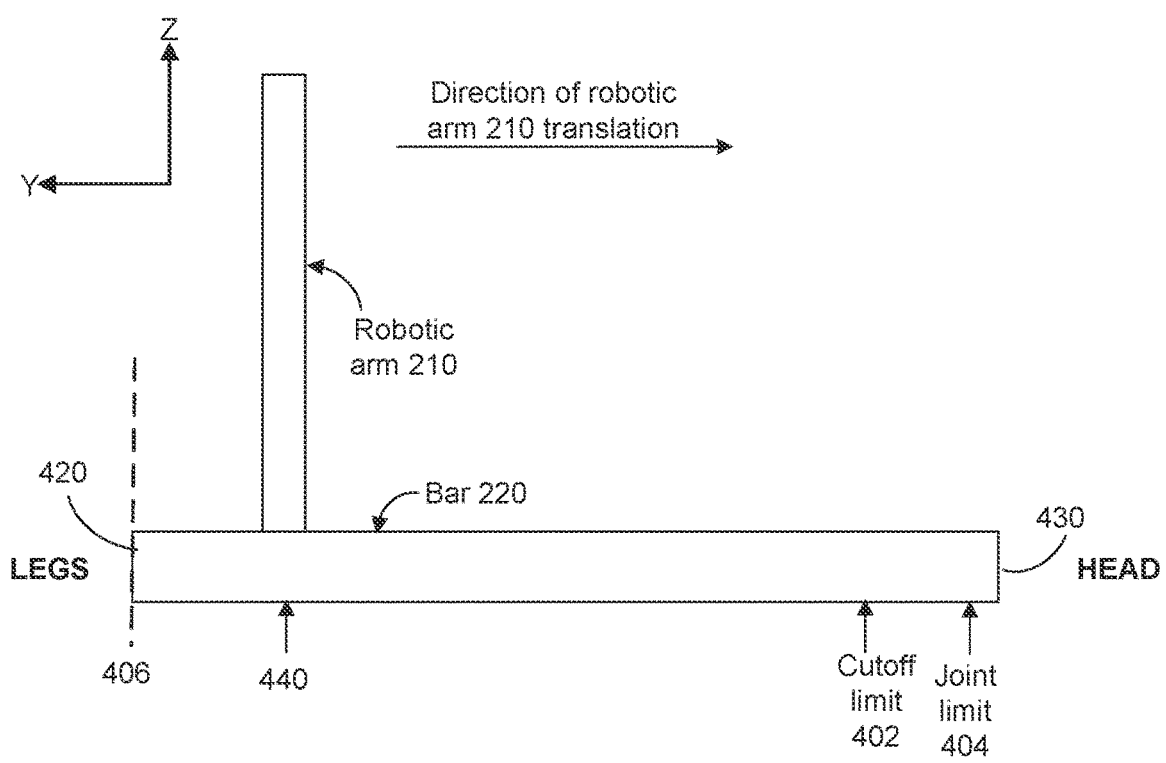
FIGS. 24A-24F illustrate exemplary movements of a robotic arm 210 and its underlying bar 220 according to some embodiments.

FIG. 24A illustrates an initial position 440 of the robotic arm 210 on the bar 220. The bar 220 includes a first end 420 that is located near the legs of the patient support platform 202 and a second end 430 that is located near the head of the patient support platform 202. In this example, the robotic arm 210 translates along a length of the bar 220 towards the second end 430 (e.g., along the negative y-direction). In some embodiments, translation of the robotic arm 210 along the bar 220 is facilitated by a prismatic or base joint (e.g., base joint 304-1) of the robotic arm 210-1. FIG. 24A also shows an initial position 406 (e.g., denoted by the initial position of the first end 420 of the bar 220) relative to the robotic system 200 (e.g., relative to a base 206 of the robotic system, FIGS. 21 and 22) or relative to the patient support platform 202.

In some embodiments, there are two limits to take into consideration for robotic arm translation along the bar: a cutoff limit 402 (e.g., cutoff position) and a joint limit 404 (e.g., the A0 joint limit). The cutoff limit 402 is a limit that occurs at or before the joint limit 404. In FIG. 24A, as the robotic arm 210 translates along the bar 220 towards the head, the robotic arm 210 will encounter the cutoff limit 402 prior to the joint limit 404.

In some embodiments, the joint limit 404 is the limit of how far the base joint (e.g., base joint or A0 joint 304-1) of the robotic arm 210 can translate along the bar 220. In some embodiments, a haptic wall (e.g., a virtual wall) is placed at the joint limit 404 so that a user cannot manually move the robotic arm 210 to reach the joint limit 404. In some embodiments, the cutoff limit 402 can be viewed as a "soft" limit while the joint limit 404 can be viewed as a "hard" limit. For example, in some embodiments, the cutoff limit 402 can be located 10-25 mm (e.g., approximately 25 mm in one embodiment) from an end (e.g., the head end) of the bar 220, while the joint limit 404 can be located 5-12 mm (e.g., approximately 10 mm in one embodiment) from the head end of the bar 220.

Figure 24B:
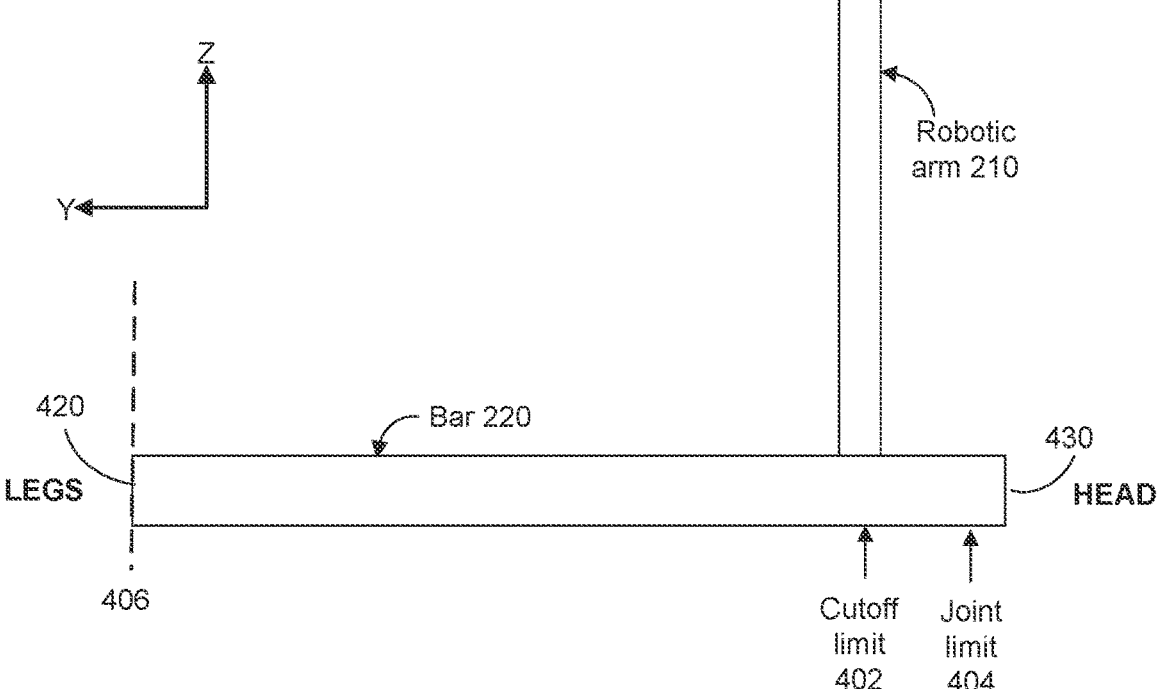

FIG. 24B illustrates the robotic arm 210 entering into the cutoff limit 402 as it translates along the bar 220 towards the second end 430.

In some embodiments, automatic movement of the bar 220 is triggered when the robotic arm 210 is being held at the cutoff limit 402 for a certain preset time (e.g., 2 seconds, 3 seconds, 5 seconds, etc.). For example, if the robotic arm 210 is held within the cutoff limit 402 for at least the preset amount of time, automatic bar translation will be activated. In some embodiments, the preset amount of time is dynamically adjusted by the medical system based on the characteristics of the movement (e.g., speed, acceleration, distance, etc.) of the robotic arm or the characteristics of sensor input (e.g., force, moment, locations, etc.) detected on the robotic arm that is being moved into the cutoff limit. In some embodiments, the preset amount of time is user-configurable. In some embodiments, automatic movement of the bar 220 is triggered in accordance with the cutoff limit 402 being exceeded by the first robotic arm, optionally without a time requirement.

Figure 24C:
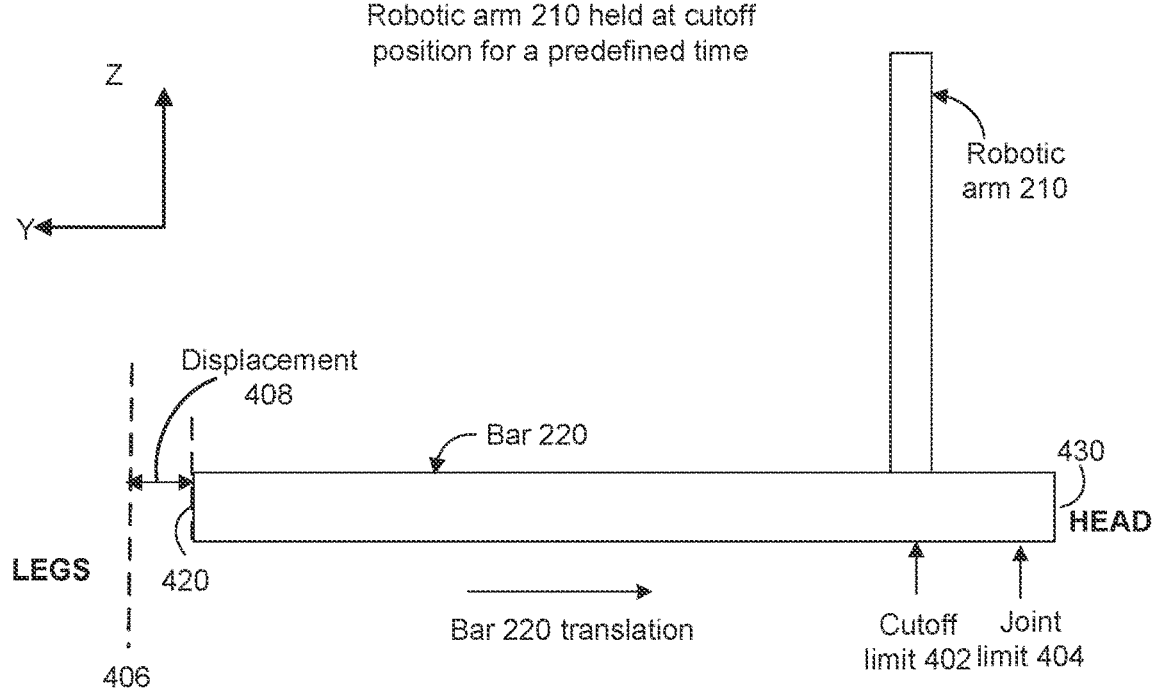

FIG. 24C illustrates activation of automatic bar translation after the robotic arm 210 is held at the cutoff position for a preset amount of time. In this example, the bar 220 is displaced a distance (408) from its initial position 406 and moves relative to the patient support platform 202 or the base 206 of the robotic system 200. The robotic arm 210 translates together with the bar 220 in the same direction as the bar translation. The robotic arm 210 is still held at the cutoff position 402 during the bar (and arm) translation. In some embodiments, and as illustrated in FIG. 24C, bar translation is in the same direction as the robotic arm translation. In other embodiments, the bar 220 may move in a direction that is opposite from the direction of robotic arm translation (e.g., the bar 220 moves toward the legs and the robotic arm 210 moves toward the head, or vice versa), or the bar 220 may move in both directions. In some embodiments, the bar 220 will initially begin to move at a constant velocity in the direction of the joint limit 404. In some embodiments, to maintain automatic movement of the bar 220, a user will need to apply continuous force to the robotic arm 210 under impedance mode or admittance mode. In some embodiments, the bar 220 will keep translating in the initial direction while the robotic arm 210 is at or past the cutoff limit 402 (e.g., without requiring continuous force being maintained on the robotic arm, or without requiring movement of the robotic arm relative to the bar, etc.), until the bar 220 reaches its limit of translation (e.g., when the bar reaches a D7 limit).

Figure 24D:
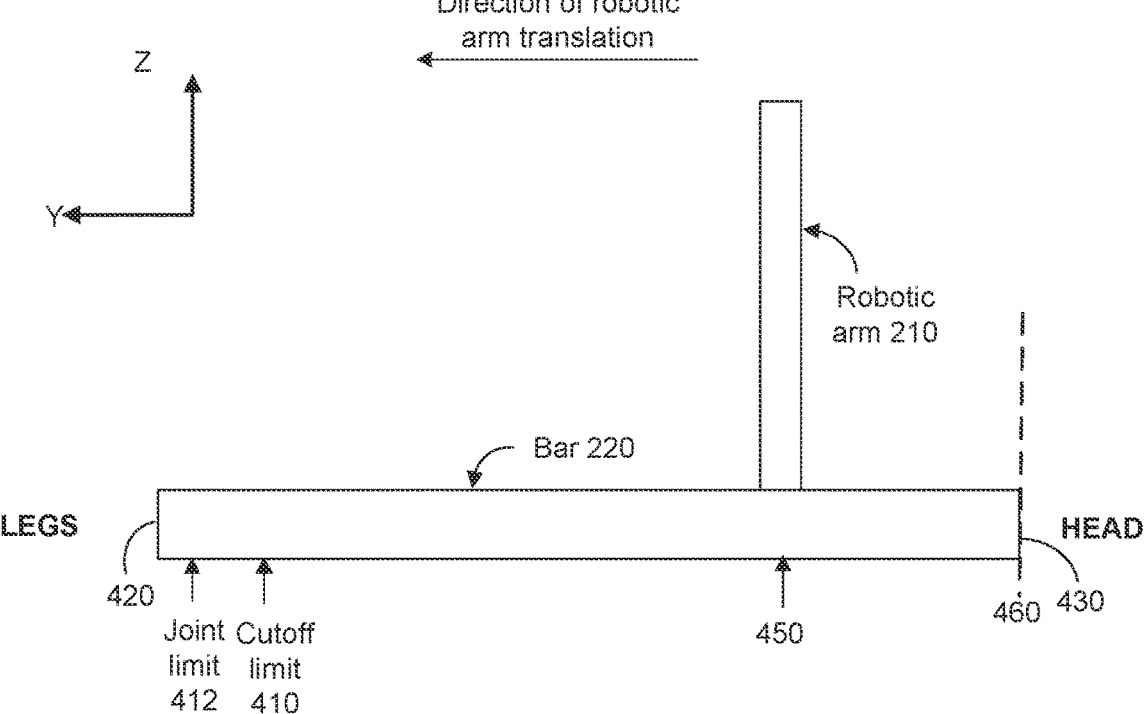
Figure 24E:
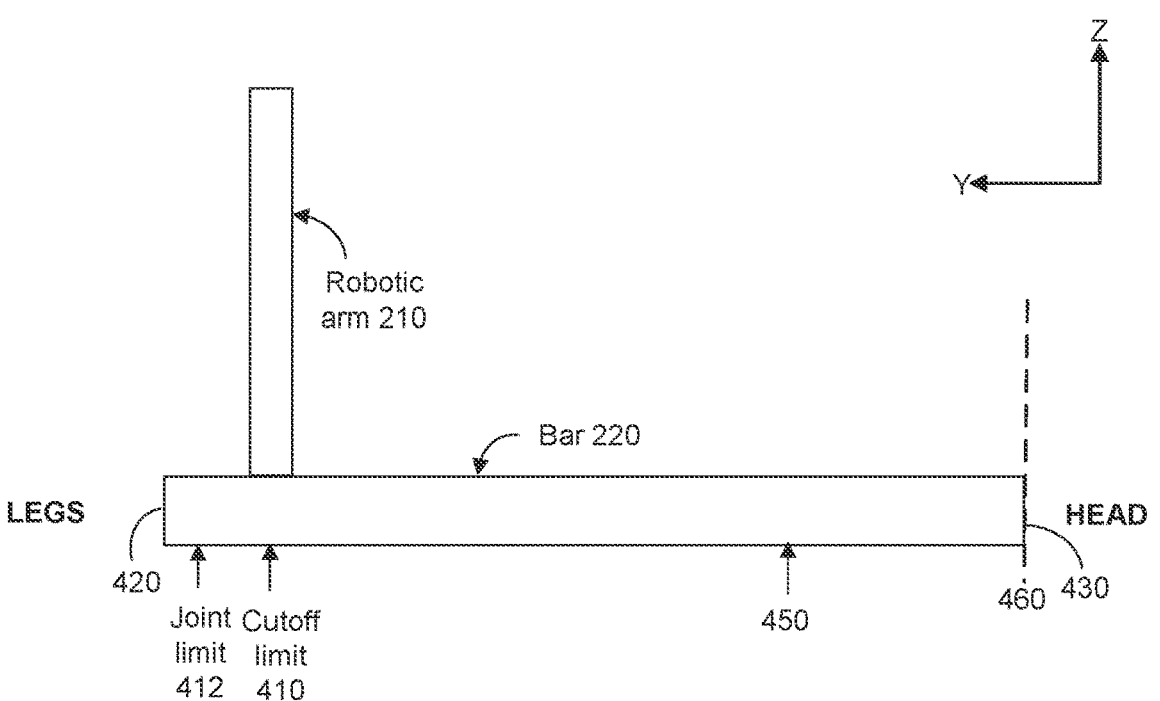
Figure 24F:
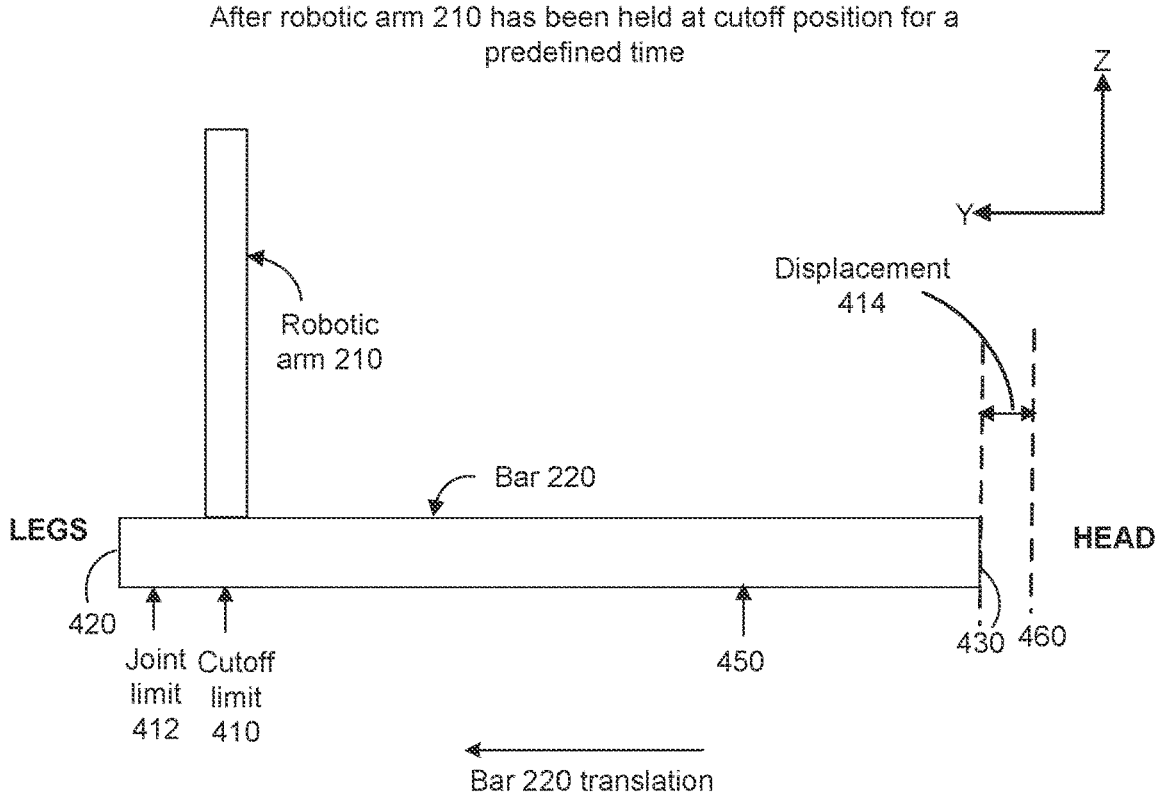

FIGS. 24D-24F illustrate another exemplary scenario for arm and bar translation.

FIG. 24D shows the robotic arm is at an initial position 450 on the bar 220. The bar 220 has an initial position 460 relative to the base 206 of the robotic system 200 or relative to the patient support platform 202. The robotic arm 210 translates along the bar 220 toward the first end 420 of the bar. In this example, the robotic arm 210 will encounter a cutoff limit 410 prior to the joint limit 412.

FIG. 24E illustrates the robotic arm 210 entering into the cutoff limit 410 as it translates along the bar 220 towards first end 420 under manual manipulation.

FIG. 24F illustrates automatic bar translation after the robotic arm 210 is held at a position at or beyond the cutoff limit 410 for at least a preset amount of time (e.g., 2 seconds, 3 seconds, or 5 seconds). In this example, the bar 220 is displaced a distance (416) from its initial position 460 (e.g., as denoted by the initial position of the second end 430 of the bar) relative to the patient support platform 202. The bar 220 and the robotic arm 210 move in the same direction (e.g., toward the legs), and the robotic arm 210 is held at or beyond the cutoff limit 410 during the bar and arm translation.

The examples of FIGS. 24A-24F show one robotic arm 210 on the bar 220. In some embodiments, the robotic arm 210 is one of a plurality of robotic arms on the bar 220 (e.g., as illustrated in FIGS. 21 and 22). In some embodiments, the robotic arm 210 in FIGS. 24A-24F represents one of a plurality of robotic arms on the bar and located at an end of the bar 220. For example, the robotic arm 210 in FIGS. 24A-24C may represent the robotic arm 210-3 or the robotic arm 210-6 in FIG. 22, whereas the robotic arm 210 in FIGS. 24D-24F may represent the robotic arm 210-1 or the robotic arm 210-4 in FIG. 22.

D. Exemplary Processes for Automatic Bar Translation

Figure 25A:
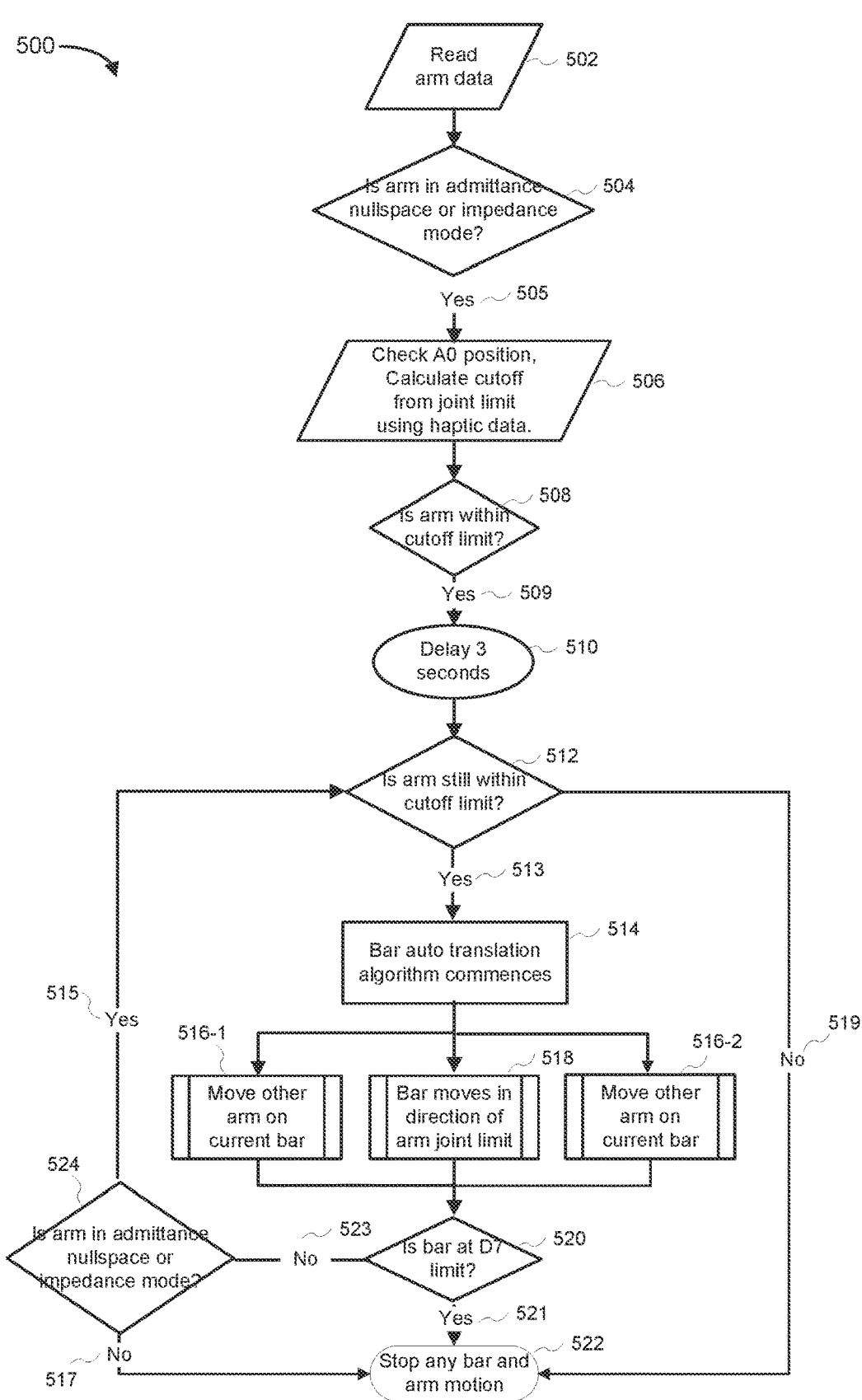
FIGS. 25A and 25B illustrate a flow diagram for automatic bar translation according to some embodiments.
Figure 25B:
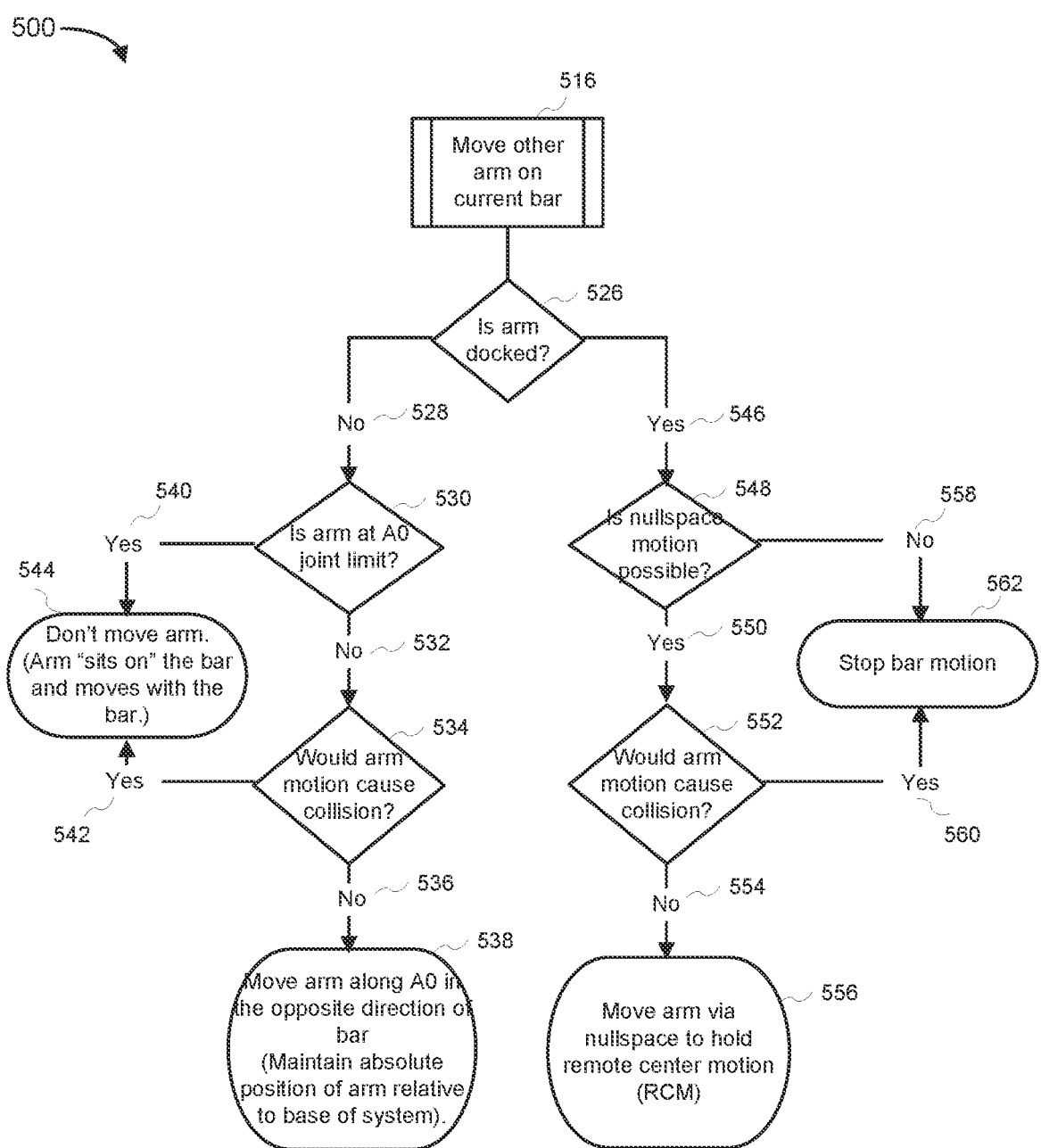

FIGS. 25A and 25B are a flow diagram 500 for automatic bar translation according to some embodiments. In some embodiments, the steps in the flow diagram 500 are executed by one or more processors (e.g., in FIG. 20) of a robotic medical system (e.g., the robotic system 200 as illustrated in FIGS. 21, 22, 26, and 27) in accordance with instruction stored on memory of the robotic medical system.

In some embodiments, the processors read (502) data of a robotic arm (e.g., an active robotic arm, such as robotic arm 210 in FIGS. 21, 22, 23, 24, 26, and 27). The robotic arm is movably coupled to a bar (e.g., bar 220 in FIGS. 21, 22, 24, 26, and 27). Based on the data, the processors determine (504) whether the robotic arm is in an admittance nullspace or an impedance mode (e.g., a manual manipulation mode). In accordance with a determination (505) that the robotic arm is in an admittance nullspace and/or in the impedance mode, the processors determine (e.g., check) (506) a base joint position (e.g., position of the base joint or A0 joint 304-1) of the robotic arm along the bar. The processors also calculate (506) a cutoff (e.g., cutoff limit 402 in FIG. 24A or cutoff limit 410 in FIG. 24D) from a joint limit (e.g., joint limit 404 in FIG. 24A or joint limit 412 in FIG. 24D) using haptic data. The processors also determine whether the robotic arm is (508) within the cutoff limit.

In some embodiments, in accordance with a determination (509) that the robotic arm is within the cutoff limit, the processors start a time delay (510) (e.g., 2 seconds, 3 seconds, 5 seconds, or a user-defined time delay, etc.). After the time delay, the processors determine whether the robotic arm is (512) still within the cutoff limit. In accordance with a determination that the robotic arm is not within the cutoff limit after the time delay (519), the processors will stop automatic bar motion and corresponding automatic arm motion for other robotic arms (522). In accordance with a determination that the robotic arm is still within the cutoff limit after the time delay (513), the processors commence (514) (or continues) a bar translation algorithm, in which the bar is automatically moved (518) in the direction of the arm joint limit that has been exceeded by the robotic arm (e.g., joint limit 404 in FIG. 24A or joint limit 412 in FIG. 24D), and/or one or more other arms (e.g., non-active arm(s)) on the bar are automatically moved (516).

Details of step 516, step 518, and the steps in FIG. 25B regarding movement of the one or more other arms on the bar will be discussed with respect to various embodiments in FIGS. 26 and 27.

In some embodiments, during the execution of the bar auto translation algorithm (e.g., execution of the steps 516 and 518), the processors may determine (e.g., obtain updated data) (e.g., continuously or on a periodic basis, such as every 10 seconds, 15 seconds, or 20 seconds, etc.) whether the bar has reached its limit of translation (e.g., D7 translation)

(520). In some embodiments, in accordance with a determination that the bar has reached its limit of translation (521), the processors will stop any bar and arm(s) motion (522). In some embodiments, in accordance with a determination that the bar has not reached its limit of translation (523), the processors determine whether the robotic arm (e.g., the active robotic arm) is in an admittance nullspace or the impedance mode (e.g., a manual manipulation mode) (524). In some embodiments, in accordance with a determination that the robotic arm is not in an admittance nullspace or the impedance mode (517), the processors will stop automatic bar motion and automatic arm motion for other robotic arms (522). In accordance with a determination that the active arm is still in an admittance nullspace or in the impedance mode (515), the processors determine whether the robotic arm is still within the cutoff limit (512), and if so (513), the processors continues execution of the bar translation algorithm (513). In some embodiments, in accordance with a determination that the robotic arm is no longer within the cutoff limit (519), the processors will stop automatic bar motion and automatic motion of the other arm(s) (522).

In light of these principles, we now turn to various embodiments.

E. Exemplary Scenarios

FIGS. 26A to 26E illustrate an exemplary sequence of arm and bar movements of a robotic system 200 according to some embodiments. For the sake of clarity, only the robotic arms in the foreground (e.g., the robotic arms 210-1, 210-2, and 210-3) and their underlying bar 220-1 (e.g., adjustable arm support) are shown.

Figure 26A:
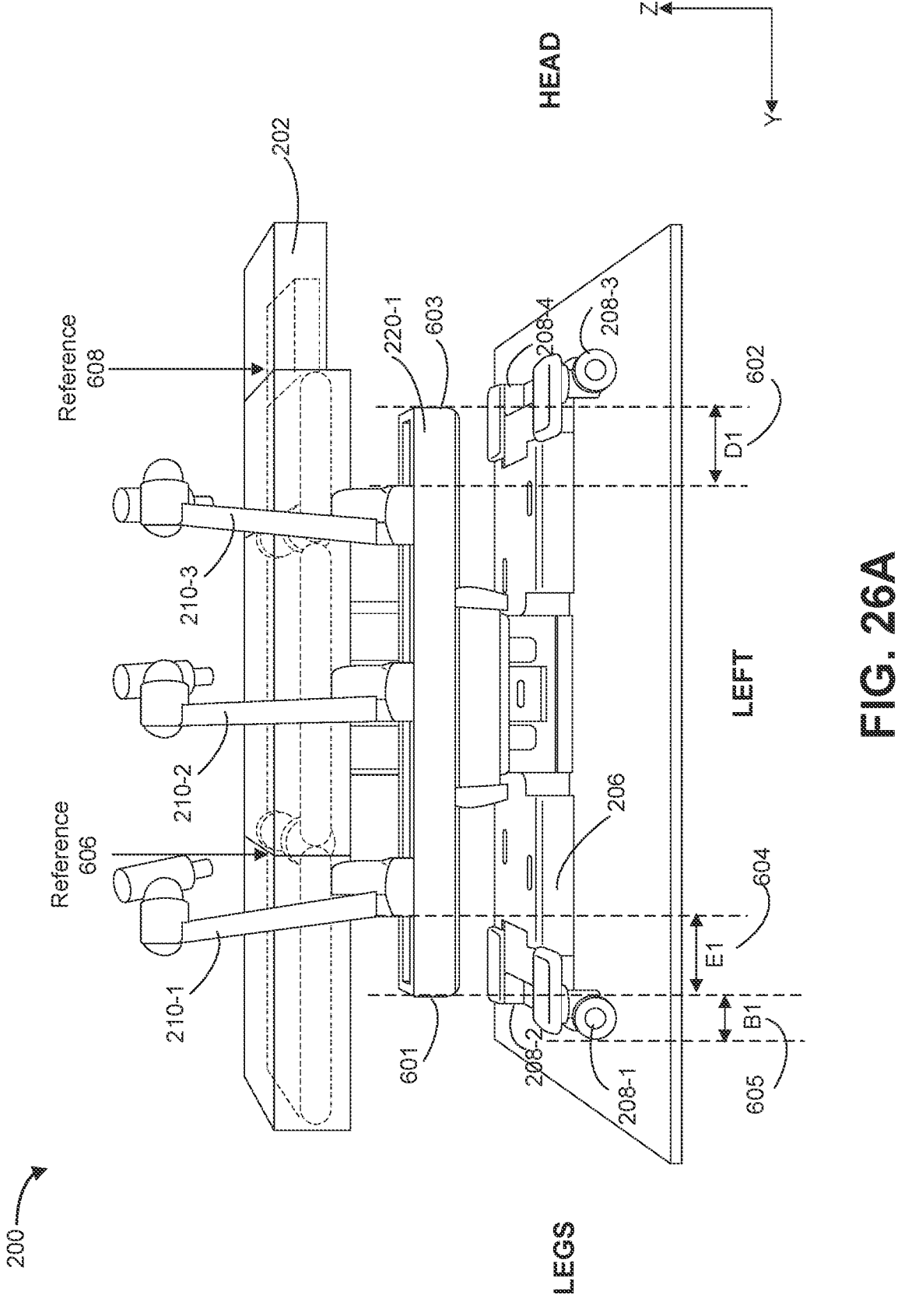
FIGS. 26A to 26E illustrate an exemplary sequence of arm and bar movements of a robotic system according to some embodiments.

FIG. 26A illustrates initial positions of the robotic arms (e.g., arms) 210-1, 210-2, and 210-3 on the bar 220-1. The robotic arms 210-1, 210-2, and 210-3 are movably coupled to the bar 220-1 (e.g., via a respective base joint 304-1 that couples the robotic arm to the bar). The bar 220-1 includes a first end 601 and a second end 603. In this example, each of the robotic arms 210-1, 210-2, and 210-3 is in an undocked position (e.g., no cannula detected by the respective cannula sensor, arms are free to move without risk of patient safety or upsetting an established configuration, etc.). The robotic arm 210-1 is located at a distance E1 (604) from the first end 601 of the bar 220-1. The robotic arm 210-3 is located at a distance D1 (602) from the second end 603 of the bar 220-1. The wheel 208-1 is used as a reference point for the base 206, and the distance between the wheel 208-1 and the bar 220-1 is B1 (605). FIG. 26A also identifies reference positions 606 and 608 on the patient support platform 202, which will be used as markers in this example.

Figure 26B:
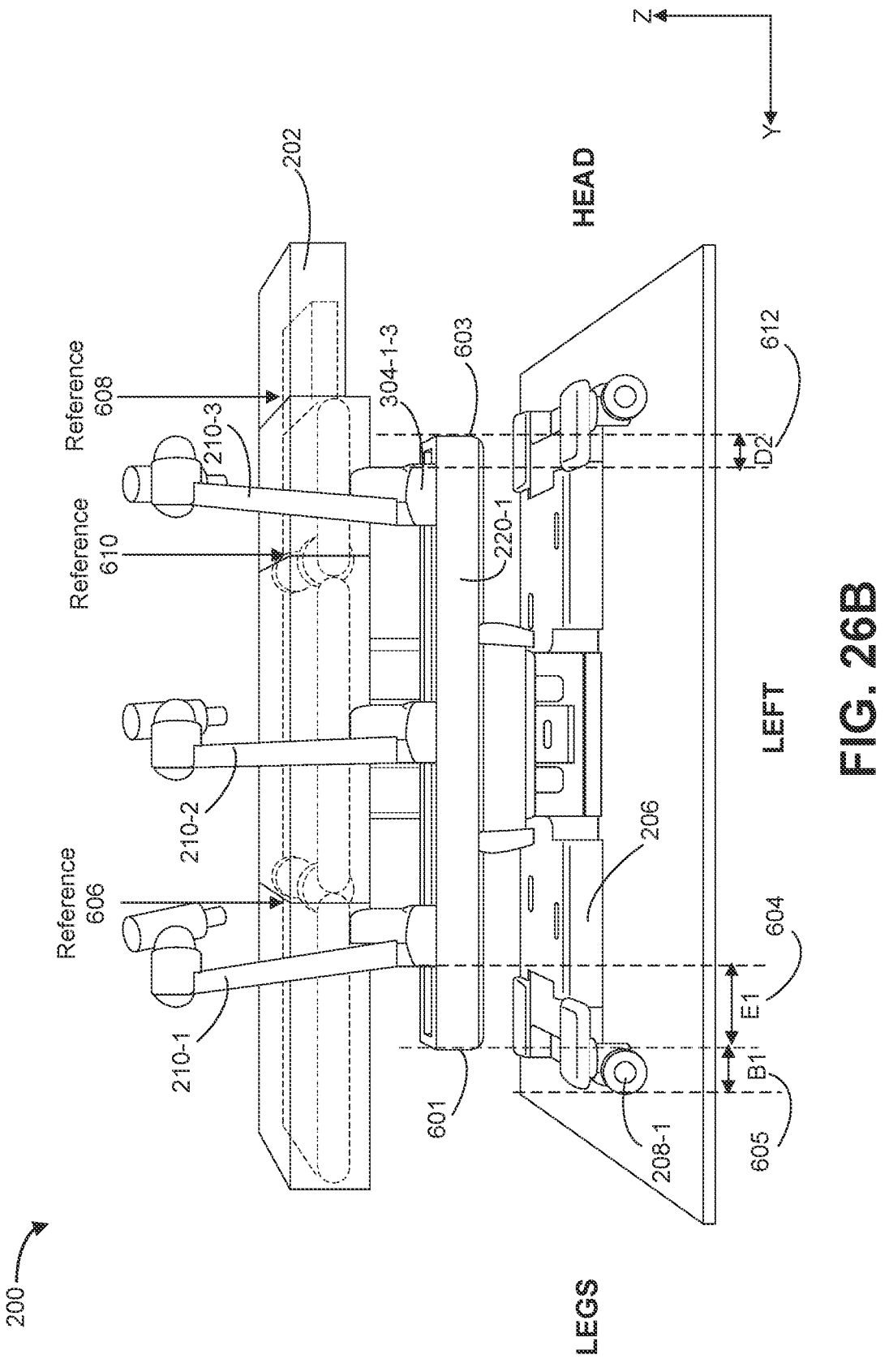

FIG. 26B illustrates movement (e.g., translation) of the robotic arm 210-3 (e.g., at the base joint 304-1-3 of the robotic arm 210-3) along the bar 220-1 toward the second end 603 (e.g., toward the head of the patient support platform 202). In some embodiments, the movement of the robotic arm 210-3 includes a manual manipulation (e.g., in an impedance control mode, an admittance control mode, or a direct push or pull by a user of the robotic system 200, etc.). In some embodiments, the movement of the robotic arm 210-3 includes a motor-assisted movement. In some embodiments, and as illustrated in step 502 in FIG. 25A, the processors obtain data of the robotic arm 210-3 (e.g., force, torque, momentum, location, and/or distance traveled) during the arm movement.

FIG. 26B also illustrates that, in accordance of the movement of the robotic arm 210-3, the distance between the robotic arm 210-3 and the second end 603 of the bar 220-1 decreases from D1 (602) to D2 (612). In some embodiments, and as illustrated in FIG. 26B, the robotic arms 210-1 and 210-2 and the bar 220-1 remain stationary (e.g., with respect to the base 206 or the patient support platform 202) during the translation of the robotic arm 210-3 along the bar 220-1. In this example, the bar 220-1 also remains stationary with respect to the base 206 during the arm translation. The distance between the reference position based on the wheel 208-1 (e.g., the base 206) and the position of the bar 220-1 (e.g., based on the position of the first end 601) is at B1 (605) in both FIGS. 26A and 26B.

In some embodiments, as the robotic arm 210-3 moves along the bar 220-1 toward one end (e.g., the second end 603), the robotic arm 210-3 enters into a cutoff region at or beyond a cutoff limit (e.g., cutoff limit 402, FIG. 24A). In the example of FIG. 26B, D2 (612) represents the cutoff region defined by a cutoff limit from the second end 603 of the bar 220-1. In some embodiments, and as illustrated in FIGS. 24 and 25A (e.g., steps 508, 512, and 513), if the robotic arm 210-3 is held within cutoff region defined by the cutoff limit 612 for at least a preset period of time (e.g., 2 seconds, 3 seconds, 5 seconds, a user-configured time period, a dynamically calculated time period, etc.), automatic translation of the bar 220-1 is activated (Step 514, FIG. 25A).

Figure 26C:
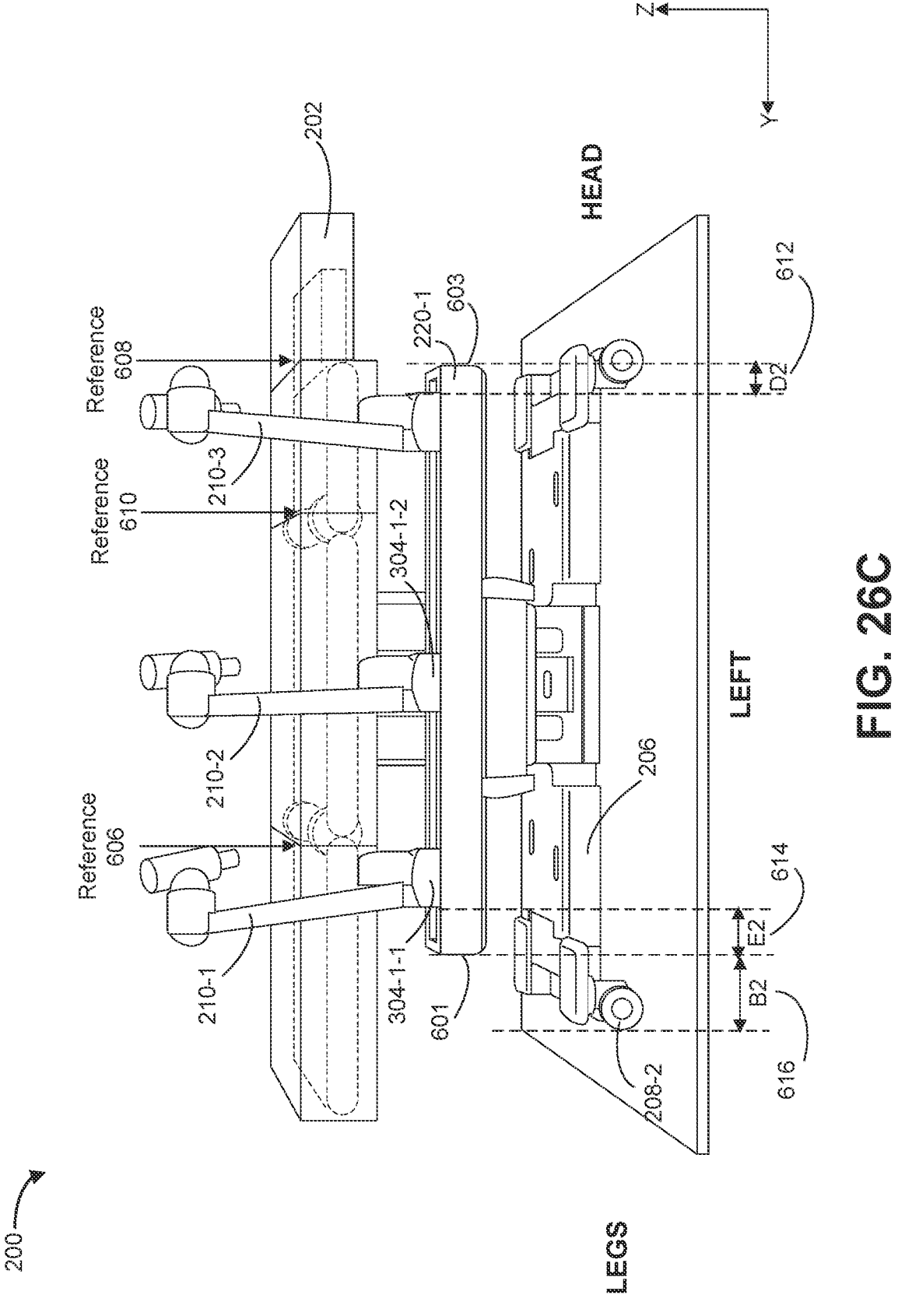

FIG. 26C illustrates automatic translation of the bar 220-1 (e.g., by the processors of the robotic system 200) relative to the base 206 in response to the robotic arm 210-3 being held at or beyond the cutoff limit (e.g., within the cutoff region D2) (612) for at least the preset period of time. In this example, the bar 220-1 automatically moves toward the head of the patient support platform (e.g., in the direction of the joint limit of the robotic arm 210-3). In accordance with the bar translation, the distance between the bar 220-1 and the wheel 208-2 increases from B1 (605) to B2 (616). During the bar translation, the robotic arm 210-1 maintains its cutoff limit position (e.g., within D2 (612) with respect to the second end 603 of the bar 220-1). The patient support platform 202 remains stationary with respect to the base 206 during the arm and bar translation.

In some embodiments, in accordance with the movement of the bar 220-1, one or more other robotic arms (e.g., non-active robotic arms) can maintain their absolute positions with respect to the base 206 of the robotic system 200. For example, in FIG. 26C, the robotic arm 210-1 (e.g., the base joint 304-1-1 corresponding to the robotic arm 210-1) and the robotic arm 210-2 (e.g., the base joint 304-1-2 corresponding to the robotic arm 210-2) do not move with the bar 220-1, but instead maintain their absolute positions relative to the base 206 and to the stationary patient support platform 202, as illustrated in FIG. 26C (e.g., using the reference positions 606, 608, and 610 on the patient support platform 202 as markers).

In some embodiments, the non-movement of the non-active robotic arms 210-1 and 210-2 (e.g., the robotic arms that are not under the manual manipulation mode, but may optionally undergo automatic motion as a result of the execution of the bar auto translation algorithm) in FIG. 26C is consistent with the bar auto translation algorithm that is described in FIG. 25. In FIG. 26C, each of the robotic arms 210-1 and 210-2 is in an undocked position. This corresponds to step 528 in FIG. 25B. Furthermore, in FIG. 26C, the robotic arms 210-1 and 210-2 are not at the A0 joint limit. This corresponds to step 532 in FIG. 25B). Moreover, motion of the robotic arms 210-1 and 210-2 will not cause collision (536, FIG. 25B). Therefore, in this scenario, and according to Step 538 in FIG. 25B, the processors will maintain an absolute position of the robotic arm 210-1 (e.g., the base joint (e.g., A0 joint) 304-1-1 of the robotic arm 210-1) relative to the base 206 of the robotic system 200. The processors will also maintain an absolute position of the robotic arm 210-2 (e.g., the base joint (e.g., A0 joint) 304-1-2 of the robotic arm 210-2) relative to the base 206 of the robotic system 200. Stated another way, the processors will move the robotic arms 210-1 and 210-2 along their respective base joints 304-1-1 and 304-1-2 in the opposite direction of the bar movement that they remain stationary with respect to the base 206.

FIG. 26C also shows that in accordance with the translation of the bar 220-1, the distance between the robotic arm 210-1 and the first end 601 decreases from E1 (604) in FIG. 26B to E2 (614) in FIG. 26C.

Figure 26D:
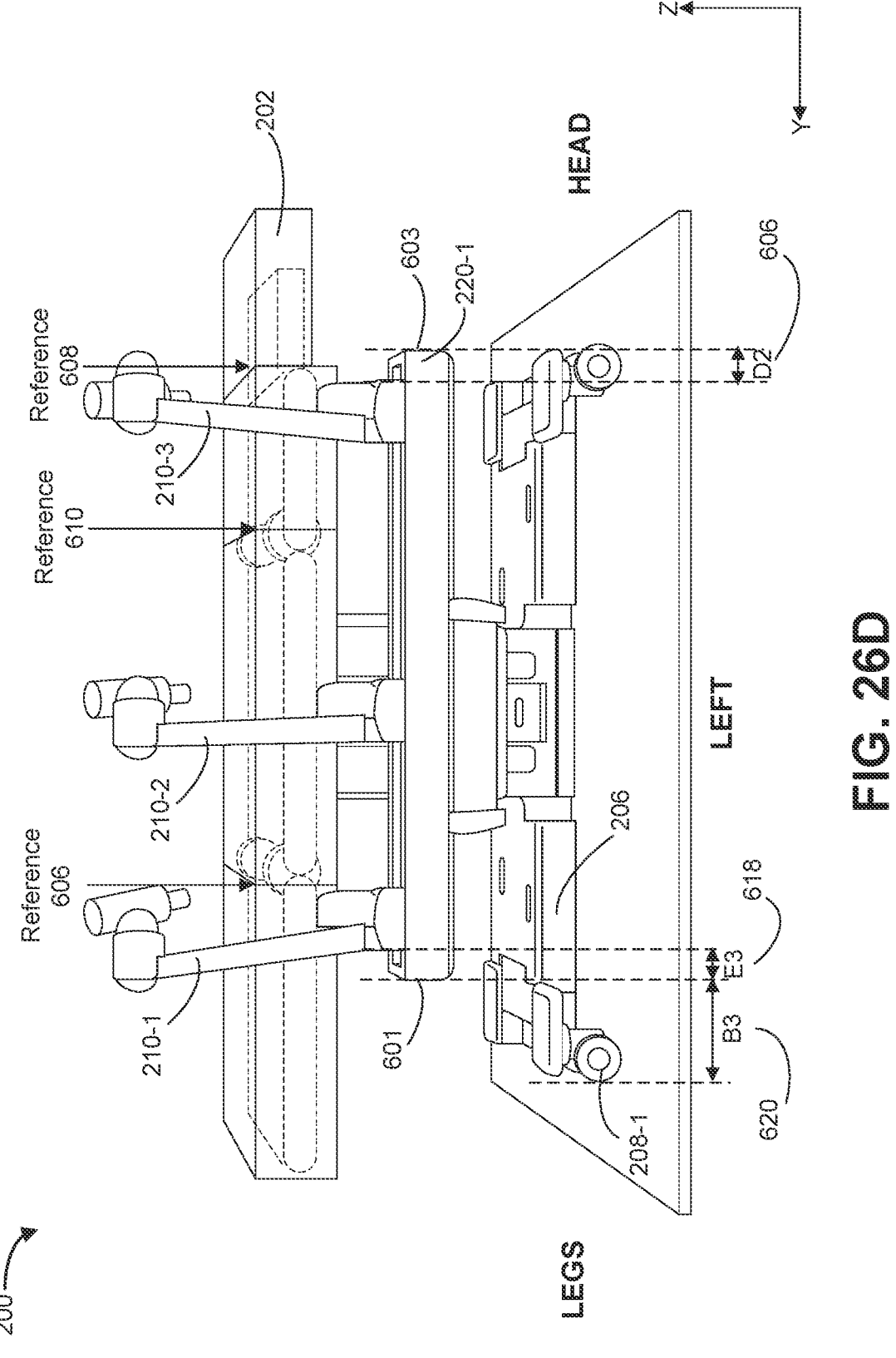

FIG. 26D illustrates continued translation of the bar 220-1 toward the head of the patient support platform 202. In accordance with the translation, the distance between the first end 601 of the bar 220-1 and the wheel 208-2 increases from B2 (616) to B3 (620). The distance between the robotic arm 210-1 and the second end 603 of the bar 220-1 decreases from E2 (614) to E3 (618).

In some embodiments, the robotic arm 210-1 reaches its joint limit (e.g., A0 joint limit 412, FIG. 24D) as a result of the bar 220-1 translation (while the robotic arm 210-1 keeps stationary with respect to the base 206). Suppose the robotic arm 210-1 reaches its joint limit at E3 (616) in FIG. 26D. In some embodiments, when a joint limit is reached on a non-active robotic arm, such as the robotic arm 210-1 in FIG. 26D, the processors will move the non-active robotic arm with the underlying bar (e.g., bar 220-1) in the same direction of bar translation. This is depicted in Steps 530, 540, and 544 in FIG. 25B.

Figure 26E:
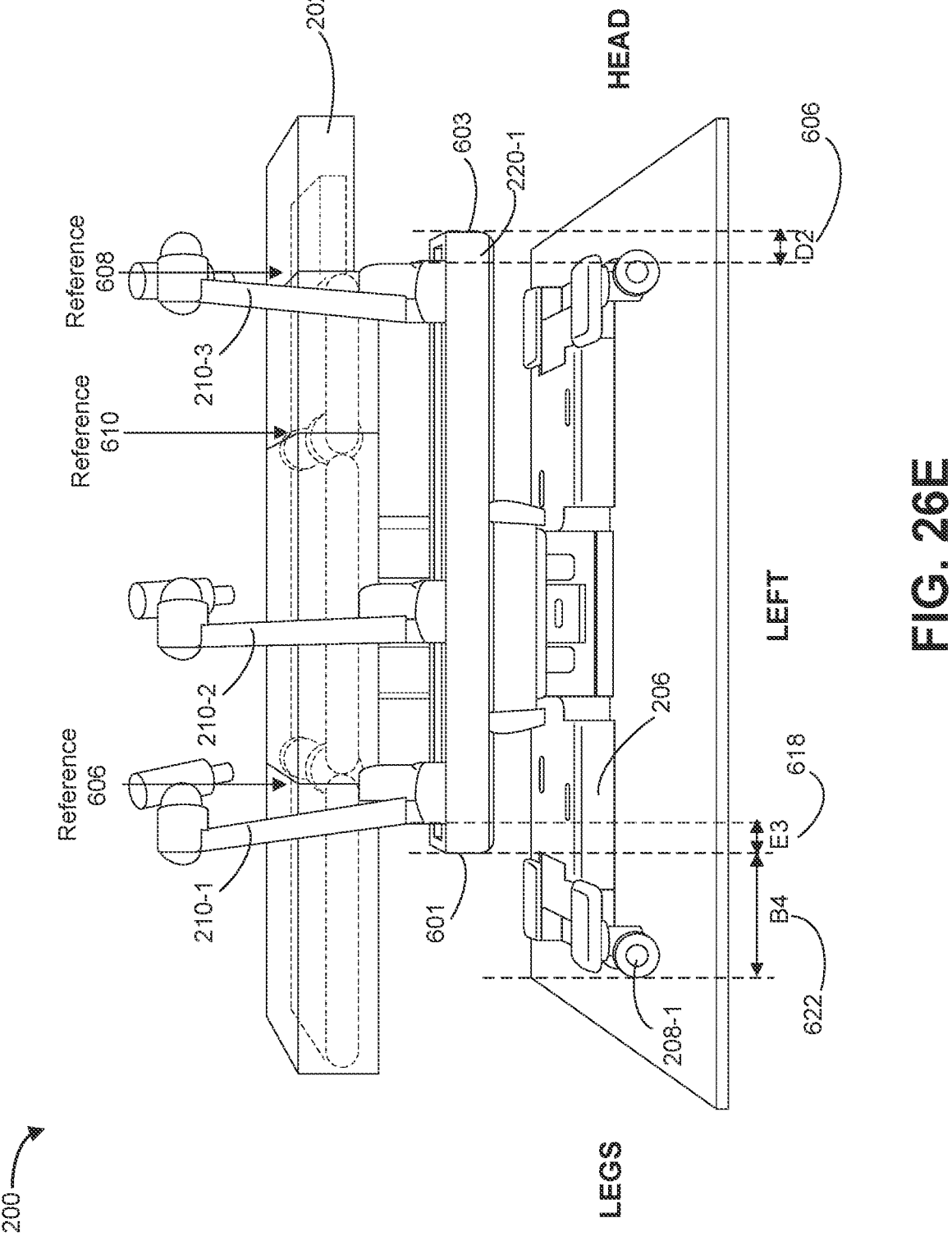

FIG. 26E illustrates further translation of the bar 220-1 toward the head of the patient support platform 202. In this example, because the robotic arm 210-1 has reached its joint limit E3 (618), the robotic arm 210-1 moves together with (e.g., at the same velocity as) the bar 220-1 in the same direction. This action corresponds to Step 544 in FIG. 25B. Stated another way, in FIG. 26E (step 544), the processors cause the robotic arm 210-1 to "sit on" the bar 220-1 and move with the bar 220-1; the processors do not activate motion in the arm 210-1 independent of the bar 220-1 motion. FIG. 26E also shows that as a result of the bar 220-1 translation, the distance between the bar 220-1 and the wheel 208-1 increases from B3 (620) to B4 (622).

In some embodiments, and as illustrated in FIG. 26E, in accordance with the movement of the bar 220-1 and the robotic arm 210-1, the other non-active robotic arm (e.g., the robotic arm 210-2) maintains its absolute position relative to the base 206 and to the stationary patient support platform 202. This corresponds to Step 538 in FIG. 25B. Here, the robotic arm 210-2 is not at its A0 joint limit (Step 530) and motion of the robotic arm 210-1 (as well as motion of the robotic arm 210-3) will not cause collision with the robotic arm 210-2 (Step 536, FIG. 25B).

In some embodiments, continued motion (e.g., automatic translation) of the bar 220-1 will cause the bar 220-1 to reach its limit on bar translation (e.g., D7 limit) (Step 521, FIG. 25A). In this situation, all automatic bar and arm motion will stop (Step 522, FIG. 25A).

In some embodiments, in accordance with the continued movement of the bar 220-1 and the robotic arm 210-1, the robotic arm 210-1 may approach collision with the robotic arm 210-2 (Step 542, FIG. 25B). In this situation, the processors will cause both the robotic arm 210-2 and the robotic arm 210-1 to "sit on" the bar 220-1 and move with the bar 220-1 (Step 544, FIG. 25B) to avoid the collision.

FIGS. 27A-27D illustrate another exemplary sequence of arm and bar movements of a robotic system 200 according to some embodiments.

In the example of FIG. 27, the robotic arms 210-1, 210-2, and 210-3 are supported by an underlying bar 220-1. The bar 220-1 includes a first end 702 and a second end 704. The robotic arms 210-4, 210-5, and 210-6 are supported by an underlying bar 220-2. The bar 220-2 includes a first end 706 and a second end 708. The patient support platform 202 includes a first end 710 and a second end 712. The patient support platform 202 is stationary in this exemplary sequence. Accordingly, the first end 710, the second end 712, the dotted lines on and various positions of the patient support platform 202 can be used as reference markers in the descriptions herein. The initial distance between the second end 704 of the bar 220-1 and the second end 712 of the patient support platform 202 is H1 (714). The initial distance between the first end 706 of the bar 220-2 and the first end 710 of the patient support platform 202 is J1 (716).

In some embodiments, the robotic arms include robotic arms that are in a docked position and robotic arms that are in an undocked position. In FIG. 27, the robotic arms 210-2 and 210-6 are in a docked position (e.g., due to the presence of instruments 212 in these arms, which are detected by their respective cannula sensors 310). The robotic arms 210-1, 210-3, 210-4, and 210-5 are in an undocked position.

Figure 27A:
FIGS. 27A-27F illustrate an exemplary sequence of arm and bar movements of a robotic system according to some embodiments.

FIG. 27A illustrates the robotic arm 210-1 is at or beyond a cutoff limit (e.g., cutoff limit 402, FIG. 24B) of the bar 220-1. The robotic arm 210-4 at or beyond a cutoff limit (e.g., cutoff limit 410, FIG. 24E) of the bar 220-2. In some embodiments, and as discussed previously with respect to FIGS. 25A and 26, in response to a robotic arm being held at or beyond a cutoff limit for at least a preset period of time, the processors of the robotic system 200 commence a bar auto translation algorithm (Step 514, FIG. 25A) in accordance with instructions stored on memory of the robotic system 200.

Figure 27B:

FIG. 27B illustrates automatic translation of the bar 220-1 in response to the robotic arm 210-3 being held at the cutoff limit for a predefined period of time. In this example, the bar 220-1 translates in the negative y direction (e.g., toward the head the patient support platform 202). In accordance with the bar 220-1 translation, the distance between the second end 704 of the bar 220-1 and the second end 712 of the patient support platform 202 decreases from H1 (714) to H2 (724).

In some embodiments, one or more other robotic arms (e.g., the robotic arm 210-1 and the robotic arm 210-2) that are movably coupled to the bar 220-1 may also move in accordance with the movement of the bar 220-1.

In the example of FIGS. 27A and 27B, the robotic arm 210-1 is in an undocked position. In some embodiments, and as illustrated in FIG. 25B, in accordance with a determination that the robotic arm 210-1 is in an undocked position (Step 528, FIG. 25B), the processors determine whether the robotic arm 210-1 is at its A0 joint limit (Step 530). In some embodiments, in accordance with a determination that the robotic arm 210-1 is at its A0 joint limit (Step 540), the processors will not move the robotic arm 210-1 (Step 544). Stated another way, the processors will cause the robotic arm 210-1 to "sit on" and move with the bar 220-1 (Step 544). This scenario has also been described in FIG. 26E.

In some embodiments, in accordance with a determination that the robotic arm 210-1 is not at its A0 joint limit (Step 532, FIG. 25B), the processors determine whether motion of the robotic arm 210-1 will cause collision (e.g., with another robotic arm, with other objects in the physical space, etc.) (Step 534). In accordance with a determination that motion of the robotic arm 210-1 will cause collision (Step 542), the processors will not move the robotic arm 210-1, but instead direct the robotic arm 210-1 to "sit on" the bar 220-1 and move with the bar 220-1 (e.g., in the same direction (e.g., and the same velocity) as the bar motion 220-1). In accordance with a determination that motion of the robotic arm 210-1 will not cause collision (Step 536), the processors will maintain an absolute position of the robotic arm 210-1 relative to the base 206 of the robotic system 200 (Step 538). Stated another way, the processors will move the robotic arm 210-1 (e.g., along its base joint) in the opposite direction of bar 220-1 translation (e.g., at the same speed as the bar 220-1 movement but in the opposite direction).

In the example of FIGS. 27A and 27B, the robotic arm 210-2 is in a docked position. Referring again to FIG. 25B, in some embodiments, in accordance with a determination that the robotic arm 210-2 is in a docked position (Step 546), the processors determine whether nullspace motion is possible for the robotic arm 210-2 (Step 548). In accordance with a determination that nullspace motion is not possible (Step 558) (e.g., due to no extra degree(s) of freedom present on the robotic arm, due to constraints based on collision avoidance and other requirements, etc.), the processors will stop automatic motion of the bar 220-1 (Step 562). In accordance with a determination that nullspace motion is possible (Step 550), the processors determine whether the nullspace motion of the robotic arm 210-1 will cause collision (Step 552). In some embodiments, in accordance with a determination that nullspace motion of the robotic arm 210-1 will not cause collision (Step 554), the processors will move the robotic arm 210-1 via nullspace (e.g., using one or more redundant joints of the robotic arm 210-1) to hold a remote center motion (RCM) of the robotic arm 210-1 (Step 556) stationary relative to the patient support platform. In some embodiments, in accordance with a determination that nullspace motion of the robotic arm 210-1 will cause collision (Step 560), the processors will stop automatic motion for the bar 220-1 (Step 562).

In FIG. 27A, it is possible for nullspace motion to be activated on the robotic arm 210-2 (e.g., due to the robotic arm 210-2 having one or more extra DoF). Accordingly, the processors move the robotic arm 210-2 via nullspace (e.g., using one or more redundant joints of the robotic arm 210-2) to hold a remote center motion (RCM) of the robotic arm 210-1 and to maintain the position and/or the orientation of the medical tool 212-1 (e.g., with respect to a patient on the patient support platform 202).

Figure 27C:
Figure 27D:
Figure 27E:
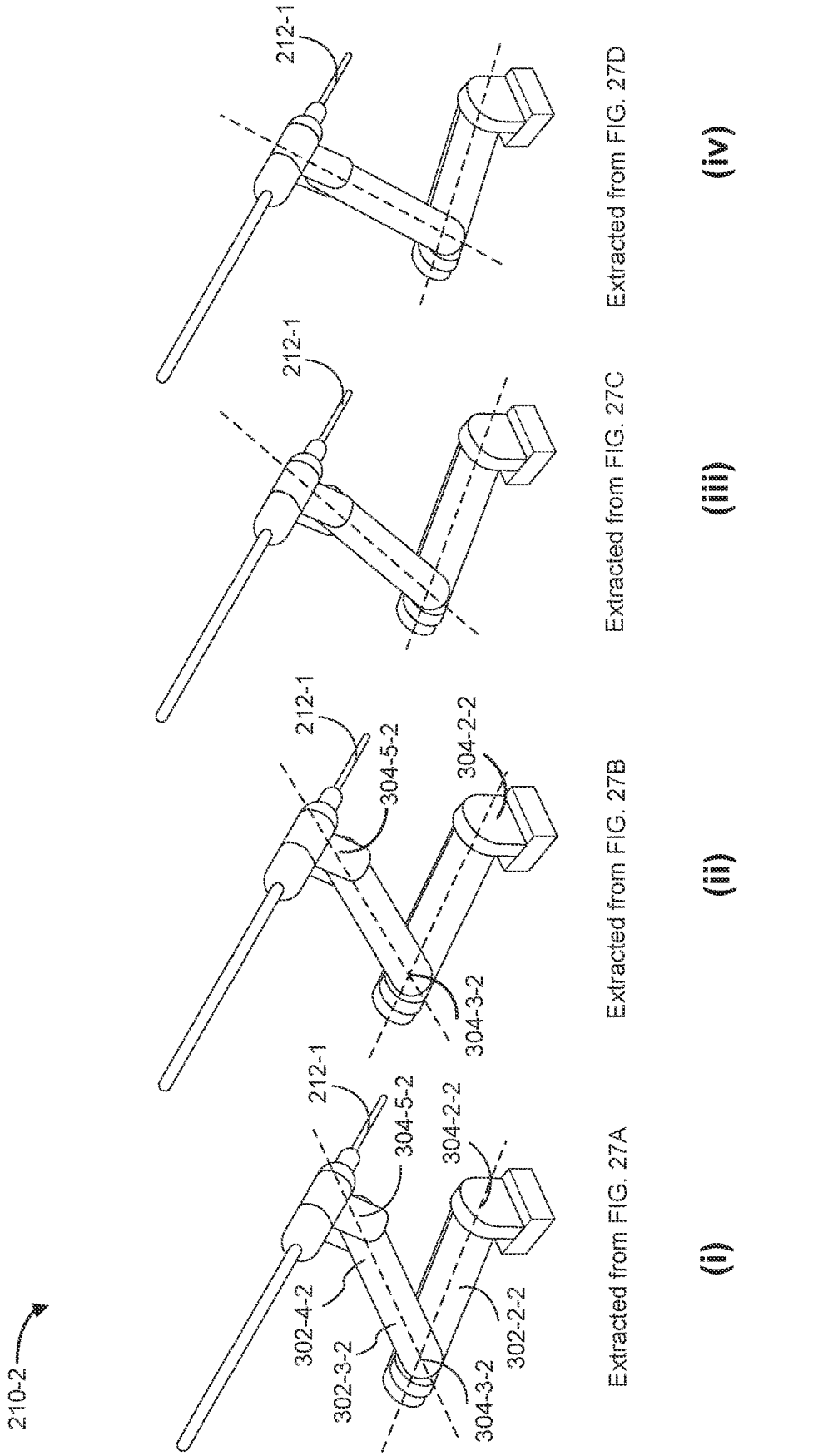

FIGS. 27E(i) and 27E(ii), which are extracted from FIG. 27A and FIG. 27B respectively, illustrate the change in pose of the robotic arm 210-2 as it executes nullspace motion to hold its RCM. As illustrated in FIGS. 27E(i) and 27E(ii), the robotic arm 210-2 moves one or more of the joints 304-2-2, 304-3-2, and 304-5-2 during nullspace motion, which in turn effect a change in position and/or orientation of one or more links (e.g., links 302-2-2, 302-3-2, and 302-4-2), to maintain the position and/or the orientation of the medical tool 212-1.

FIG. 27B also illustrates automatic movement of the bar 220-2 in response to the robotic arm 210-4 being held at or beyond the cutoff limit (e.g., cutoff limit 410) for at least a preset period of time. In this example, the bar 220-2 translates along the positive y-direction, towards the legs of the patient support platform 402. In accordance with the bar 220-2 translation, the distance between the first end 706 of the bar 220-2 and the first end 710 of the patient support platform 202 decreases from J1 (716) to J2 (720).

In some embodiments, one or more other robotic arms (e.g., the robotic arm 210-5 and the robotic arm 210-6) that are movably coupled to the bar 220-2 may also automatically move in accordance with the automatic movement of the bar 220-2. In some embodiments, the processors determine whether and/or how to move the other robotic arm(s) based on a docked state (e.g., docked position) of the arm(s). This process has been described above with respect to the robotic arms 210-1 and with reference to FIG. 25B, and therefore will not be repeated for the sake of brevity.

In the example of FIGS. 27A-27F, the robotic arm 210-6 is in a docked state (e.g., docked position). It is possible for nullspace motion to be activated on the robotic arm 210-6 (e.g., due to the robotic arm 210-6 having one or more extra degrees of freedom). Furthermore, motion of the robotic arm 210-6 will not cause collision (e.g., with other robotic arms and/or instruments).

Referring to FIGS. 27A and 27B, a comparison between these figures (using a line 718 drawn across the base joint 304-1-6 of the robotic arm 210-6 as reference) shows that the base joint 304-1-6 of the robotic arm 210-6 has moved relative to the stationary patient support platform 202 (e.g., in the positive y-direction).

In some embodiments, and as illustrated in FIG. 27B, the movement of the base joint 304-1-6 does not lead to movement of the ADM and/or RCM of the robotic arm 210-6 due to extra degree(s) of freedom on the robotic arm 210-6 from one or more redundant joints (e.g., one or more of the joints 304-2, 304-3, 304-4, and 304-5 in FIG. 23A), which enable the robotic arm 210-6 to move in a null space to both maintain the pose of the ADM and a position of an RCM and avoid collision(s) with other robotic arms or objects, thereby maintaining the position and/or the orientation of the medical tool 212-2.

Figure 27F:
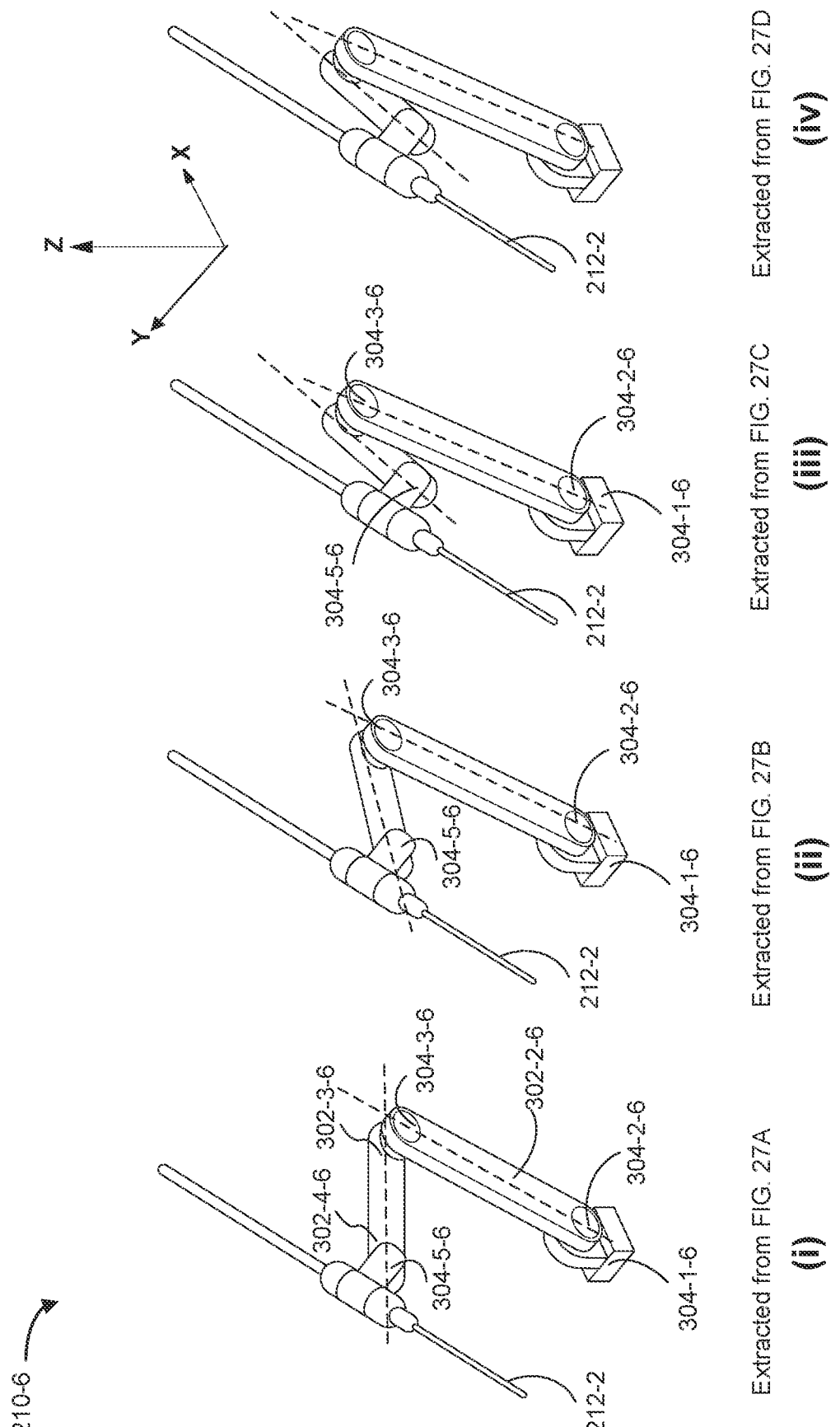

FIGS. 27F(i) and 27F(ii) illustrate the change in pose of the robotic arm 210-6 as it executes nullspace motion to hold its RCM. In some embodiments, due to movement of the base joint 304-1-6 in the positive y-direction, the robotic arm 210-6 can rotate one or more joints (e.g., one or more redundant joints, such as the joint 304-2-6 and/or an elbow joint 304-3-6), which in turn change a position and/or orientation of the link(s) 302-2-6, 302-3-6, and/or 302-4-6, so as to maintain the position and/or orientation of the instrument 212-2. Thus, the robotic system 200 is able to maintain the poses of the ADM 308 of the robotic arm 210-6 and the medical tool 212-2, even when there is movement (e.g., via the shared DoFs) between the robotic arm 210-6, the base joint 304-1-6, and the bar 220-2.

FIG. 27B also illustrates that the robotic arm 210-5 is in an undocked state. The robotic arm 210-5 is also not at its A0 joint limit (e.g., base joint limit). This situation corresponds to Step 532 in FIG. 25B. In some embodiments, in accordance with a determination that the robotic arm 210-5 is not at its A0 joint limit, the processors of the robotic system 200 determine whether motion of the robotic arm 210-5 will cause collision (Step 534). In this example, because the base joint 304-1-6 of the robotic arm 210-6 is moving toward the robotic arm 210-5, keeping the robotic arm 210-5 stationary relative to the base 206 of the robotic system 200 can lead to collision between the robotic arm 210-5 and the robotic arm 210-6 (Step 542). Consequently, in this scenario, the robotic arm 210-5 "sits on" (e.g., couples to) the bar 220-2 and moves together with (e.g., in the same direction as) the bar 220-2 in order to minimize likelihood of collision with the robotic arm 210-6 (544).

Using a line 722 drawn across the base joint 304-1-5 of the robotic arm 210-5 as a reference, a comparison between FIGS. 27A and 27B shows movement of the robotic arm 210-5 with the bar 220-2 in the same direction. In some embodiments, the robotic arm 210-5 and the bar 220-2 move collectively (e.g., at the same speed and direction). In some embodiments, the robotic arm 210-5 may move in the same direction as the bar 220-2 but at a different speed (e.g., faster or slower). In some embodiments, the processors may also adjust the speed of the robotic arm 210-5 such that the robotic arm 210-5 moves and does not collide with adjacent robotic arms and/or tools 212.

FIG. 27C shows further translation of the bar 220-1 in the negative y direction (e.g., toward the head). In some embodiments, and as discussed above with respect to FIG. 25A, the continued translation of the bar 220-1 is in accordance with a determination (e.g., by the processors) that the bar 220-1 has not reached its limit of translation (e.g., D7 translation) (Step 523, FIG. 25A) and in accordance with a determination that the robotic arm 210-3 is in a manual manipulation mode (e.g., admittance nullspace, or impedance mode) (Step 515, FIG. 25A). In accordance with the bar 220-1 movement, the distance between the second end 704 of the bar 220-1 and the second end 712 of the patient support platform 202 decreases from H2 (724) in FIG. 27B to H3 (728) in FIG. 27C.

In the example of FIG. 27C, the robotic arm 210-1 has reached the A0 joint limit (Step 540, FIG. 25B). As a result, the robotic arm 210-1 moves with the bar 220-1 in the same direction (e.g., with the same velocity) (Step 544, FIG. 25B). The robotic arm 210-2 continues its motion via nullspace to maintain the position/orientation of the tool 212-1.

FIG. 27C also illustrates further translation of the bar 220-2 in the positive y direction (e.g., toward the legs of the patient support platform 202). In some embodiments, the bar 220-1 translation is in accordance with a determination that the bar 220-2 has not reached its D7 limit (Step 523), the robotic arm 210-6 is in admittance nullspace or impedance mode (Step 515), and the robotic arm 210-6 is still within the cutoff limit (Step 513), as discussed previously with respect to FIG. 25A.

FIG. 27C further illustrates continued translation of the robotic arm 210-5 (e.g., the base joint 304-1-5) and the robotic arm 210-6 (e.g., the base joint 304-1-6) in the same direction as the bar 220-2. The robotic arm 210-6 continues to move in nullspace to maintain the position/orientation of the medical tool 212-2 (e.g., by moving the joint 304-3-6 and/or the joint 304-5-6). FIG. 27F(iii) shows that the nullspace motion in this case includes movement in the joint 304-3-6 and/or the joint 304-5-6, to cause a tilt in the link(s) between these joints in a downward direction.

FIG. 27D illustrates further translation of the bar 220-1 from FIG. 27C. In this example, the continued movement of the robotic arm 210-1 with the bar 220-1 and the continued movement of the robotic arm 210-2 in nullspace may cause collision between the arm 210-1 and the arm 210-2 (e.g., the tool 212-1), as denoted by the shaded portions in FIG. 27D. In some embodiments, in accordance with a determination that the arm motion would cause collision, the processors stop bar motion (Step 562, FIG. 25B).

In some embodiments, continued translation of the bar 220-2 in the positive y direction may result in the bar 220-2 reaching its limit of translation (e.g., D7 limit) (Step 521, FIG. 25A). In this situation, the processors will stop the motion of the bar 220-2 and the robotic arms 210-4, 210-5, and 210-6 (Step 522, FIG. 25A).

FIG. 27E illustrates the respective poses of the robotic arm 210-2 during nullspace motion, so that the RCM holds its position and maintains the orientation and/or position of the instrument 212-1.

FIG. 27F illustrates the respective poses of the robotic arm 210-6 during nullspace motion, so that the RCM holds its position and maintains the orientation and/or position of the instrument 212-1.

F. Example Methods of Controlling Motion of Kinematic Chains

Figure 28A:
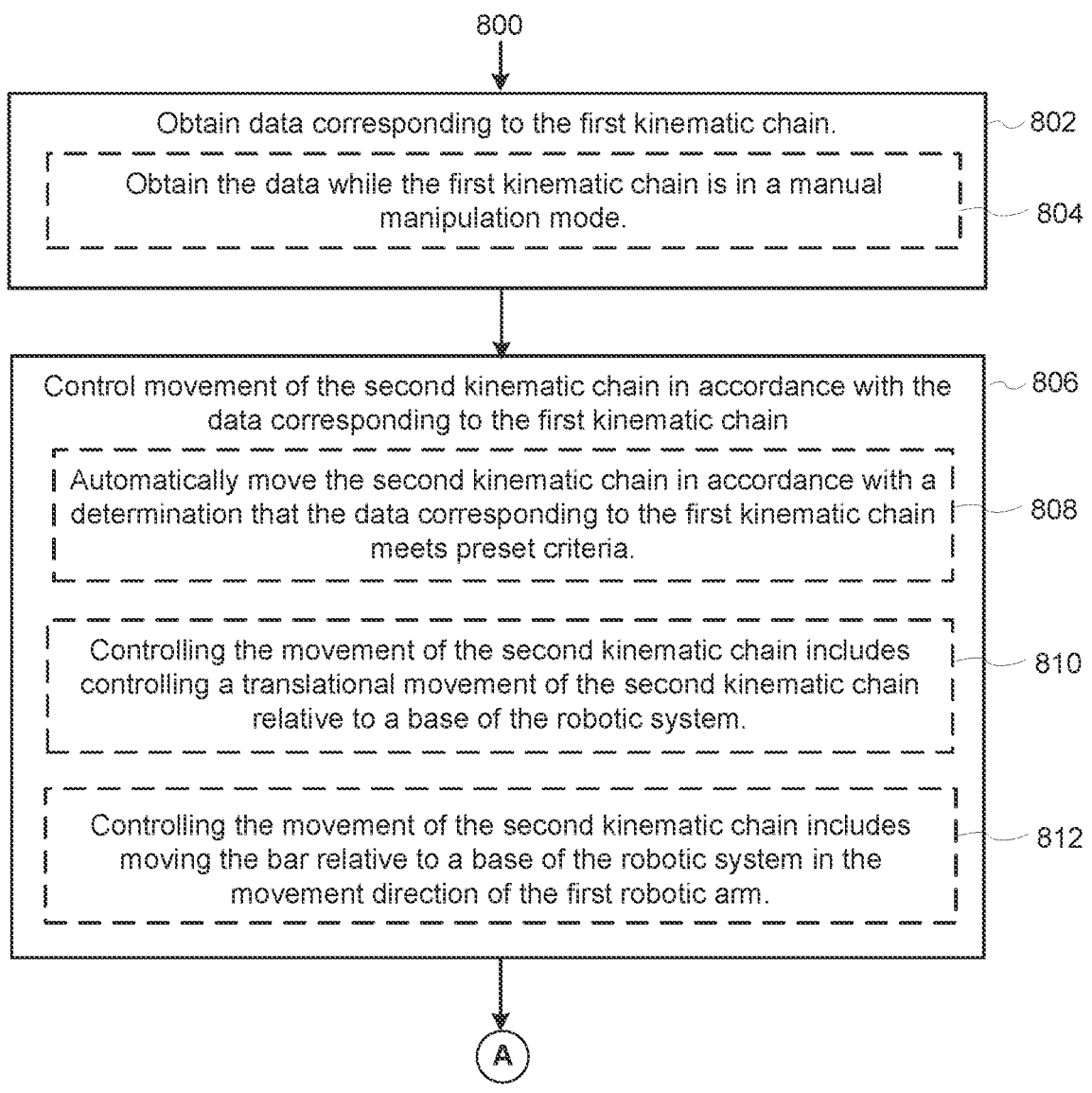
FIGS. 28A and 28B illustrate a flowchart diagram of a method for setting up a robotic medical system according to some embodiments.
Figure 28B:
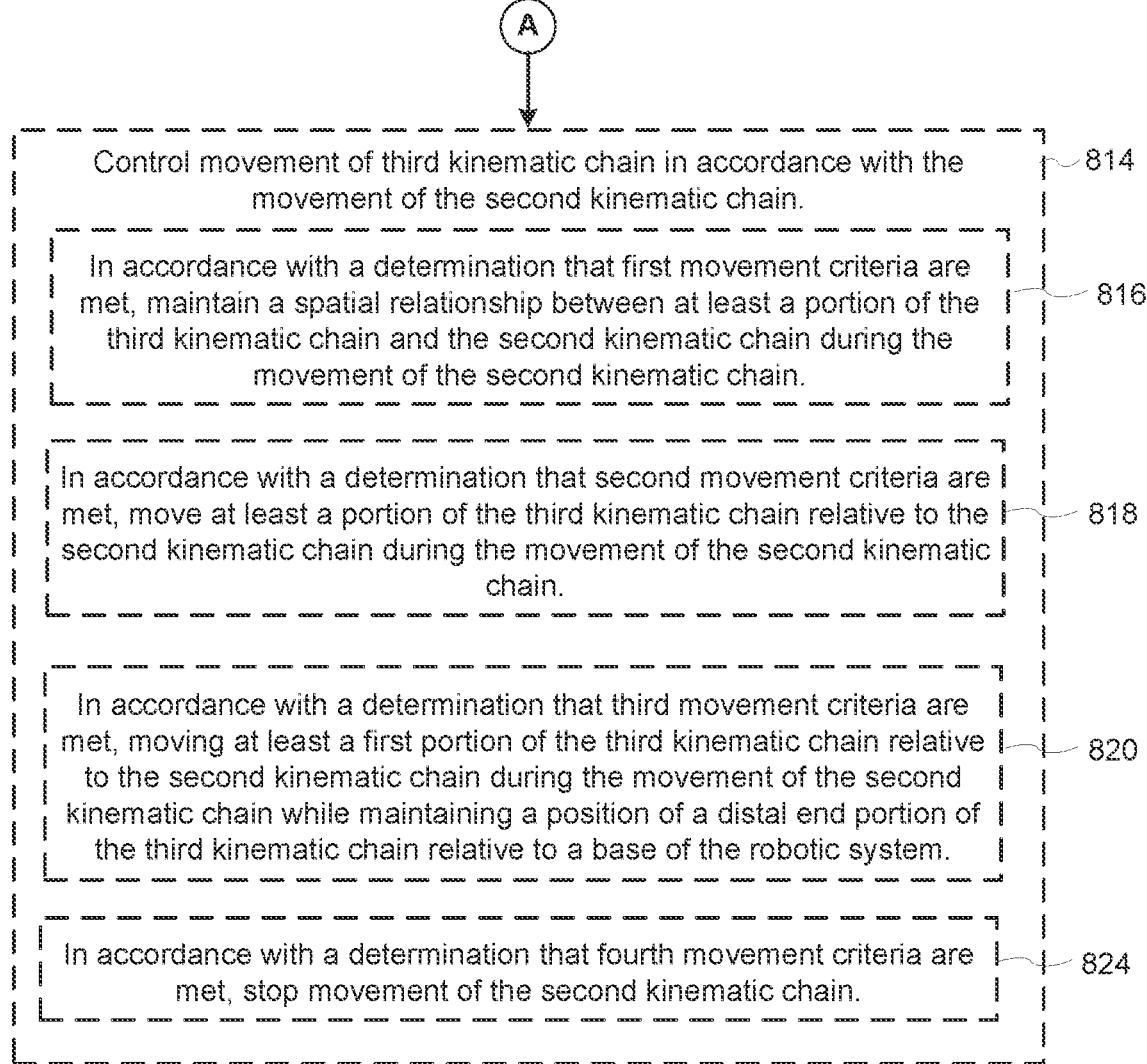

FIGS. 28A and 28B illustrate a flowchart diagram of a method 800 according to some embodiments. In some embodiments, the method 800 is performed by one or more processors of a robotic system.

In one aspect of the present disclosure, the robotic system includes a robotically controlled first kinematic chain. For example, the first kinematic chain is a first robotic arm (e.g., the robotic arm 210-3 in FIG. 26A, the robotic arm 210-3 in FIG. 27A, or the robotic arm 210-4 in FIG. 27A). In some embodiments, the robotic system (e.g., robotic system 200, as illustrated in FIGS. 21, 22, 26, and 27) is a robotic surgery system and the first kinematic chain includes a robotic arm configured to hold a surgical tool (e.g., a scope and/or instrument) during surgery (e.g., robotic arm 210-2 holding a surgical tool 212-1, FIG. 27A).

The robotic system also includes a robotically controlled second kinematic chain that is movably coupled to the first kinematic chain. For example, the second kinematic chain is a bar (e.g., bar 220-1, FIG. 27A) coupled to the first robotic arm (e.g., the robotic arm 210-3) and one or more other robotic arms (e.g., the robotic arms 210-1 and 210-2 in FIG. 27A).

The robotic system 200 further includes a controller (e.g., controller 182, FIG. 19, another controller that is used by the robotic medical system 200, a combination of multiple controllers, etc.) that is communicably coupled to the first kinematic chain and the second kinematic chain.

The controller includes one or more processors and memory. The memory stores instructions that, when executed by the one or more processors, cause the processors to obtain (802) data corresponding to the first kinematic chain. For example, the data corresponding to the first kinematic chain may include a force, torque, and/or momentum corresponding to the first kinematic chain. The data may also include a location of the first kinematic chain, or distance travelled by the first kinematic chain. For example, in FIGS. 26A and 26B, the processors obtain data corresponding to the robotic arm 210-3, including a starting location and/or a distance traveled by the robotic arm 210-3 along the bar 220-1. The processors can also obtain force, torque, and/or momentum data corresponding to the first kinematic chain 210-3.

In some embodiments, obtaining the data corresponding to the first kinematic chain includes obtaining (804) the data while the first kinematic chain is in a manual manipulation mode. In some embodiments, the manual manipulation mode is a pure manual manipulation mode. The manual manipulation mode may also comprise a power-assisted manual manipulation mode, such as an impedance control mode or admittance control mode. The manual manipulation mode may also comprise powered motion that is controlled by user input specifically directed to the first kinematic chain via a control device (e.g., a button, a joystick, etc.).

In some embodiments, the instructions, when executed by the one or more processors, also cause the processors to control (806) movement of the second kinematic chain in accordance with the data corresponding to the first kinematic chain. In some embodiments, controlling movement of the second kinematic chain may include initiating and/or stopping automatic translational movement of the second kinematic chain. For example, in FIG. 26C, controlling movement of the second kinematic chain (e.g., the bar 220-1) may include initiating automatic translational movement of the bar 220-1. For example, in FIG. 27D, controlling movement of the second kinematic chain (e.g., the bar 220-1 or the bar 220-2) may include stopping automatic translational movement of the bar 220-1 or the bar 220-2. In some embodiments, the processors may initiate movement for purposes other than avoiding or resolving distortion and/or impact from the first kinematic chain.

In some embodiments, controlling the movement of the second kinematic chain in accordance with the data corresponding to the first kinematic chain includes automatically moving (808) the second kinematic chain in accordance with a determination that the data corresponding to the first kinematic chain meets preset criteria. In some embodiments, automatically moving the second kinematic chain includes using one or more motors to cause the automatic motion. In some embodiments, the processors automatically move the second kinematic chain in accordance with a determination that a current position of the base joint of the first kinematic chain is beyond a cutoff position along the second kinematic chain for more than a threshold amount of time. For example, in FIG. 27B, the processors automatically move the bar 220-2 in accordance with a determination that a current position of the base joint of the arm 210-4 is beyond a cutoff position along the bar 220-2 for more than a threshold amount of time. As another example, in FIG. 27B, the processors automatically move the bar 220-1 in accordance with a determination that a current position of the base joint of the arm 210-3 is beyond a cutoff position along the bar 220-2 for more than a threshold amount of time. This is also illustrated in the bar auto translation algorithm (Step 514) in FIG. 25A. In some embodiments, the processors automatically move the second kinematic chain in accordance with a determination that an electrical current in the first kinematic chain exceeds a threshold current. In some embodiments, the processors automatically move the second kinematic chain in accordance with a determination that a speed of a preset portion of the first kinematic chain exceeds a threshold speed, and/or a force on a joint in the first kinematic chain (e.g., a joint other than the base joint of the first robotic arm on the bar) is above a threshold force.

In some embodiments, controlling the movement of the second kinematic chain includes controlling (810) a translational movement of the second kinematic chain relative to a base of the robotic system. For example, in FIG. 27C, controlling the movement of the bar 220-2 includes controlling (810) a translational movement of the bar 220-2 relative to a base 206 of the robotic system 200. In some embodiments, the translational movement of the second kinematic chain may include starting a translational movement of the second kinematic chain, stopping a translational movement of the second kinematic chain, and/or controlling a distance traveled by the second kinematic chain.

In some embodiments, the first kinematic chain includes a first robotic arm. For example, the first kinematic chain may include the first arm (e.g., the robotic arm 210-1 in FIG. 27), the last arm (e.g., the robotic arm 210-6 in FIG. 27), or an arm other than the first arm or the last arm (e.g., any of the robotic arms 210-2 to 210-5 in FIG. 27). In some embodiments, the second kinematic chain includes a bar (e.g., bar 220-1 or bar 220-2, FIG. 27) that supports the first robotic arm.

In some embodiments, the first robotic arm includes a base joint (e.g., base joint 304-1, FIG. 23) that is coupled to the bar and capable of translating along the bar. For example, before a joint limit is reached, the base joint exerts a negligible amount of force in a direction along the bar when the first robotic arm is being pushed along the bar while the bar is kept stationary relative to the base of the robotic system.

In some embodiments, the translation of the first robotic arm along the bar is constrained by a first limit along the bar. For example, the translation of the first robotic arm includes a translation of the base joint (e.g., base joint 304-1, FIG. 23) of the first robotic arm along the bar. In some embodiments, the first limit is the base joint limit near the end of the bar (e.g., joint limit 404 in FIG. 24A or joint limit 412 in FIG. 24D). In some embodiments, the first limit is a haptic wall for the first robotic arm along the bar.

In some embodiments, the first limit includes a haptic wall that limits an extent of manual translation of the first robotic arm along the bar. For example, the manual translation includes a user directly pushing on the first robotic arm, and/or moving the first robotic arm using a button or control device, etc.

In some embodiments, automatic movement of the bar is triggered in accordance with a cutoff limit being exceeded by the first robotic arm. In some instances, automatic movement of the bar is triggered in accordance the first robotic arm being held within the cutoff for a certain time period (e.g., Step 512, FIG. 25A). In some embodiments, the cutoff limit may comprise a positional threshold that precedes the base joint limit or a haptic wall in a first movement direction of the first robotic arm along the bar. For example, in FIG. 24A, the cutoff limit 402 includes a positional threshold that precedes the base joint limit 404. The cutoff limit may also comprise, another type of threshold that is based on speed, current, force, etc.

In some embodiments, the data corresponding to the first kinematic chain includes a distance travelled by the first robotic arm along the bar. For example, the distance travelled by the first robotic arm includes a distance traveled by the base joint of the first robotic arm. In some embodiments, the distance traveled by the first robotic arm is used to calculate the current position of the first robotic arm along the bar; and the current position of the first robotic arm is used to determine whether the cutoff limit has been reached or exceeded.

In some embodiments, the data corresponding to the first kinematic chain includes a movement direction of the first robotic arm along the bar. In some embodiments, the movement direction of the first robotic arm includes a movement direction of the base joint of the first robotic arm along the bar. Controlling the movement of the second kinematic chain includes moving (812) the bar relative to a base of the robotic system in the movement direction of the first robotic arm. For example, the first robotic arm and the bar may move in the same direction (e.g., with the same speed, with different speeds, etc.) relative to the base of the robotic system. For example, in FIG. 26A, the data corresponding to the robotic arm 210-3 includes a movement direction of the robotic arm 210-3 along the bar 220-1 (e.g., toward the second end 603). Controlling the movement of the second kinematic chain (e.g., the bar 220) includes moving the bar 220 relative to a base 206 of the robotic system 200 in the movement direction of the first robotic arm 210-3 (e.g., in the negative y direction).

In some embodiments, the robotic system 200 further includes a robotically controlled third kinematic chain that is movably coupled to the second kinematic chain. For example, the third kinematic chain may be a second robotic arm, or a third robotic arm, such as the robotic arms 210-1, 210-2, 210-5 or 210-6 in FIG. 27.

In some embodiments, the first kinematic chain and the third kinematic chain are both capable of translating along the second kinematic chain, while exerting an negligible amount of force on the second kinematic chain in a direction along the second kinematic chain, and vice versa. In some embodiments, the instructions, when executed by the one or more processors, cause the processors to control (814) movement of the third kinematic chain in accordance with the movement of the second kinematic chain. For example, controlling the movement of the third kinematic chain may comprise initiating and/or stopping automatic translational movement of the third kinematic chain. In some embodiments, the controlling movement of the third kinematic chain is in accordance with the movement of the second kinematic chain and in accordance with the movement of the first kinematic chain, e.g., to avoid collision with the first kinematic chain, and/or maximize workspace, etc.

As illustrated in FIG. 27, the robotic system 200 further includes a robotically controlled third kinematic chain (e.g., the robotic arm 210-1) that is movably coupled to the second kinematic chain (e.g., the bar 220-1), in accordance with some embodiments. In some embodiments, the instructions, when executed by the one or more processors, cause the processors to control movement of the robotic arm 210-1 in accordance with the movement of the bar 220-1.

In some embodiments, the first kinematic chain includes a first robotic arm. The third kinematic chain includes a second robotic arm. The second kinematic chain includes a bar that supports the first robotic arm and the second robotic arm.

For example, FIG. 27, the first kinematic chain includes a first robotic arm 210-4, in accordance with some embodiments. The third kinematic chain includes a second robotic arm 210-5, in accordance with some embodiments. The second kinematic chain includes a bar 220-2 that supports the first robotic arm 210-4 and the second robotic arm 210-5, in accordance with some embodiments.

In some embodiments, controlling the movement of the third kinematic chain in accordance with the movement of the second kinematic chain includes: in accordance with a determination that first movement criteria are met, maintaining (816) a spatial relationship between at least a portion of the third kinematic chain and the second kinematic chain (e.g., the bar) during the movement of the second kinematic chain. In some embodiments, the first movement criteria comprise: the second robotic arm is undocked, the joint limit or the cutoff for the second robotic arm has been reached, the second robotic arm will not cause collision, etc. The at least a portion of the third kinematic chain may include a base joint of the second robotic arm, the base joint and one or more additional portions of the second robotic arm, the second robotic arm as a whole, etc. In some embodiments, maintaining a spatial relationship between at least a portion of the third kinematic chain and the second kinematic chain during the movement of the second kinematic chain includes moving the second robotic arm with the bar in the same direction during the automatic translation of the bar.

For example, in some embodiments, as illustrated in FIGS. 26D and 26E, the third kinematic chain includes the robotic arm 210-1 and the second kinematic chain includes the bar 220-1. In some instances, controlling the movement of the robotic arm 210-1 in accordance with the movement of the bar 220-1 includes: in accordance with a determination that first movement criteria are met (e.g., the robotic arm 210-1 is undocked, the joint limit for the bar 220-1 has been reached, and/or movement of the robotic arm 210-1 will not cause collision), maintaining a spatial relationship (e.g., a distance E3 (618)) between at least a portion of the robotic arm 210-1 and the bar 220-1 during the movement of the bar 220-1.

In some embodiments, controlling the movement of the third kinematic chain in accordance with the movement of the second kinematic chain includes: in accordance with a determination that second movement criteria are met, moving (818) at least a portion of the third kinematic chain relative to the second kinematic chain (e.g., the bar) during the movement of the second kinematic chain. In some embodiments, the second movement criteria comprise: second robotic arm is undocked, the joint limit or the cutoff for the second robotic arm has not been reached, will not cause collision, etc. The at least a portion of the third kinematic chain may include a base joint of the second robotic arm, the base joint and one or more additional portions of the second robotic arm, the second robotic arm as a whole, etc. In some embodiments, the base joint of the second robotic arm does not move with the bar during the automatic translation of the bar, and maintains its absolute position relative to the base of the robotic system. Stated another way, the base joint of the second robotic arm moves in a direction that is opposite from the direction of the bar motion. For example, as illustrated in the transition from FIG. 26B to FIG. 26C, when the robotic arm 210-1 is in undocked position and the joint limit not yet reached, the robotic arm 210-1 stays put relative to the base 206 while the bar 220-1 moves. This is also discussed in FIG. 25B.

In some embodiments, controlling the movement of the third kinematic chain in accordance with the movement of the second kinematic chain includes: in accordance with a determination that third movement criteria are met, moving (820) at least a first portion of the third kinematic chain relative to the second kinematic chain (e.g., the bar) during the movement of the second kinematic chain while maintaining a position of a distal end portion of the third kinematic chain relative to a base of the robotic system. In some embodiments, the third movement criteria comprise: the second robotic arm is docked, or nullspace motion is available to the second robotic arm and the nullspace motion will not cause collision, etc. The at least a first portion of the third kinematic chain may include a base joint of the second robotic arm, the base joint and one or more additional portions of the second robotic arm, etc. For example, one or more joints, including the base joint, of the second robotic arm may move with the bar or relative to the bar during the translation of the bar, to keep the remote center of motion stationary relative to the base or table of the robotic system.

For example, in some embodiments, in FIG. 27, the third kinematic chain includes the robotic arm 210-2 and the second kinematic chain includes the bar 220-1. Controlling the movement of the robotic arm 210-2 in accordance with the movement of the bar 220-1 includes: in accordance with a determination that the robotic arm 210-1 is docked (Step 546, FIG. 25B), nullspace motion is available to the robotic arm 210-1 (Step 548, FIG. 25B), and the nullspace motion will not cause collision (Step 554, FIG. 25B), moving at least a first portion of the robotic arm 210-1 relative to the bar 220-1 during the movement of the bar 220-1 while maintaining a position of a distal end portion of the robotic arm 210-1 relative to a base 206 of the robotic system 200 (e.g., to maintain an orientation and/or position of the tool 212-1).

In some embodiments, controlling the movement of the second kinematic chain (e.g., the bar) in accordance with the movement of the first kinematic chain (e.g., the first robotic arm) includes in accordance with a determination that fourth movement criteria are met, stopping (824) movement of the second kinematic chain. In some embodiments, the fourth movement criteria includes: the first arm is no longer in cutoff zone, bar motion limit is reached, the manual manipulation mode is ended, the second arm docked but nullspace motion is not available, and/or bar motion will cause collision, etc. In some embodiments, when the bar motion is stopped, other motions (e.g., motions of the second robotic arm, and the third robotic arm, etc.) triggered by the bar motion is also stopped.

For example, in some embodiments, in FIG. 27D, movement of the second kinematic chain (e.g., the bar 220-1) is stopped in accordance with a determination that motion of the bar 220-1 will cause collision between the robotic arms 210-1 and 210-2 (Step 562, FIG. 25B). As another example, in FIG. 27D, movement of the bar 220-2 is stopped in accordance with a determination that the bar 220-2 has reached its limit of translation (Step 521, FIG. 25B).

FIG. 29 illustrates a flowchart diagram of a method 900 according to some embodiments. In some embodiments, the method 900 is performed by one or more processors of a robotic system 200 (e.g., a robotic medical system 200) in accordance with instructions stored on memory of the robotic system 200.

In some embodiments, a robotic medical system 200 includes a patient support platform (e.g., patient support platform 202, as illustrated in FIGS. 21, 22, 26, and 27). In some embodiments, the patient support platform includes a table, a bed, etc.

The robotic medical system 200 includes a first kinematic chain. For example, the first kinematic chain is a first robotic arm (e.g., robotic arm 210-3, FIG. 26 or robotic arm 210-4, FIG. 27), in accordance with some embodiments.

The robotic medical system also includes a second kinematic chain. For example, the second kinematic chain is a bar (e.g., bar 220-1 in FIG. 26 or bar 220-2 in FIG. 27), a second robotic arm (e.g., robotic arm 210-6 in FIG. 27), etc., in accordance with some embodiments.

The first kinematic chain is movably coupled to the second kinematic chain. For example, the first kinematic chain (e.g., the robotic arm 210-3 in FIG. 26) is movably coupled to the second kinematic chain (e.g., the bar 220-1 in FIG. 26) through a base joint (e.g., base joint 304-1, FIG. 23) with one or more degrees of freedom, in accordance with some embodiments.

The robotic medical system 200 includes a controller (e.g., controller 182, FIG. 19, another controller that is used by the robotic medical system 200, a combination or multiple controllers, etc.). The controller includes one or more processors and memory. The memory stores instructions that, when executed by the one or more processors, cause the processors to adjust (902) a spatial configuration of the first kinematic chain relative to the patient support platform in accordance with user input directed to the first kinematic chain. In some embodiments, the adjusting includes a manual adjustment without power-assistance, power-assisted adjustment (e.g., impedance control, admittance control, etc.). In some embodiments, the adjusting includes an automatic adjustment according to user instruction, etc. In some embodiments, the spatial configuration of the first kinematic chain includes positions and/or orientations of joints and/or links of the first kinematic chain. In some embodiments, the user input directed to the first kinematic chain may comprise direct contact and/or force provided by a user on a link or joint of the first kinematic chain. The user input may also be through user activation of a user interface element corresponding to the first kinematic chain in a user interface of a control device, and/or through activation of a hardware control element on or attached to the first kinematic chain, etc.

In some embodiments, the first kinematic chain is movably coupled to the second kinematic chain via a base joint that is capable of translating along the second kinematic chain. Adjusting the spatial configuration (e.g., positions and/or orientations of joints and/or links) of the first kinematic chain relative to the patient support platform includes translating (904) at least the base joint of the first kinematic chain (e.g., the first robotic arm) along the second kinematic chain (e.g., the bar). This is illustrated in FIGS. 26A to 26B, for example.

In some embodiments, adjusting the spatial configuration of the first kinematic chain relative to the patient support platform in accordance with user input directed to the first kinematic chain includes: adjusting (906) the spatial configuration of the first kinematic chain in accordance with direct physical manipulation of the first kinematic chain by a user under a first power-assisted manipulation mode of the first kinematic chain. In some embodiments, the spatial configuration of the first kinematic chain includes positions and/or orientations of joints and/or links of the first kinematic chain. In some embodiments, direct physical manipulation of the first kinematic chain by a user may include the user physically moving, pushing, pulling, bending, twisting, etc. on one or more joint(s) and/or link(s) of the first kinematic chain. The first power-assisted manipulation mode of the first kinematic chain may include an impedance mode or an admittance mode.

The memory also stores instructions that, when executed by the one or more processors, cause the processors to: in accordance with a determination that preset criteria are met during adjustment of the spatial configuration of the first kinematic chain in accordance with the user input directed to the first kinematic chain, activate (908) automatic movement of the second kinematic chain relative to the patient support platform. In some embodiments, a determination that the preset criteria met are includes a determination that a cutoff limit is reached for more than a threshold amount of time. In some embodiments, a determination that the preset criteria are met includes a determination that a force on the first kinematic chain exceeds a threshold force. In some embodiments, a determination that the preset criteria met are comprises a determination that a speed of the first kinematic chain exceeds a threshold speed. In some embodiments, automatic movement of the second kinematic chain relative to the patient support platform includes automatic bar motion relative to the patient support platform. Optionally, in accordance with the automatic bar motion, a spatial configuration of the first kinematic chain may change relative to the patient support platform and/or relative to the second kinematic chain.

In some embodiments, activating the automatic movement of the second kinematic chain relative to the patient support platform includes automatically translating (910) the second kinematic chain relative to the patient support platform.

In some embodiments, the first kinematic chain includes a first robotic arm. The second kinematic chain includes a bar that supports the first robotic arm. This is illustrated in FIGS. 26 and 27, for example.

In some embodiments, the user input directed to the first kinematic chain is received via an input interface located on or proximate to the first kinematic chain. For example, the input interface may comprise a hardware button, touch and/or force sensors, a graphical user interface on a control device, etc. In some embodiments, the input interface is separated from, not on or proximate to, the second kinematic chain. In some embodiments, there is, optionally, another input interface for directly controlling the bar motion that is on or proximate to the bar, or on a separate device away from the patient support platform.

In some embodiments, the user input directed to the first kinematic chain includes an input received (912) via a button. In some embodiments, the button is located on the first kinematic chain (e.g., on the side or top of a link of the first robotic arm) (e.g., button 312 or button 314, FIG. 23). A user activates (e.g., engages, holds, presses) the button to trigger and maintain the manual manipulation. In some embodiments, the user input is received via a graphical user interface of a software program that is displayed on a control panel that is part of or in communication with the robotic medical system.

In some embodiments, the input received via the button is (914) a continuous user input. For example, the user presses (or presses and holds) the button (e.g., the button 314 in FIG. 23B) on the first kinematic chain in order to enable continued manual manipulation. In some embodiments, impedance could be activated by one press and deactivated by another press, rather than a continuous activation.

In some embodiments, the instructions, when executed by the one or more processors, cause the processors to deactivate (916) the automatic movement of the second kinematic chain relative to the patient support platform in accordance with a determination that the continuous user input ceases to be detected via the button. In some embodiments, deactivating the automatic movement of the second kinematic chain includes stopping automatic bar motion relative to the patient support platform. In some embodiments, the continuous user input ceases to be detected when the user is no longer holding and/or pressing on the button (e.g., the button 314 in FIG. 23B), e.g., even if the user continues to push or pull on the link(s) or joint(s) of the first kinematic chain.

In some embodiments, the preset criteria require that a force detected on one or more preset portions of the first kinematic chain exceeds a preset threshold force during the adjustment of the spatial configuration of the first kinematic chain in order for the preset criteria to be met. For example, as described in FIG. 23, the robotic arm 210 may comprise one or more sensors. A force may detected on one or more preset portions (e.g., links 302 and/or joints 304) of the first kinematic chain using contact sensors on the first robotic arm, via force and torque sensors on the joints of the first robotic arm, etc.. In some embodiments, the preset threshold force may comprise a first force threshold that is greater than a nominal force/contact detection force threshold. In some embodiments, the adjustment of the spatial configuration of the first kinematic chain may comprise a pure manual adjustment or a power-assisted adjustment.

Figure 30B:
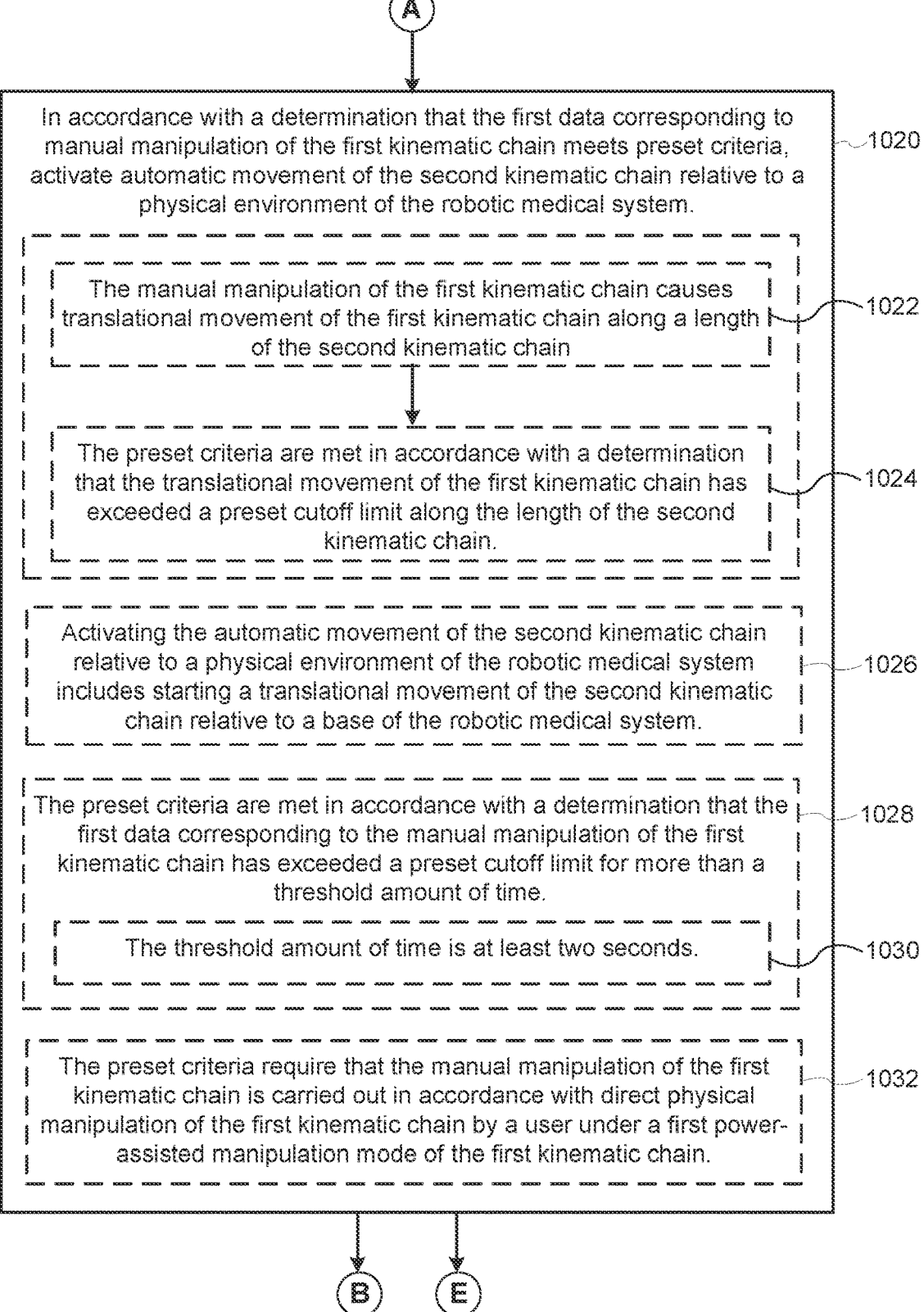
Figure 30C:
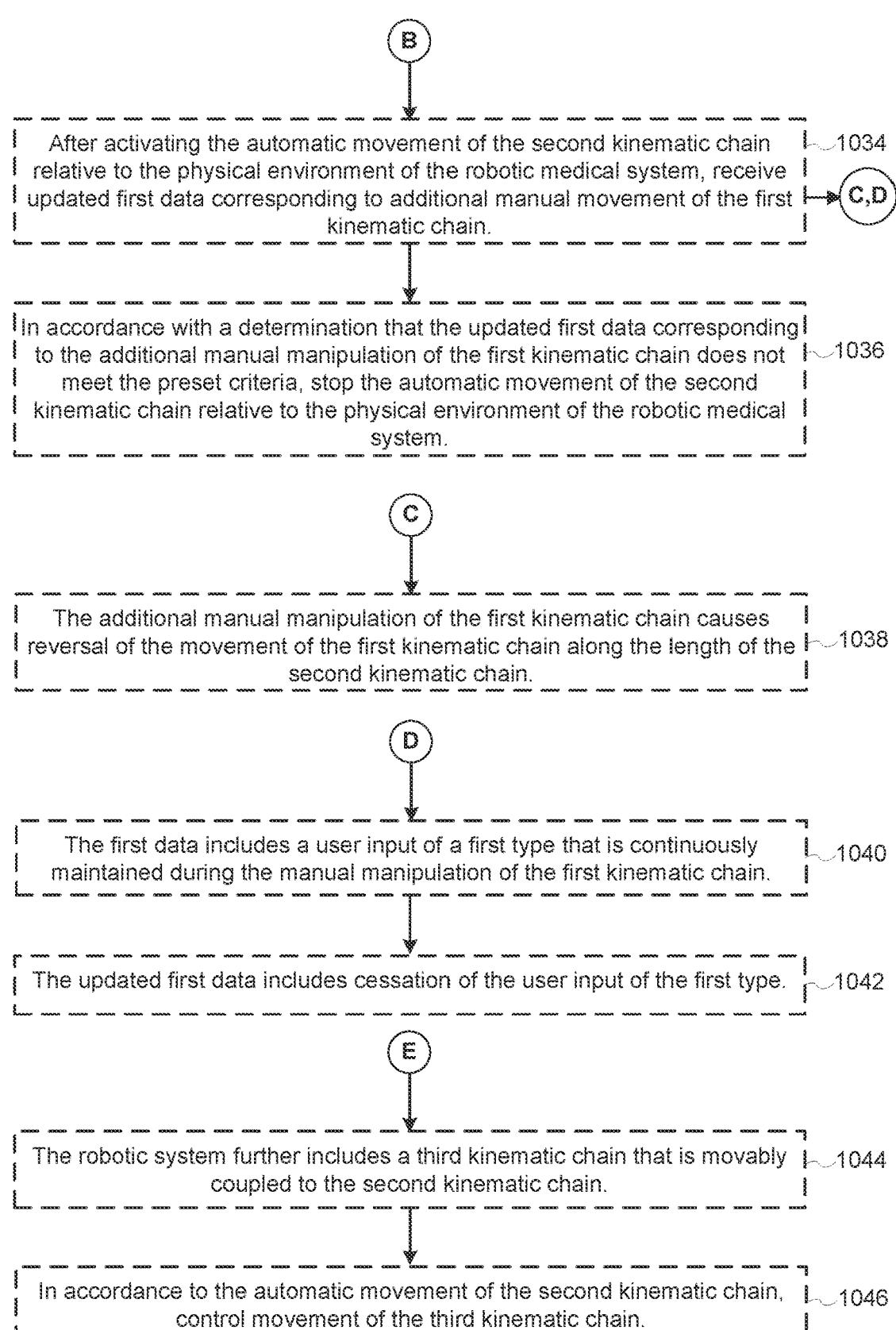

FIGS. 30A-30C are a flowchart diagram for a method 1000 for setting up (1002) a robotic medical system (e.g., the robotic medical system 200 as illustrated in FIGS. 21, 22, 26, and 27) according to some embodiments. In accordance with some embodiments of the present disclosure, the method 1000 is performed by one or more processors of the robotic medical system 200.

The robotic medical system 200 includes (1004) a first kinematic chain. For example, the first kinematic chain is a first robotic arm, such as robotic arm 210-3 or the robotic arm 210-4 in FIG. 27, in accordance with some embodiments. In some embodiments, the robotic medical system 200 is a robotic surgery system and the first kinematic chain includes a first robotic arm configured to hold a surgical tool (e.g., tool 212 in FIGS. 21 and 27) during surgery, in accordance with some embodiments.

The robotic medical system includes (1006) a second kinematic chain. The second kinematic chain is (1008) movably coupled to the first kinematic chain. In some embodiments, and as illustrated in FIG. 27, the second kinematic chain includes a bar or an arm support (e.g., bar 220-1 or bar 220-2, FIG. 27) coupled to the first robotic arm and one or more other robotic arms, etc. The first kinematic chain (e.g., the first robotic arm) and the second kinematic chain are coupled by a joint (e.g., base joint 304-1, FIG. 23) with one or more degrees of freedom, in accordance with some embodiments.

In some embodiments, the first kinematic chain includes (1010) a first robotic arm. The second kinematic chain includes (1012) a bar that supports the first robotic arm. For example, in FIG. 27, the first kinematic chain is a robotic arm 210-3. The second kinematic chain includes a bar 220-1 that supports the robotic arm 210-3, in accordance with some embodiments.

The robotic medical system 200 obtains (1014) first data corresponding to manual manipulation of the first kinematic chain. The manual manipulation of the first kinematic chain causes (1016) movement of the first kinematic chain relative to the second kinematic chain. For example, in FIG. 26, the robotic medical system 200 obtains first data corresponding to manual manipulation of the robotic arm 210-3. The manual manipulation of the robotic arm 210-3 causes movement of the robotic arm 210-3 relative to the bar 220-1.

In some embodiments, the first data may include data corresponding to a force, speed, movement distance, etc. corresponding to the manual manipulation of the first kinematic chain. In some embodiments, manual manipulation includes manipulation under a pure manual manipulation mode. In other embodiments, manual manipulation may comprise a power-assisted manual manipulation mode, such as an impedance control mode, an admittance control mode, and/or controlled motion executed in accordance with user input directed to the first kinematic chain that has been received via a control device (e.g., button, a joystick, etc.

In some embodiments, the movement of the first kinematic chain relative to the second kinematic chain may comprise a translational movement of the base joint (e.g., the base joint 304-1) connecting the first kinematic chain and the second kinematic chain.

In some embodiments, the manual movement of the first kinematic chain along the second kinematic chain is (1018) constrained by a first limit along the second kinematic chain. For example, the first kinematic chain is a first robotic arm. The manual movement of the first kinematic chain includes a translation of a base joint of the first robotic arm along the bar. The first limit is the base joint limit near the end of the bar (e.g., joint limit 404 in FIG. 24A or joint limit 412 in FIG. 24D), a haptic wall for the first robotic arm along the bar, etc., in accordance with some embodiments.

In some embodiments, in accordance with a determination that the first data corresponding to manual manipulation of the first kinematic chain meets preset criteria, the robotic medical system 200 (e.g., via the one or more processors) activates (1020) automatic movement of the second kinematic chain relative to a physical environment of the robotic medical system 200. For example, this is illustrated in FIGS. 26C, 26D, and 26E.

In some embodiments, the preset criteria are met when movement of the first kinematic chain (e.g., the robotic arm) causes the first kinematic chain to exceed a cutoff limit along the second kinematic chain (e.g., the bar) for more than a threshold amount of time (e.g., 2 seconds, 3 seconds, or 5 seconds), as described in the bar translation algorithm in FIG. 25A, for example. In some embodiments, the preset criteria are met when a force on the first kinematic chain exceeds a threshold force, or when a speed of the first kinematic chain exceeds a threshold speed, etc. In some embodiments, automatic movement of the second kinematic chain relative to a physical environment of the robotic medical system includes automatic bar motion relative to the patient support platform. Optionally, in some embodiments, in accordance with the automatic movement of the second kinematic chain, the robotic medical system 200 also activates motion of the first kinematic chain and/or changes a spatial configuration of the first kinematic chain relative to the patient support platform. In some embodiments, in accordance with the automatic movement of the second kinematic chain, the robotic medical system 200 also activates motion of the first kinematic chain and/or changes a spatial configuration of the first kinematic chain relative to the second kinematic chain.

In some embodiments, the manual manipulation of the first kinematic chain causes (1022) translational movement of the first kinematic chain along a length of the second kinematic chain. The preset criteria are met (1024) in accordance with a determination that the translational movement of the first kinematic chain has exceeded a preset cutoff limit along the length of the second kinematic chain. In some embodiments, the preset cutoff limit includes a positional threshold that precedes the base joint limit or haptic wall along the bar.

For example, in FIG. 26A, the manual manipulation of the robotic arm 210-3 causes translational movement of the robotic arm 210-3 along a length of the bar 220-1. The preset criteria are met in accordance with a determination that the translational movement of the robotic arm 210-3 has exceeded a preset cutoff limit (e.g., D2 (612)) along the length of the bar 220-1.

In some embodiments, activating the automatic movement of the second kinematic chain relative to a physical environment of the robotic medical system includes starting (1026) a translational movement of the second kinematic chain relative to a base of the robotic medical system. For example, this is illustrated in FIGS. 26C, 26D, and 26E. In some embodiments, starting a translational movement of the second kinematic chain (e.g., the bar 220-1 or 220-2) includes starting and maintaining translation movement of the bar in the direction of the translation movement of the first robotic arm under manual manipulation.

In some embodiments, the preset criteria are met in accordance with a determination that the first data corresponding to the manual manipulation of the first kinematic chain has exceeded (1028) a preset cutoff limit for more than a threshold amount of time. For example, this is illustrated in Step 510 in FIG. 25A.

As one example, the first data includes a translational movement of the first kinematic chain. The preset criteria are met in accordance with a determination that the translational movement has exceeded a preset cutoff limit (e.g., a positional threshold that precedes the base joint limit or haptic wall along the bar) along the length of the second kinematic chain for more than three seconds. As another example, the first data includes a force corresponding to the manual manipulation of the first kinematic chain. The preset criteria are met in accordance with a determination that a force of more than a first force threshold has been maintained on the contact sensors on the links of the first kinematic chain for more than five seconds.

In some embodiments, the threshold amount of time is (1030) at least two seconds. In some embodiments, the threshold amount of time may be adjusted (e.g., to 1 second, 5 seconds, a value between 1-5 seconds, etc.).

In some embodiments, the preset criteria require that the manual manipulation of the first kinematic chain is (1032) carried out in accordance with direct physical manipulation of the first kinematic chain by a user under a first power-assisted manipulation mode of the first kinematic chain. For example, the direct physical manipulation may include a user physically moving, pushing, pulling, bending, and/or twisting on one or more joint(s) (e.g., joints 304, FIG. 23) and/or link(s) (e.g., links 302, FIG. 23) of the first kinematic chain. The first power-assisted manipulation mode may comprise an impedance mode or an admittance mode of the first kinematic chain.

In some embodiments, after activating the automatic movement of the second kinematic chain relative to the physical environment of the robotic medical system 200, the robotic medical system 200 (e.g., via the one or more processors) receives (1034) updated first data corresponding to additional manual movement of the first kinematic chain. In some embodiments, the activating the automatic movement of the second kinematic chain is in accordance with a determination that the preset criteria are met by the first data. The updated first data may include updated force, speed, and/or movement distance data corresponding to the additional manual movement of the first kinematic chain, in accordance with some embodiments.

In some embodiments, in accordance with a determination that the updated first data corresponding to the additional manual movement of the first kinematic chain does not meet the preset criteria, the robotic medical system 200 stops (1036) the automatic movement of the second kinematic chain relative to the physical environment of the robotic medical system.

For example, as illustrated in FIG. 25A, after the bar auto translation algorithm commences, the processors obtains updated data including whether the second kinematic chain (e.g., the bar) is at a translational limit, and/or whether the first kinematic chain (e.g., the robotic arm) is still in an admittance nullspace or impedance mode, and/or whether the first kinematic chain (e.g., the robotic arm) is still within a cutoff limit. In accordance with a determination the updated first data corresponding to the additional manual movement of the first kinematic chain does not meet the preset criteria, such as the bar is at the D7 limit (521), and/or the arm is not in admittance nullspace or impedance mode (517), and/or the arm is no longer within the cutoff limit (519), the robotic medical system 200 stops (522) the automatic movement of the second kinematic chain relative to the physical environment of the robotic medical system 200.

In some embodiments, the additional manual movement of the first kinematic chain causes (1038) reversal of the movement of the first kinematic chain along the length of the second kinematic chain. For example, in some embodiments, the preset criteria are no longer met when updated first data indicates that the reversal of the movement of the first kinematic chain along the length of the second kinematic chain has caused the first kinematic chain to exit the cut-off zone along the second kinematic chain.

In some embodiments, the first data includes (1040) a user input of a first type that is continuously maintained during the manual manipulation of the first kinematic chain. The updated first data includes (1042) cessation of the user input of the first type. For example, the user input of a first type includes a user pressing and holding a preset button (e.g., the button 314, FIG. 23B) on the first kinematic chain. The updated first data includes cessation of the user pressing and holding the preset button, in accordance with some embodiments.

In some embodiments, the robotic system 200 further includes a third kinematic chain that is movably coupled to the second kinematic chain. For example, the third kinematic chain is a second robotic arm or a third robotic arm, etc. In some embodiments, the first kinematic chain and the third kinematic chain are both capable of translating along the second kinematic chain, while exerting a negligible amount of force in a direction along the second kinematic chain, and vice versa. The method 1000 further includes: in accordance to the automatic movement of the second kinematic chain, controlling (1046) movement of the third kinematic chain, in accordance with some embodiments.

In some embodiments, controlling movement of the third kinematic chain includes initiating and/or stopping automatic translational movement of the third kinematic chain along the bar, and/or executing nullspace movement of link(s) and joint(s) of the third kinematic chain. This is illustrated in FIGS. 26 and 27. Optionally, the robotic medical system may control the movement of the third kinematic chain in accordance with the movement of the first kinematic chain (e.g., to avoid collision with the first kinematic chain, and/or maximize workspace, etc.).

3. Implementing Systems and Terminology

Embodiments disclosed herein provide systems, methods and apparatus for automatic bar translation while manipulating robotic arms.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for automatically commanding bar translation described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the embodiments shown herein but is to be accorded the widest scope consistent with the principles and novel features disclosed herein.

Some embodiments or implementations are described with respect to the following clauses:

Clause 1. A robotic system, comprising: a robotically controlled first kinematic chain; a robotically controlled second kinematic chain that is movably coupled to the first kinematic chain; and a controller that is communicably coupled to the first kinematic chain and the second kinematic chain, the controller including one or more processors and memory storing instructions, wherein the instructions, when executed by the one or more processors, cause the processors to: obtain data corresponding to the first kinematic chain; and control movement of the second kinematic chain in accordance with the data corresponding to the first kinematic chain.

Clause 2. The robotic system of clause 1, wherein obtaining the data corresponding to the first kinematic chain includes obtaining the data while the first kinematic chain is in a manual manipulation mode.

Clause 3. The robotic system of clause 1 or 2, wherein controlling the movement of the second kinematic chain in accordance with the data corresponding to the first kinematic chain includes automatically moving the second kinematic chain in accordance with a determination that the data corresponding to the first kinematic chain meets preset criteria.

Clause 4. The robotic system of any of clauses 1-3, wherein controlling the movement of the second kinematic chain comprises controlling a translational movement of the second kinematic chain relative to a base of the robotic system.

Clause 5. The robotic system of any of clauses 1-4, wherein: the first kinematic chain comprises a first robotic arm; and the second kinematic chain comprises a bar that supports the first robotic arm.

Clause 6. The robotic system of clause 5, wherein the first robotic arm comprises a base joint that is coupled to the bar and capable of translating along the bar.

Clause 7. The robotic system of clause 6, wherein the translation of the first robotic arm along the bar is constrained by a first limit along the bar.

Clause 8. The robotic system of clause 7, wherein the first limit includes a haptic wall that limits an extent of manual translation of the first robotic arm along the bar.

Clause 9. The robotic system of any of clauses 5-8, wherein automatic movement of the bar is triggered in accordance with a cutoff limit being exceeded by the first robotic arm.

Clause 10. The robotic system of any of clauses 5-9, where the data corresponding to the first kinematic chain includes a distance travelled by the first robotic arm along the bar.

Clause 11. The robotic system of any of clauses 5-10, wherein the data corresponding to the first kinematic chain includes a movement direction of the first robotic arm along the bar, and controlling the movement of the second kinematic chain includes moving the bar relative to a base of the robotic system in the movement direction of the first robotic arm.

Clause 12. The robotic system of any of clauses 1-11, further comprising: a robotically controlled third kinematic chain that is movably coupled to the second kinematic chain, wherein the instructions, when executed by the one or more processors, cause the processors to control movement of the third kinematic chain in accordance with the movement of the second kinematic chain.

Clause 13. The robotic system of clause 12, wherein: the first kinematic chain comprises a first robotic arm; the third kinematic chain comprises a second robotic arm; and the second kinematic chain comprises a bar that supports the first robotic arm and the second robotic arm.

Clause 14. The robotic system of clause 12 or 13, wherein controlling the movement of the third kinematic chain in accordance with the movement of the second kinematic chain includes in accordance with a determination that first movement criteria are met, maintaining a spatial relationship between at least a portion of the third kinematic chain and the second kinematic chain during the movement of the second kinematic chain.

Clause 15. The robotic system of any of clauses 12-14, wherein controlling the movement of the third kinematic chain in accordance with the movement of the second kinematic chain includes in accordance with a determination that second movement criteria are met, moving at least a portion of the third kinematic chain relative to the second kinematic chain during the movement of the second kinematic chain.

Clause 16. The robotic system of any of clauses 12-15, wherein controlling the movement of the third kinematic chain in accordance with the movement of the second kinematic chain includes in accordance with a determination that third movement criteria are met, moving at least a first portion of the third kinematic chain relative to the second kinematic chain during the movement of the second kinematic chain while maintaining a position of a distal end portion of the third kinematic chain relative to a base of the robotic system.

Clause 17. The robotic system of any of clauses 12-16, wherein controlling the movement of the second kinematic chain in accordance with the movement of the first kinematic chain includes in accordance with a determination that fourth movement criteria are met, stopping movement of the second kinematic chain.

Clause 18. A robotic medical system, comprising: a patient support platform; a first kinematic chain; and a second kinematic chain, wherein: the first kinematic chain is movably coupled to the second kinematic chain, and the robotic medical system includes a controller comprising one or more processors and memory storing instructions, wherein the instructions, when executed by the one or more processors, cause the processors to: adjust a spatial configuration of the first kinematic chain relative to the patient support platform in accordance with user input directed to the first kinematic chain; and in accordance with a determination that preset criteria are met during adjustment of the spatial configuration of the first kinematic chain in accordance with the user input directed to the first kinematic chain, activate automatic movement of the second kinematic chain relative to the patient support platform.

Clause 19. The robotic medical system of clause 18, wherein: the first kinematic chain is movably coupled to the second kinematic chain via a base joint that is capable of translating along the second kinematic chain, and adjusting the spatial configuration of the first kinematic chain relative to the patient support platform includes translating at least the base joint of the first kinematic chain along the second kinematic chain.

Clause 20. The robotic medical system of clause 18 or 19, wherein activating the automatic movement of the second kinematic chain relative to the patient support platform includes automatically translating the second kinematic chain relative to the patient support platform.

Clause 21. The robotic medical system of any of clauses 18-20, wherein: the first kinematic chain comprises a first robotic arm; and the second kinematic chain comprises a bar that supports the first robotic arm.

Clause 22. The robotic medical system of any of clauses 18-21, wherein the user input directed to the first kinematic chain is received via an input interface located on or proximate to the first kinematic chain.

Clause 23. The robotic medical system of any of clauses 18-22, wherein the user input directed to the first kinematic chain includes an input received via a button.

Clause 24. The robotic medical system of clause 23, wherein the input received via the button is a continuous user input.

Clause 25. The robotic medical system of clause 24, wherein the instructions, when executed by the one or more processors, cause the processors to deactivate the automatic movement of the second kinematic chain relative to the patient support platform in accordance with a determination that the continuous user input ceases to be detected via the button.

Clause 26. The robotic medical system of any of clauses 18-25, wherein adjusting the spatial configuration of the first kinematic chain relative to the patient support platform in accordance with user input directed to the first kinematic chain includes adjusting the spatial configuration of the first kinematic chain in accordance with direct physical manipulation of the first kinematic chain by a user under a first power-assisted manipulation mode of the first kinematic chain.

Clause 27. The robotic medical system of any of clauses 18-26, wherein the preset criteria requires that a force detected on one or more preset portions of the first kinematic chain exceeds a preset threshold force during the adjustment of the spatial configuration of the first kinematic chain in order for the preset criteria to be met.

Clause 28. A method for setting up a robotic medical system, the robotic medical system including a first kinematic chain and a second kinematic chain that is movably coupled the first kinematic chain, the method comprising: obtaining first data corresponding to manual manipulation of the first kinematic chain, wherein the manual manipulation of the first kinematic chain causes movement of the first kinematic chain relative to the second kinematic chain; and in accordance with a determination that the first data corresponding to manual manipulation of the first kinematic chain meets preset criteria, activating automatic movement of the second kinematic chain relative to a physical environment of the robotic medical system.

Clause 29. The method of clause 28, wherein the manual manipulation of the first kinematic chain causes translational movement of the first kinematic chain along a length of the second kinematic chain, and the preset criteria are met in accordance with a determination that the translational movement of the first kinematic chain has exceeded a preset cutoff limit along the length of the second kinematic chain.

Clause 30. The method of clause 28 or 29, wherein: the first kinematic chain comprises a first robotic arm; and the second kinematic chain comprises a bar that supports the first robotic arm.

Clause 31. The method of any of clauses 28-30, wherein activating the automatic movement of the second kinematic chain relative to a physical environment of the robotic medical system includes starting a translational movement of the second kinematic chain relative to a base of the robotic medical system.

Clause 32. The method of any of clauses 28-31, wherein the preset criteria are met in accordance with a determination that the first data corresponding to the manual manipulation of the first kinematic chain has exceeded a preset cutoff limit for more than a threshold amount of time.

Clause 33. The method of clause 32, wherein the threshold amount of time is at least two seconds.

Clause 34. The method of any of clauses 28-33, including: after activating the automatic movement of the second kinematic chain relative to the physical environment of the robotic medical system, receiving updated first data corresponding to additional manual movement of the first kinematic chain; and in accordance with a determination that the updated first data corresponding to the additional manual movement of the first kinematic chain does not meet the preset criteria, stopping the automatic movement of the second kinematic chain relative to the physical environment of the robotic medical system.

Clause 35. The method of clause 34, wherein the additional manual movement of the first kinematic chain causes reversal of the movement of the first kinematic chain along a length of the second kinematic chain.

Clause 36. The method of clause 34 or 35, wherein the first data includes a user input of a first type that is continuously maintained during the manual manipulation of the first kinematic chain, and the updated first data includes cessation of the user input of the first type.

Clause 37. The method of any of clauses 28-36, wherein the preset criteria require that the manual manipulation of the first kinematic chain is carried out in accordance with direct physical manipulation of the first kinematic chain by a user under a first power-assisted manipulation mode of the first kinematic chain.

Clause 38. The method of any of clauses 28-37, wherein the robotic system further includes a third kinematic chain that is movably coupled to the second kinematic chain, the method further comprising in accordance to the automatic movement of the second kinematic chain, controlling movement of the third kinematic chain.

Clause 39. The method of any of clauses 28-38, wherein the manual movement of the first kinematic chain along the second kinematic chain is constrained by a first limit along the second kinematic chain.

What is claimed is:

1. A robotic system, comprising:
a robotically controlled first kinematic chain;
a robotically controlled second kinematic chain that is movably coupled to the first kinematic chain;
a robotically controlled third kinematic chain that is movably coupled to the second kinematic chain; and
a controller that is communicably coupled to the first kinematic chain and the second kinematic chain, the controller including one or more processors and memory storing instructions,
wherein the instructions, when executed by the one or more processors, cause the processors to:
obtain data corresponding to the first kinematic chain;
control movement of the second kinematic chain in accordance with the data corresponding to the first kinematic chain; and
control movement of the third kinematic chain in accordance with the movement of the second kinematic chain.

2. The robotic system of claim 1, wherein obtaining the data corresponding to the first kinematic chain includes obtaining the data while the first kinematic chain is in a manual manipulation mode.

3. The robotic system of claim 1, wherein controlling the movement of the second kinematic chain in accordance with the data corresponding to the first kinematic chain includes automatically moving the second kinematic chain in accordance with a determination that the data corresponding to the first kinematic chain meets preset criteria.

4. The robotic system of claim 1, wherein controlling the movement of the second kinematic chain comprises controlling a translational movement of the second kinematic chain relative to a base of the robotic system.

5. The robotic system of claim 1, wherein:
the first kinematic chain comprises a first robotic arm; and
the second kinematic chain comprises a bar that supports the first robotic arm.

6. The robotic system of claim 5, wherein the first robotic arm comprises a base joint that is coupled to the bar and capable of translating along the bar.

7. The robotic system of claim 6, wherein the translation of the first robotic arm along the bar is constrained by a first limit along the bar.

8. The robotic system of claim 7, wherein the first limit includes a haptic wall that limits an extent of manual translation of the first robotic arm along the bar.

9. The robotic system of claim 5, wherein automatic movement of the bar is triggered in accordance with a cutoff limit being exceeded by the first robotic arm.

10. The robotic system of claim 5, where the data corresponding to the first kinematic chain includes a distance travelled by the first robotic arm along the bar.

11. The robotic system of claim 5, wherein the data corresponding to the first kinematic chain includes a movement direction of the first robotic arm along the bar, and controlling the movement of the second kinematic chain includes moving the bar relative to a base of the robotic system in the movement direction of the first robotic arm.

12. The robotic system of claim 1, wherein:
the first kinematic chain comprises a first robotic arm;
the third kinematic chain comprises a second robotic arm; and
the second kinematic chain comprises a bar that supports the first robotic arm and the second robotic arm.

13. The robotic system of claim 1, wherein controlling the movement of the third kinematic chain in accordance with the movement of the second kinematic chain includes in accordance with a determination that first movement criteria are met, maintaining a spatial relationship between at least a portion of the third kinematic chain and the second kinematic chain during the movement of the second kinematic chain.

14. The robotic system of claim 1, wherein controlling the movement of the third kinematic chain in accordance with the movement of the second kinematic chain includes in accordance with a determination that second movement criteria are met, moving at least a portion of the third kinematic chain relative to the second kinematic chain during the movement of the second kinematic chain.

15. The robotic system of claim 1, wherein controlling the movement of the third kinematic chain in accordance with the movement of the second kinematic chain includes in accordance with a determination that third movement criteria are met, moving at least a first portion of the third kinematic chain relative to the second kinematic chain during the movement of the second kinematic chain while maintaining a position of a distal end portion of the third kinematic chain relative to a base of the robotic system.

16. The robotic system of claim 1, wherein controlling the movement of the second kinematic chain in accordance with the movement of the first kinematic chain includes in accordance with a determination that fourth movement criteria are met, stopping movement of the second kinematic chain.

17. A robotic medical system, comprising:
a patient support platform;
a first kinematic chain; and
a second kinematic chain, wherein:
the first kinematic chain is movably coupled to the second kinematic chain, and
the robotic medical system includes a controller comprising one or more processors and memory storing instructions,
wherein the instructions, when executed by the one or more processors, cause the processors to:
adjust a spatial configuration of the first kinematic chain relative to the patient support platform in accordance with user input directed to the first kinematic chain; and
in accordance with a determination that preset criteria are met during adjustment of the spatial configuration of the first kinematic chain in accordance with the user input directed to the first kinematic chain, activate automatic movement of the second kinematic chain relative to the patient support platform.

18. The robotic medical system of claim 17, wherein:
the first kinematic chain is movably coupled to the second kinematic chain via a base joint that is capable of translating along the second kinematic chain, and
adjusting the spatial configuration of the first kinematic chain relative to the patient support platform includes translating at least the base joint of the first kinematic chain along the second kinematic chain.

19. The robotic medical system of claim 17, wherein activating the automatic movement of the second kinematic chain relative to the patient support platform includes automatically translating the second kinematic chain relative to the patient support platform.

20. The robotic medical system of claim 17, wherein:
the first kinematic chain comprises a first robotic arm; and
the second kinematic chain comprises a bar that supports the first robotic arm.

21. The robotic medical system of claim 17, wherein the user input directed to the first kinematic chain is received via an input interface located on or proximate to the first kinematic chain.

22. The robotic medical system of claim 17, wherein the user input directed to the first kinematic chain includes an input received via a button.

23. The robotic medical system of claim 22, wherein the input received via the button is a continuous user input.

24. The robotic medical system of claim 23, wherein the instructions, when executed by the one or more processors, cause the processors to deactivate the automatic movement of the second kinematic chain relative to the patient support platform in accordance with a determination that the continuous user input ceases to be detected via the button.

25. The robotic medical system of claim 17, wherein adjusting the spatial configuration of the first kinematic chain relative to the patient support platform in accordance with user input directed to the first kinematic chain includes adjusting the spatial configuration of the first kinematic chain in accordance with direct physical manipulation of the first kinematic chain by a user under a first power-assisted manipulation mode of the first kinematic chain.

26. The robotic medical system of claim 17, wherein the preset criteria requires that a force detected on one or more preset portions of the first kinematic chain exceeds a preset threshold force during the adjustment of the spatial configuration of the first kinematic chain in order for the preset criteria to be met.

27. A method for setting up a robotic medical system, the robotic medical system including a first kinematic chain and a second kinematic chain that is movably coupled the first kinematic chain, the method comprising:
obtaining first data corresponding to manual manipulation of the first kinematic chain, wherein the manual manipulation of the first kinematic chain causes movement of the first kinematic chain relative to the second kinematic chain; and
in accordance with a determination that the first data corresponding to manual manipulation of the first kinematic chain meets preset criteria, activating automatic movement of the second kinematic chain relative to a physical environment of the robotic medical system.

28. The method of claim 27, wherein the manual manipulation of the first kinematic chain causes translational movement of the first kinematic chain along a length of the second kinematic chain, and the preset criteria are met in accordance with a determination that the translational movement of the first kinematic chain has exceeded a preset cutoff limit along the length of the second kinematic chain.

29. The method of claim 27, wherein:

the first kinematic chain comprises a first robotic arm; and the second kinematic chain comprises a bar that supports the first robotic arm.

30. The method of claim 27, wherein activating the automatic movement of the second kinematic chain relative to a physical environment of the robotic medical system includes starting a translational movement of the second kinematic chain relative to a base of the robotic medical system.

31. The method of claim 27, wherein the preset criteria are met in accordance with a determination that the first data corresponding to the manual manipulation of the first kinematic chain has exceeded a preset cutoff limit for more than a threshold amount of time.

32. The method of claim 31, wherein the threshold amount of time is at least two seconds.

33. The method of claim 27, including:

after activating the automatic movement of the second kinematic chain relative to the physical environment of the robotic medical system, receiving updated first data corresponding to additional manual movement of the first kinematic chain; and in accordance with a determination that the updated first data corresponding to the additional manual movement of the first kinematic chain does not meet the preset criteria, stopping the automatic movement of the second kinematic chain relative to the physical environment of the robotic medical system.

34. The method of claim 33, wherein the additional manual movement of the first kinematic chain causes reversal of the movement of the first kinematic chain along a length of the second kinematic chain.

35. The method of claim 33, wherein the first data includes a user input of a first type that is continuously maintained during the manual manipulation of the first kinematic chain, and the updated first data includes cessation of the user input of the first type.

36. The method of claim 27, wherein the preset criteria require that the manual manipulation of the first kinematic chain is carried out in accordance with direct physical manipulation of the first kinematic chain by a user under a first power-assisted manipulation mode of the first kinematic chain.

37. The method of claim 27, wherein the robotic medical system further includes a third kinematic chain that is movably coupled to the second kinematic chain, the method further comprising in accordance to the automatic movement of the second kinematic chain, controlling movement of the third kinematic chain.

38. The method of claim 27, wherein the movement of the first kinematic chain relative to the second kinematic chain is constrained by a first limit along the second kinematic chain.

39. A robotic system, comprising:

a robotically controlled first kinematic chain, the first kinematic chain comprising a first robotic arm;

a robotically controlled second kinematic chain that is movably coupled to the first kinematic chain, the second kinematic chain comprising a rail that supports the first robotic arm; and a controller that is communicably coupled to the first kinematic chain and the second kinematic chain, the controller including one or more processors and memory storing instructions, wherein the instructions, when executed by the one or more processors, cause the processors to:

obtain data corresponding to the first kinematic chain; and control movement of the second kinematic chain in accordance with the data corresponding to the first kinematic chain.

* * * * *